(12) United States Patent
Ohmura et al.

(10) Patent No.: US 8,407,068 B2
(45) Date of Patent: *Mar. 26, 2013

(54) MEDICINE MANAGEMENT APPARATUS AND MEDICINE MANAGEMENT SYSTEM

(75) Inventors: Shiro Ohmura, Tokyo (JP); Eiichiro Indei, Tokyo (JP); Yoshihito Ohmura, Tokyo (JP)

(73) Assignee: Tosho Inc., Tokyo (JP)

( * ) Notice: Subject to any disclaimer, the term of this patent is extended or adjusted under 35 U.S.C. 154(b) by 104 days.

This patent is subject to a terminal disclaimer.

(21) Appl. No.: 12/917,649

(22) Filed: Nov. 2, 2010

(65) Prior Publication Data

US 2011/0066448 A1 Mar. 17, 2011

Related U.S. Application Data

(62) Division of application No. 11/629,735, filed on Feb. 15, 2007, now Pat. No. 7,917,375.

(51) Int. Cl.
  *G06Q 10/00* (2012.01)
(52) U.S. Cl. .......................................... 705/2; 221/222
(58) Field of Classification Search ........................ 705/2
  See application file for complete search history.

(56) References Cited

U.S. PATENT DOCUMENTS

| 5,805,455 | A | 9/1998 | Lipp |
| 6,339,732 | B1 | 1/2002 | Phoon |
| 8,020,725 | B2 * | 9/2011 | Yuyama et al. ............... 221/222 |
| 2002/0013640 | A1 | 1/2002 | Phoon |

FOREIGN PATENT DOCUMENTS

| JP | 59-077568 | 5/1984 |
| JP | 63-318674 | 12/1988 |
| JP | 03-264064 | 11/1991 |
| JP | 07-220011 | 8/1995 |
| JP | 08-007014 | 1/1996 |
| JP | 08-119202 | 5/1996 |
| JP | 08-339410 | 12/1996 |
| JP | 09182780 | 7/1997 |
| JP | 2001-199508 A | 7/2001 |
| JP | 2002-011072 A | 1/2002 |
| JP | 2002-119577 A | 4/2002 |
| JP | 2002126044 A | 5/2002 |
| JP | 2002157341 A | 5/2002 |

(Continued)

OTHER PUBLICATIONS

International Search Report of PCT/JP2005/008414 dated Aug. 2, 2005.

(Continued)

*Primary Examiner* — Hiep V Nguyen
(74) *Attorney, Agent, or Firm* — Matthew B. Dernier, Esq.; Gibson & Dernier LLP

(57) ABSTRACT

A medicine management apparatus includes: a medicine storage which stores a plurality of medicines used at a site of medical care; a storage and retrieval detector which, when a medicine handling personnel manipulates the apparatus to store or retrieve an accommodated medicine to be accommodated in the apparatus, physically detects the target accommodated medicine for which the apparatus is manipulated, differentiating it from the other accommodated medicines; and a counter which counts each type of the plurality of accommodated medicines. An injection prescription receiver receives injection prescription data from an external prescription analyzer. A retrieval determining unit determines whether the accommodated medicine detected as being retrieved is the accommodated medicine directed by the injection prescription data to be retrieved. A retrieval completion notification unit transmits a retrieval completion signal to the prescription analyzer, prompted by the completion of the retrieval of the accommodated medicine directed by the prescription data to be retrieved.

13 Claims, 34 Drawing Sheets

FOREIGN PATENT DOCUMENTS

| | | | |
|---|---|---|---|
| JP | 2002528149 | T | 9/2002 |
| JP | 2002315813 | A | 10/2002 |
| JP | 2003-292122 | A | 10/2003 |

OTHER PUBLICATIONS

International Preliminary Report on Patentability based on corresponding PCT/JP2005/008414, Dec. 28, 2006, 12 pgs.

Office Action for corresponding JP application 2004-183322, dated: Mar. 31, 2009.

Notification of Refusal for JP application 2003321758, dated: May 7, 2008.

Notification of Refusal for JP application 2003321758, dated: Oct. 7, 2008.

Decision to Dismiss Amendment for JP application 2003321758, dated: Apr. 14, 2009.

Office action for co-pending U.S. Appl. No. 11/629,735, dated Jan. 27, 2010.

Office action for co-pending U.S. Appl. No. 11/629,735, dated Apr. 22, 2010.

Office action for co-pending U.S. Appl. No. 11/629,735, dated Jul. 22, 2010.

Restriction Requirement for co-pending U.S. Appl. No. 11/629,735, dated Dec. 2, 2009.

Japanese Office Action for corresponding Japanese Application No. 2009-117807, Jul. 26, 2011.

\* cited by examiner

Fig. 7

| REVIEW DETAILS OF RETRIEVAL | | | | | |
|---|---|---|---|---|---|
| NEW (ORDINARY) INVOICE | MEDICINE NAME | SC | UT | DP | UT |
| HOSPITAL ADMISSION<br>INJECTION PRESCRIPTION:100236<br>FIRST   FULFILLED:2003/12/16<br>ROOM 578<br>PATIENT ID   :0315<br>PATIENT NAME:SATOSHI OKUBO<br>REQUESTING DOCTOR:TAKASHI ASAI | PERCAMI INJECTION FLUID | 1 | A | 1 | A |
| | NORMAL SALINE | 150 ml | | 150 ml | |
| RETURN | | | | | |

362 → (upper left box)
364 → (upper right table)
360

Fig. 8

| | START DATE | 2003 ▽ | DEC ▽ | 15TH ▽ |
|---|---|---|---|---|
| | END DATE | 2003 ▽ | DEC ▽ | 15TH ▽ |
| | HOSPITAL WARD | 6A | | |

| INJECTION PRESCRIPTION ID | DATE OF ISSUE | TIME OF ADMINISTRATION | RE-TRIEV-AL | CATEGORY | PATIENT ID | PATIENT NAME |
|---|---|---|---|---|---|---|
| 100236 | 2003-12-15 8:01 | 2003-12-15 13:00 | DONE | URGENT | 0315 | SATOSHI OKUBO |
| 100238 | 2003-12-15 8:06 | 2003-12-15 14:00 | DONE | URGENT | 0321 | K. MIYAKOZAWA |
| 100242 | 2003-12-15 8:16 | 2003-12-15 14:00 | — | URGENT RETURN | 0322 | M. AIHARA |
| 100243 | 2003-12-15 9:15 | 2003-12-15 14:30 | — | URGENT | 0408 | ATSUKO SANO |
| 100244 | 2003-12-15 10:28 | 2003-12-15 14:30 | DONE | URGENT | 0101 | HARUMI SATO |
| 100259 | 2003-12-15 11:10 | 2003-12-15 15:00 | — | URGENT ADDITION | 0311 | MASAO TAKAHASHI |
| 100261 | 2003-12-15 12:10 | 2003-12-15 15:00 | DONE | URGENT | 0382 | TOME TODA |
| 100262 | 2003-12-14 21:17 | 2003-12-15 20:00 | — | TEMPORARY | 0372 | TOMOHISA OGAWA |
| 100263 | 2003-12-14 20:16 | 2003-12-15 21:00 | — | TEMPORARY | 0379 | GOICHI YAMADA |
| 100264 | 2003-12-14 14:01 | 2003-12-15 21:00 | — | URGENT ADDITION | 0380 | NAOTOSHI OZAWA |

Fig. 22

SELECT SET OF ARTICLES

SET CATEGORY | SURGERY — 942
SET OF ARTICLES | SURGERY-HERNIA — 944

1/1 — 958

TOUCH TO INCREASE AMOUNT ➕ ➖
NUMBER OF SETS × 2 — 962
RETRIEVAL — 964
RETURN — 966

| ITEM CODE | MEDICINE NAME/ SPECIFICATION NAME | PRE-SCRIBED | AMOUNT | UNIT |
|---|---|---|---|---|
| 7252 | NETRAGATHETER | 2 | 2 | PIECE |
| 0091 | LOANSTUDIES | 1 | 1 | PIECE |
| 1001 | ISOGIN FLUID | 150 | 150 | ml |
| 1669 | NORMAL SALINE | 200 | 200 | ml |
| 2031 | PDD II 3-0 | 1 | 1 | PIECE |
| 5722 | ZUKINSTEPROYAL | 1 | 1 | PIECE |
| 7538 | BYRILK (PACK OF 8) | 1 | 1 | PACK |
| 8644 | PROLIN SH-2 | 2 | 2 | PIECE |
| 5643 | SILBRED (PACK OF 10) | 1 | 1 | SHEET |
| 1960 | NEUTRAL ELECTRODE | 1 | 1 | SHEET |

| TIME | C | | | | MEDICINE (SET) NAME/ SPECIFICATION NAME | AMOUNT | UNIT |
|---|---|---|---|---|---|---|---|
| 18:13:12 | RV | | | | PERCAMI INJECTION FLUID | 2 | A |
| 18:18:42 | RN | | | | PERCAMI INJECTION FLUID | ▲1 | A |
| 18:36:12 | RV | | | | SURGRY-HERNIA | 1 | SET |
| 18:38:02 | RV | | | | NETRACATHETER | 1 | PIECE |

MEDICAL OPERATION ID 100236
PATIENT NAME HARUMI SATO

MEDICINE RETRIEVAL OPERATOR (FUMIAKI YAMASHITA)

URGENT INTERRUPTION

Page: 1/1

MAIN MENU

CATEGORY  SET
NON-ACCOMMODATED ARTICLE SEARCH INPUT
RETURN OF ACCOMMODATED MEDICINE
DAMAGE REGISTRATION MODE

TO MEDICINE HANDLING PERSONNEL ID INPUT — 898

972

TAKE OUT MEDICINES OUT OF STORAGE

| JAN CODE | MEDICINE CODE | MEDICINE NAME | SPECIFICATION NAME | BENEFICIAL EFFECT | ... | DESIGNATED CATEGORY | DIAMETER | HEIGHT | CASSETTE |
|---|---|---|---|---|---|---|---|---|---|
| 4987293091761 | 30332C | PERCAMI INJECTION FLUID | 0.3%3mL 1 TUBE | LOCAL ANESTHETIC | ... | D | 14.53 | 65 | S |
| 4987233010722 | 300240 | AMEXATE INJECTION FLUID 0.5mg | 0.5mg5mL 1 TUBE | RESPIRATORY STIMULANT | ... | D | 16.36 | 65 | S |
| 4987057038971 | 300590 | ISOBAN INJECTION | 100mg5mL 1 TUBE | CARDIAC STIMULANT | ... | D | 17.09 | 70 | S |
| 4987195365182 | 301550 | RIGYRANOGEN C INJECTION FLUID | 0.02%2mL 1 TUBE | CARDIAC STIMULANT | ... | D | 12.10 | 59 | SS |
| 4987107007728 | 302080 | TRANAMIN S INJECTION | 10%10mL 1 TUBE 1g | HEMOSTAT | ... |  | 17.96 | 89 | S |
| 4987233044703 | 302100 | CORNICAM INJECTION | 10mg2mL 1 TUBE | SEDATIVE HYPNOTIC/ANTIANXIETY AGENT | ... | PY | 12.34 | 54 | SS |
| 4987081282319 | 302310 | VORADRENALINE | 1mg1mL 1 TUBE | ADRENAL HORMONE PREPARATION | ... | D | 10.40 | 54 | 3S |
| 4987081395415 | 303590 | NASCRASSUS FOR INTRAVENOUS INJECTION 10mg | 10mg1 BOTTLE | SKELETAL MUSCLE RELAXANT | ... | PO | 21.79 | 58 | L |
| ...... | ...... | ...... | ...... | ...... | ...... | ...... | ...... | ...... | ...... |

| MEDICAL OPERATION ID 1230 | PATIENT ID 1232 | SCHEDULED OPERATION TECHNIQUE 1234 | RESPONSIBLE DOCTOR 1236 | SURGEON 1238 | ... | SCHEDULED DATE 1240 |
|---|---|---|---|---|---|---|
| 1002352 | 9305277 | LOW ANTERIOR RESECTION OF THE RECTUM | K. KITAMURA | K. KITAMURA | ... | 2003/7/31 |
| 1002361 | 9305911 | VASCULAR/BYPASS TRANSPLANTATION | SATOSHI KIMURA | SATOSHI KIMURA | ... | 2003/8/ 1 |
| 1002363 | 9304599 | ABDOMINO-SACRAL RECTECTOMY | K. KITAMURA | K. KITAMURA | ... | 2003/8/ 1 |
| 1002377 | 9305496 | RIGHT COLECTOMY | RYUICHI SANO | RYUICHI SANO | ... | 2003/8/ 4 |
| 1002380 | 9304924 | TOTAL EXTIRPATION OF STOMACH | YASUNORI KYODA | YASUNORI KYODA | ... | 2003/8/ 4 |
| 1002384 | 9305019 | LOW ANTERIOR RESECTION OF THE RECTUM | K. KITAMURA | K. KITAMURA | ... | 2003/8/ 4 |
| ...... | ...... | ...... | ...... | ...... | ...... | ...... |

| PATIENT ID 1250 | PATIENT NAME 1252 | AGE 1254 | SEX 1256 | BLOOD TYPE 1258 | HEIGHT 1260 | WEIGHT 1262 | ... | HOSPITAL ADMISSION 1264 |
|---|---|---|---|---|---|---|---|---|
| 9305277 | HARUMI SATO | 8 | FEMALE | B | 127 | 26.3 | ... | ○ |
| 9305921 | H. OFUCHI | 16 | MALE | O | 176 | 64.2 | ... | OUT-PATIENT |
| 9306003 | YUKO TAKAI | 29 | FEMALE | A | 158 | 45.0 | ... | ○ |
| 9306112 | J. NAGAMI | 4 | FEMALE | A | 105 | 18.7 | ... | ○ |
| 9305911 | S. SASAKI | 45 | MALE | O | 163 | 71.0 | ... | ○ |
| 9304599 | KIYOSHI SATO | 35 | MALE | A | 176 | 65.8 | ... | ○ |
| ...... | ...... | ...... | ...... | ...... | ...... | ...... | ...... | ...... |

| MACHINE ID 1270 | NAME MEDICINE/ MEDICAL MATERIAL 1272 | MEDICINE IDENTIFICATION ID 1274 | CATE-GORY 1276 | RETRIEVED AMOUNT 1278 | UNIT 1280 | STOCK AMOUNT 1282 |
|---|---|---|---|---|---|---|
| 0001 | ANEXATE INJECTION FLUID 0.5mg | 300240 | AC | 2 | A | 6 |
| | MASCRASSUS FOR INTRAVENOUS | 303590 | AC | 1 | BOTTLE | 7 |
| | SYRINGE 10ml | 311460 | MR | 3 | PIECE | 27 |
| | NORMAL SALINE 500ml | 305800 | NA | 2 | BOTTLE | 8 |
| 0002 | CORMICAM INJECTION | 302100 | AC | 2 | A | 17 |
| | DISTILLED WATER (INJECTION) 20ml | 302680 | AC | 1 | A | 5 |
| | POTASH SOAP | 306210 | NA | 40 | g | 80g |
| ...... | ...... | ...... | ...... | ...... | ...... | ...... |

738

MEDICINE MANAGEMENT APPARATUS AND MEDICINE MANAGEMENT SYSTEM

CROSS REFERENCE TO RELATED APPLICATIONS

This application is a divisional of U.S. patent application Ser. No.: 11/629,735, filed Feb. 15, 2007, now U.S. Pat. No. 7,917,375, the entire disclosure of which is hereby incorporated by reference.

BACKGROUND OF THE INVENTION

1. Field of the Invention

The present invention relates to a technology for managing medicines used at a site of medical care and, more particularly, to a technology for managing the retrieval of prescribed medicines.

2. Description of the Related Art

Medicines administered by direct injection into a blood vessel are absorbed and act more promptly than orally administered medicines. At the same, however, mistakes in administration of injection medicines affect the human body more severely so that more caution is required in administration.

The process of administering injection medicines can largely be divided into the following five stages:

(1) a doctor prepares prescription of medicines to be administered to a patient by injection (hereinafter, instruction on injection medicines to be administered will be referred to as "injection prescription");
(2) a pharmacist or the like prepares multiple injection medicines designated in the injection prescription in a hospital dispensary;
(3) the pharmacist examines whether the injection medicine designated in the injection prescription matches the injection medicine actually prepared;
(4) carry the multiple injection medicines prepared in the dispensary to a hospital ward;
(5) prepare an admixture of the injection medicines and infusion fluids;
(6) the injection medicine prepared in (5) (hereinafter, referred to as prepared injection medicine) is administered to the patient at a dosage time designated in the injection prescription.

[patent document No. 1]
JP 2001-199508
[patent document No. 2]
JP 1996-339410
[patent document No. 3]
JP 1995-220011
[patent document No. 4]
JP 1991-264064
[patent document No. 5]
JP 1988-318674
[patent document No. 6]
JP 1984-77568
[patent document No. 7]
JP 2001-199508
[patent document No. 8]
JP 2002-011072

Hospitals accommodating a large number of inpatients face a great burden of preparing injection medicines administered to the patients. Normally, therefore, Injection medicines are prepared in a dispensary on a day before the scheduled date for administration. However, injection prescriptions once issued are often changed depending on the state of health of patients or test results. In such a case, injection medicines prepared according to the original injection prescription may sometimes be returned without being used. Alternatively, an admixture of injection medicines may have already been prepared and has to be discarded.

In the type of operation as described above, injection medicines that are not used at a site of medical care such as a hospital ward may be kept in stock each time an injection prescription is changed. Conversely, a change of injection prescription may require new injection medicines, forcing a pharmacist or a nurse to go back and forth between a dispensary and a site of medical care for transportation of medicines. It may be possible to provide a stock of medicines at a site of medical care for immediate retrieval. This will necessitates, however, distributed medicine management, which makes stock control complicated. Accordingly, a general operation is that medicines are centrally managed at a dispensary and injection medicines are prepared in advance.

Because a change of injection prescription is likely to invite an error in administering injection medicines, medicine handling personnels are required to exercise utmost care. As described, there is a problem at a conventional site of medical care in that medicine handling personnels are heavily burdened.

SUMMARY OF THE INVENTION

One embodiment of the present invention relates to a medicine management apparatus.

The apparatus accommodates a plurality of medicines used at a site of medical care as accommodated medicines. When a medicine handling personnel manipulates the apparatus to retrieve accommodated medicines, the apparatus counts the accommodated medicines type by type, by physically detecting them. The apparatus receives prescription data designating the retrieval of accommodated medicines from an external prescription management apparatus and determines whether the accommodated medicine detected as being retrieved is the accommodated medicine directed by the prescription data to be taken out of storage. When the retrieval of the accommodated medicine directed by the prescription data to be retrieved is completed, the apparatus transmits a predetermined retrieval completion signal to the prescription management apparatus.

The term "accommodated medicine" refers drugs and medicines, including those dissolved before use, which are accommodated in a medicine storage. The term "non-accommodated article", which will be described later, is a notion opposite to the accommodated medicine and encompass drugs and medicines that are not accommodated in the medicine storage. Hereinafter, accommodated medicines and non-accommodated articles are collectively referred to as "medicines". The collective term "medicines" may also encompass medical resources and infusion fluids.

The apparatus may inform a medicine handling personnel of unauthorized retrieval when it is determined that the accommodated medicine detected as being retrieved is not the accommodated medicine directed the prescription data to be taken out of storage. "Prescription data" may designate the retrieval of at least one accommodated medicine scheduled to be administered in accordance with the condition of a patient. By alerting of unauthorized retrieval, the medicine handling personnel is relieved of the burden of reviewing whether the retrieval of accommodated medicines is completed properly in accordance with prescription data such as injection prescription.

The prescription data may designate the retrieval of at least one non-accommodated article in addition to accommodated medicines. The apparatus accepts an input regarding a non-accommodated article to be taken out of storage and determines whether the non-accommodated article which is taken out by the medicine handling personnel is the medicine directed by the prescription data to be taken out of storage. When the retrieval of accommodated medicines and non-accommodated articles directed by the prescription data to be taken out of storage is completed, the apparatus may transmit a retrieval completion signal to the prescription management apparatus.

The apparatus may shift, in accordance with an instruction provided by the medicine handling personnel, the mode of retrieval to an emergency retrieval mode wherein the accommodated medicine is retrieved without depending on prescription data. The apparatus may transmit emergency retrieval information regarding the accommodated medicine detected as being retrieved in the emergency retrieval mode to an external emergency retrieval management apparatus. The emergency retrieval information may relate the accommodated medicine detected as being retrieved to a patient ID. Alternatively, the emergency retrieval information may relate the accommodated medicine detected as being retrieved to a usage ID for identification of the usage of medicine retrieved. According to the embodiment, it is possible to prepare necessary medicines at the discretion of the site of medical care in accordance with the condition of a patient. By transmitting emergency retrieval information, it is more easy to trace the type of medicines used and the reason they are used, even when a treatment not based upon prescription data is performed.

Another embodiment of the present invention relates to a medicine management system.

The system comprises the medicine management apparatus described above and a prescription management apparatus which designates the retrieval of an accommodated medicine from the medicine management apparatus in accordance with prescription data. The prescription management apparatus stores prescription fulfillment status indicating whether the retrieval of an accommodated medicine based on the prescription data is completed. The prescription fulfillment status is updated when a retrieval completion signal is received from the medicine management apparatus. The medicine management apparatus may transmit the retrieval completion signal substantially on a real time basis, when the retrieval of the accommodated medicine directed to be retrieved is completed. Upon receiving the retrieval completion signal, the prescription management apparatus may update the prescription fulfillment information substantially on a real time basis. The term "substantially on a real time basis" refers to a mode wherein, upon completion of a predetermined process, control proceeds to a subsequent process without requiring the fulfillment of a condition such as a manipulation by a user or by an external apparatus, or a lapse of a predetermined period of time. The prescription management apparatus may be prompted by the retrieval completion signal from the medicine management apparatus to update stock information throughout the multiple medicine management apparatuses.

According to the embodiments, a medicine handling personnel can prepare medicines at a site close to patients by allowing the medicine management apparatus provided in each hospital ward to receive prescription data such as injection prescription. Medicines can easily be managed in a distributed manner using multiple medicine management apparatuses, instead of being centrally managed at a dispensary. Since a retrieval completion signal is transmitted when a medicine is retrieved from the medicine management apparatus, stock control throughout the hospital is easy even if the medicines are provided in a distributed manner and retrieved according to prescription data.

The present invention is effective in reducing the burden incurred in handling medicines at a site of medical care.

BRIEF DESCRIPTION OF THE DRAWINGS

FIG. 7 shows a retrieval review screen of the medicine management apparatus according to the first embodiment.

FIG. 8 shows an injection prescription list display screen displaying prescription fulfillment status in the prescription analyzer according to the first embodiment.

FIG. 22 shows a set of article input screen displayed when a set of articles is selected from the set of articles selection screen of FIG. 21, according to the second embodiment.

FIG. 23 shows a medicine retrieval screen displayed when a duplicate retrieval is detected according to the second embodiment.

FIG. 30 shows the data structure of a medicine database according to the second embodiment.

FIG. 31 shows the data structure of a medical operation database according to the second embodiment.

FIG. 32 shows the data structure of a patient database according to the second embodiment.

FIG. 33 shows the data structure of a retrieval database according to the second embodiment.

EXPLANATION OF SYMBOLS 100 medicine management apparatus, 102 display device, 104 barcode reader, 106 medicine storage, 108 catalog, 110 cassette, 114 printer, 116 cart, 120 bottle storage, 121 external storage, 122 user interface processing unit, 124 retrieval determination unit, 126 communication processing unit, 128 mechanism controller, 130 data storage, 132 input processing unit, 134 print processing unit, 136 output processing unit, 138 barcode input unit, 140 screen input unit, 142 screen display unit, 144 audio output unit, 146 storage and retrieval detector, 148 medicine storing unit, 150 counter, 152 injection prescription receiver, 154 retrieval completion notification unit, 156 retrieval information transmitter, 160 retrieval completion signal receiver, 162 retrieval information communication unit, 164 injection prescription receiver, 166 injection prescription transmitter, 168 label data generator, 170 prescription fulfillment status storage, 172 communication processing unit, 174 injection prescription analyzer, 176 retrieval information storage, 200 hospital, 202 prescription database, 204 stock database, 206 medical accounting system, 208 electronic patient chart system, 210 stock control system, 212 injection prescription input terminal, 214 input terminal for a dispensary, 216 communication network, 218 patient database, 220 medical information system, 222 medicine database, 250 prescription analyzer, 600 medicine management apparatus, 602 display device, 604 barcode reader, 606 medicine storage, 608 catalog, 610 cassette, 614 printer, 616 cart, 620 network, 622 integrated terminal, 700 hospital, 720 medical information system, 730 medical accounting system, 732 electronic patient chart system, 734 stock control system, 736 medical operation database, 738 retrieval database, 740 patient database, 742 medicine database, 750 user interface processing unit, 752 barcode input unit, 754 audio processing unit, 756 screen input unit, 758 input processing unit, 760 screen display unit, 762 controller, 770 communication processing unit, 772 communicating unit, 774 format converter, 776 data storage, 778 data input and output unit, 780 mechanism controller, 782 storage and retrieval detector, 784 medicine storage, 786 counter, 790 print processing unit

DETAILED DESCRIPTION OF THE INVENTION

A description of the present invention will be given by highlighting two illustrative embodiments.

The first embodiment relates to a medicine management apparatus which receives data for injection prescription from an external source and which monitors whether the medicine actually taken out of storage matches the medicine directed by the injection prescription data to be taken out of storage.

(First Embodiment)

Figure 1:
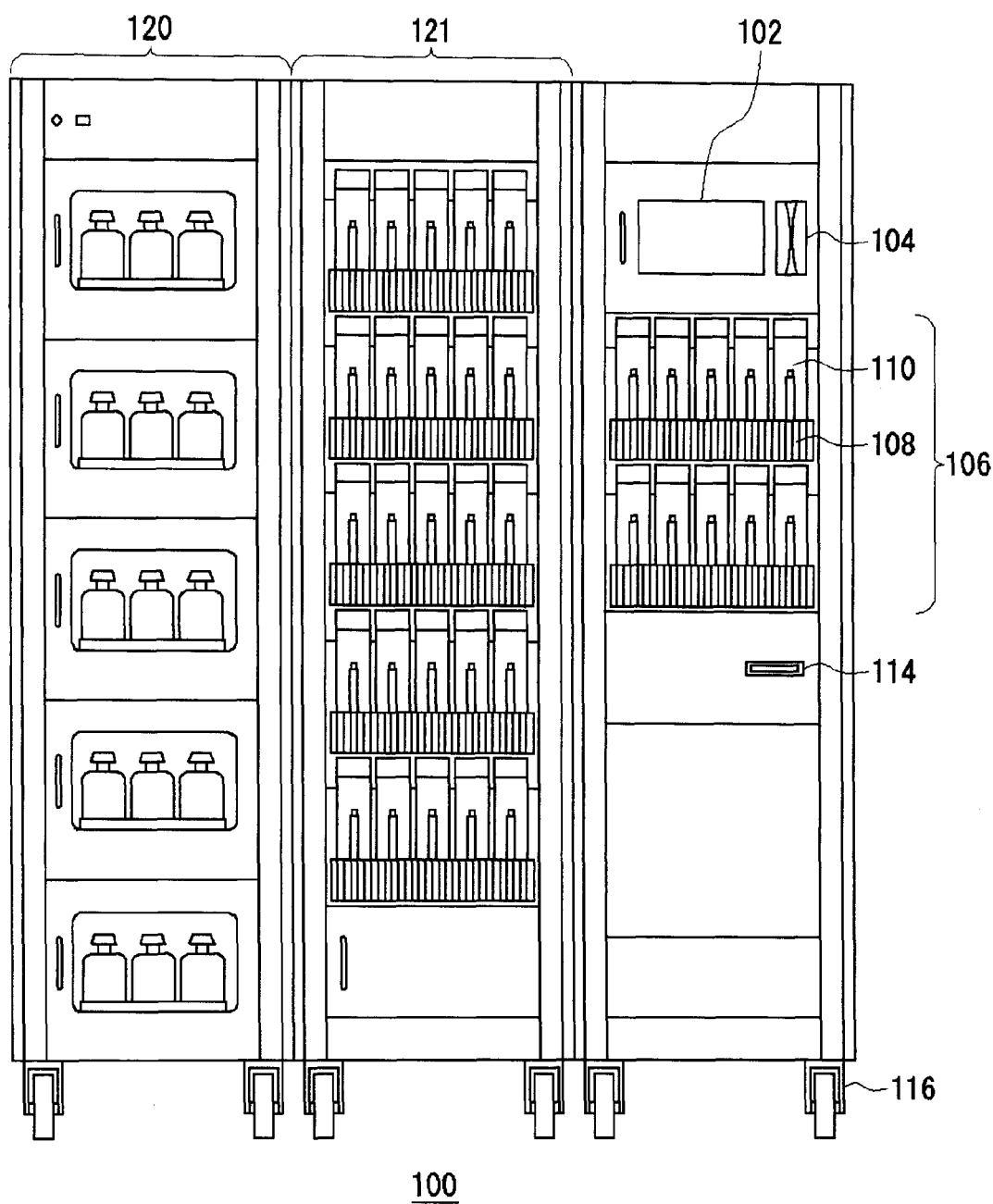
FIG. 1 shows the appearance of a medicine management apparatus according to a first embodiment.

FIG. 1 shows the appearance of a medicine management apparatus.

The medicine management apparatus main body is configured to be movable by a cart 116. A display apparatus 112 displays information to a medicine handling personnel such as a nurse. The following description assumes that a nurse uses the medicine management apparatus 100. The display device 102 operates as a touch panel to accept an input from the nurse via a graphics button or the like on a screen. A known input device such as a keyboard or a mouse may be used for input.

A barcode reader 104 is a device for scanning a barcode such as that assigned for identification of a non-accommodated article or that assigned for identification of a patient. The barcode reader 104 may be isolated from the medicine management apparatus 100. In this case, barcode information read by the barcode reader 104 may be transmitted wirelessly to the medicine management apparatus 100. The description of the first embodiment will be given primarily on an assumption that the barcode reader 104 isolated from the medicine management apparatus 100 scans a barcode. A nurse inputs information regarding storage and retrieval to the medicine management apparatus 100 by scanning a barcode assigned to a non-accommodated article taken into and out of storage by using the barcode reader 104. A medicine storage 106 is a shelf to store accommodated medicines. The medicine storage 106 is divided into tiers by multiple catalogs 108. Each catalog 108 is further partitioned by multiple cassettes 110. Each of the cassettes 110 stores medicines of a single type.

The cassette 100 is normally designed to store ampules or vials containing injection medicines. Alternatively, the cassette 110 may store medicines contained in a box, injection medicines packaged in a syringe or external medicines. An adaptor container conforming to a predetermined standard may be provided in order to store medicines of a form that can not themselves be stored in the cassette 110. Medicines of such a form can be stored in the cassette 110 by introducing them into the adaptor container. The term "injection medicine" in this specification is intended to mean medicines in general that represent an ingredient in a prepared injection medicine administered to a patient.

Each of the cassettes 110 is provided with a mechanism for mechanically detecting the storage and retrieval of accommodated medicines stored in the cassette 110, by using a known method. Thereby, the medicine management apparatus 100 detects the storage and retrieval of the accommodated medicines. Each of the cassettes 110 is also provided with a mechanism for mechanically counting the number of accommodated medicines, by using a known method. Thereby, the medicine management apparatus 100 counts the number of accommodated medicines. The known methods referred herein are disclosed in, for example, JP 2001-199508. The medicine storage 106 is normally protected by a protective means such as a shutter so as to permit only authenticated nurses to take out medicines. The shutter is controlled by a method described later to be opened upon authentication of a nurse.

An external storage 121 also stores medicines by a similar mechanism. The external storage 121 functions as an external medicine storage 106. A bottle storage 120 stores infusion fluids contained in bottles. Like the medicine storage 106, the bottle storage 120 is also provided with a mechanism for mechanically detecting the storage and retrieval of bottles. Thereby, the medicine management apparatus 100 is capable of detecting the storage and retrieval of the bottles stored in the bottle storage 120.

The medicine management apparatus 100 may be provided with a multi-purpose drawer. The multi-purpose drawer may store medicines that cannot be stored in the medicine storage 106 (i.e., non-accommodated articles). Non-accommodated articles may not necessarily be stored in the multi-purpose drawer. A printer 114 is a device for printing information.

Figure 2:
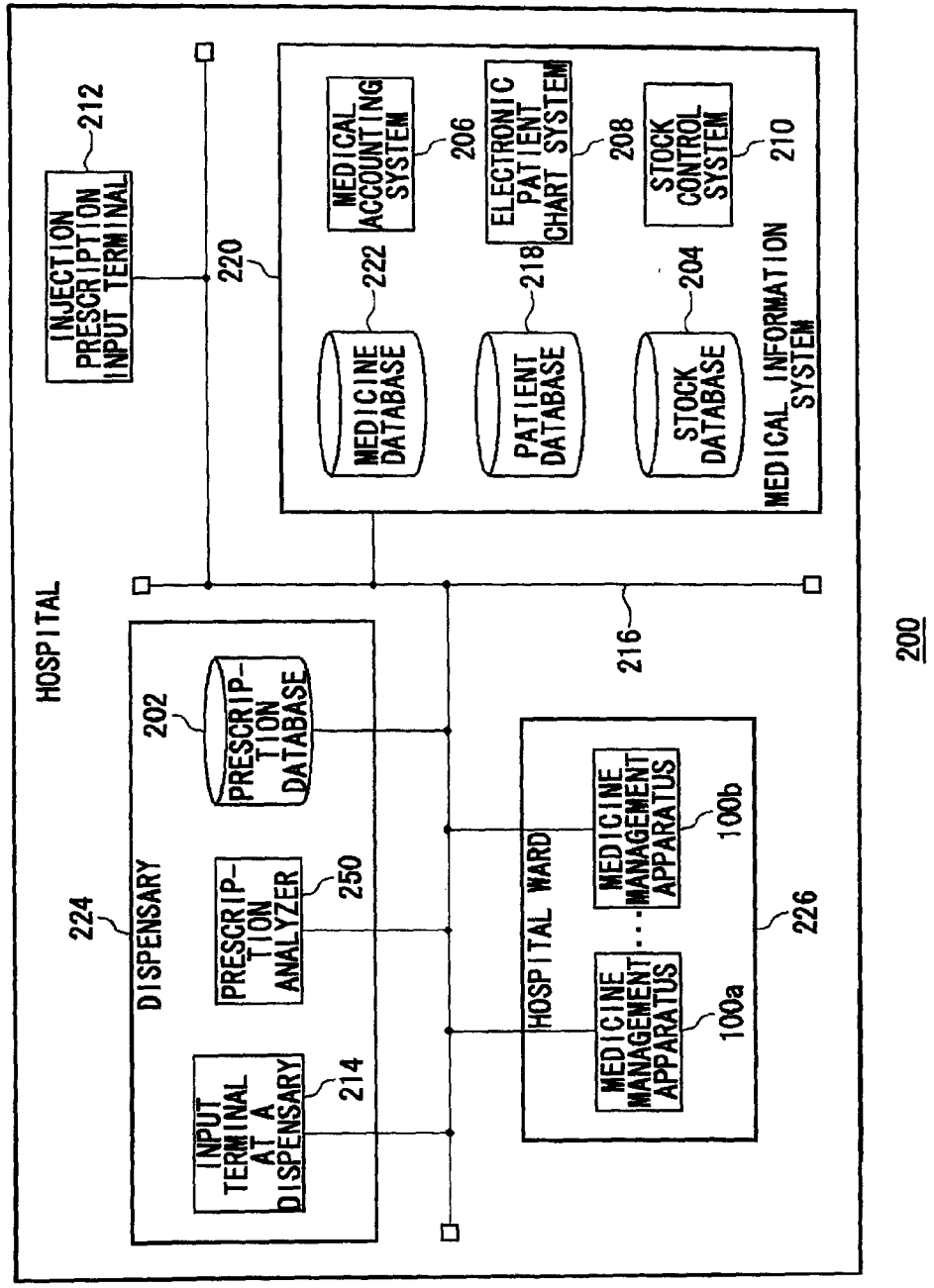
FIG. 2 shows a hardware structure in a hospital including a medicine management apparatus.

FIG. 2 shows a hardware structure in a hospital including a medicine management apparatus.

At a hospital ward 226 in a hospital 200, multiple medicine management apparatuses 100 including medicine management apparatuses 100a and 100b are connected to a communication network 216. The communication network 216 may be a local area network (LAN) or a dedicated circuit. The communication network 216 is connected to an external communication line such as the Internet. Connected also to the communication network 216 are an injection prescription input terminal 212, a medical information system 220, an input terminal for a dispensary 214, a prescription database 202 and a prescription analyzer 250.

Multiple injection prescription input terminals 212 are provided at respective medical departments to receive data for injection prescription from a doctor or a pharmacist. The data for injection prescription represents data for prescription designating injection medicines to be administered to a patient. The injection prescription data includes the name of injection medicines, the number of medicines dispensed, route of administration such as intravenous injection or collateral vessel injection, scheduled date for administration, name of the patient, age of the patient, medical department and name of a personnel inputting the data. The medical information system 220 collects the injection prescription data input at the respective medical departments in the hospital 200.

The prescription analyzer 250, the input terminal for a dispensary 214 and the prescription database 202 are provided in a dispensary 224 and are connected to the communication network 216. The injection prescription data stored in the prescription database 202 is input via the injection prescription input terminal 212, The prescription database 202 also stores information indicating whether injection medicines are ready to be taken out of storage in accordance with the injection prescription data. The prescription analyzer 250 acquires the injection prescription data from the prescription database 202 and transmits the prescription data to the input terminal for a dispensary 214 and the medicine management apparatus 100. The medicine management apparatus 100 is provided in each hospital ward. The input terminal for a dispensary 214 is a general-purpose terminal such as a personal computer provided in the dispensary. In each hospital ward or dispensary, a network printer or a communication terminal may be connected to the communication network 216.

The medical information system 220 is a system provided in each hospital 200. The internal configuration of the medical information system 220 varies depending on the situation of the hospital 200. In the following description, it is assumed that the medical information system 220 according to the first embodiment includes a medicine database 222, a patient database 218, a stock database 204, a medical accounting database 206, an electronic patient chart system 208 and a stock control system 210.

The medicine database 222 stores information related to medicines such as injection medicines. The patient database 218 stores patient information. The stock database 204 stores stock information on medicines used in the entire hospital 200.

The medical accounting system 206 is a system primarily for managing money charged for each patient. The electronic patient chart system 208 is a system primarily for managing chart information for each patients. The stock control system 210 is a system for stock control of medicines used in the entire hospital 200.

The injection medicine directed by the prescription data to be taken out of storage is prepared at the dispensary on a day before the date of administration to a patient (hereinafter, referred to as a scheduled administration date). By preparing an admixture of injection medicines on the scheduled administration date, a prepared injection medicine is prepared and administered to the patient at a dosage time designated in the injection prescription data. The injection prescription data may often be changed after the injection medicine is prepared. The change may take place on a date before the scheduled administration date or on the scheduled administration date. Thus, the injection prescription data may be rewritten once, twice or more depending on the situation.

The injection prescription data according to this embodiment is organized into three categories "ordinary", "temporary", "urgent" depending on the immediacy of the scheduled administration date. The condition of the patient may require that the prepared injection medicine be administered to the patent at the discretion of the site of medical care without depending on the injection prescription data (hereinafter, the administration in such a case will be referred to as "emergency administration"). In this embodiment, a prepared medicine is administered to the patient in one of the following modes of operation.

(A) In the Case of Ordinary Injection Prescription

An ordinary injection prescription is an injection prescription designating an administration date scheduled within twenty four hours. Normally, an ordinary injection prescription designates regularly scheduled administration to the patient. The prescription analyzer 250 acquires injection prescription data stored in the prescription database 202. If the injection prescription data thus acquired is ordinary injection prescription data, the prescription analyzer 250 transmits the data to the input terminal for a dispensary 214 provided at the dispensary. In order to enhance efficiency in operation, sets of injection medicines are prepared at the dispensary during scheduled hours every day. Hereinafter, the scheduled hours will be referred to as "preparation hours". The preparation hours may be scheduled several times in a day. The prescription analyzer 250 transmits the ordinary injection prescription data periodically during the preparation hours. More specifically, the prescription analyzer 250 causes the network printer connected to the input terminal for a dispensary 214 to print a label (hereinafter, referred to as "injection prescription label") carrying the particulars of the injection prescription data. At the dispensary, a pharmacist receiving the injection prescription label prepares injection medicines carried in the injection prescription label. The injection prescription label is an sticker that can be adhesively attached to a container of a prepared injection medicine.

The injection prescription label carries an injection prescription ID for uniquely identifying the injection prescription data and a barcode generated in association with the ID (hereinafter, referred to as "injection prescription code"). Once the designated injection medicines are taken out of storage, the pharmacist enters the injection prescription ID carried in the ordinary injection prescription data via the input terminal for a dispensary 214 so as to notify the prescription analyzer 250 that the medicines are successfully taken out of storage. The injection medicines thus prepared are transported at a time to the hospital ward on the scheduled administration date. Once transported, an admixture of injection medicines is prepared. The injection medicine thus prepared is administered to the patient on the scheduled administration time carried in the injection prescription label.

(B) In the Case of Temporary Injection Prescription

A temporary injection prescription is an injection prescription designating administration within twelve hours. A temporary injection prescription may designate modification of an ordinary injection prescription. Handling of a temporary injection prescription may be in accordance with one of the following two modes of operation.

(B-1) In this mode of operation, a temporary injection prescription is handled in almost the same way as ordinary injection prescription data. The prescription analyzer 250 acquires injection prescription data from the prescription database 202. If the injection prescription data thus acquired is temporary injection prescription data, the prescription analyzer 250 transmits the data to the input terminal for a dispensary 214 provided at the dispensary. The prescription analyzer 250 transmits the temporary injection prescription data during the preparation hours scheduled at the dispensary. The prescription analyzer 250 causes the network printer connected to the input terminal for a dispensary 214 to print a injection prescription label carrying the particulars of the temporary injection prescription data. At the dispensary, a pharmacist receiving the injection prescription label prepares injection medicines carried in the injection prescription label. In the case of temporary injection prescription data, too, the pharmacist notifies the prescription analyzer 250 that the medicines are successfully taken out of storage via the input terminal for a dispensary 214. The subsequent steps are the same as those of ordinary injection prescription in (A).

(B-2) The prescription analyzer 250 makes the injection prescription data acquired from the prescription database 202 accessible in the hospital 200 via the communication network 216. Terminals connected to the communication network 216, such as the input terminal for a dispensary 214 and the medicine management apparatus 100, can acquire the injection prescription data made accessible by the prescription analyzer 250 such that the data is viewable by a browser installed in the terminals. A nurse can access the prescription analyzer 250 from the medicine management apparatus 100 and request download of the temporary injection prescription data scheduled to be used for administration at the hospital ward. The prescription analyzer 250 receiving the request causes the medicine management apparatus 100 to print the injection prescription label corresponding to the temporary injection prescription data thus requested. The nurse causes the barcode reader 104 to scan the injection prescription code. The medicine management apparatus 100 identifies the injection prescription ID corresponding to the input injection prescription code and acquires the corresponding injection prescription data from the prescription analyzer 250. The prescription data thus acquired is displayed on the display device 102.

In accordance with the particulars of the temporary injection prescription data displayed on the display device 102, the nurse takes medicines accommodated in the medicine management 100 out of storage or takes non-accommodated articles in the hospital ward out of storage. When the medicines are taken out of storage (i.e. retrieved), the medicine management apparatus 100 notifies the prescription analyzer 250 that the retrieval based on the temporary injection prescription data is completed by transmitting thereto a retrieval completion signal. If the prescription analyzer 250 receives the retrieval completion signal from the medicine management apparatus 100 prior to transmitting the temporary injection prescription data to the input terminal for a dispensary 214 as described in (B-1), the prescription analyzer 250 no longer transmits the temporary injection prescription data to the input terminal for a dispensary 214.

Thus, preparation of injection medicines based on the temporary injection prescription data may be done at the dispensary as in the case of the ordinary injection prescription data or in the hospital ward.

(C) In the Case of Urgent Injection Prescription

An urgent injection prescription is an injection prescription designating an administration scheduled within three hours. An urgent injection prescription may designate modification of an ordinary injection prescription or a temporary injection prescription. The prescription analyzer 250 acquires injection prescription data from the prescription database 202. If the injection prescription data thus acquired is urgent injection prescription data, the prescription analyzer 250 transmits the urgent injection prescription data to the medicine management apparatus 100 provided in an associated hospital ward. In this case, too, the prescription analyzer 250 causes the medicine management apparatus 100 to print an injection prescription label carrying the particulars of the urgent injection prescription data via the communication network 216. The nurse causes the barcode reader 104 to scan the injection prescription code. The medicine management apparatus 100 acquires the associated urgent injection prescription data from the prescription analyzer 250. The nurse takes medicines out of storage in accordance with the urgent injection prescription data thus acquired. When the retrieval is completed, the medicine management apparatus 100 transmits a retrieval completion signal to the prescription analyzer 250. In the hospital ward, an admixture is prepared from the injection medicines retrieved from the medicine management apparatus 100 and the resultant prepared injection medicine is administered to the patient.

(C) In the Case of Emergency Administration

A change in the patient's condition may require injection medicines be taken out of storage at the discretion of the site of medical care without depending on the injection prescription data. When medicines are retrieved from the medicine management apparatus 100 at the discretion of the site of medical care, emergency retrieval information, indicating the identify of medicines taken out and the use to which they are put, is transmitted to the prescription analyzer 250. Hereinafter, the retrieval of injection medicines for emergency administration will be referred to as "emergency retrieval".

If the scheduled administration time is imminent, as in the case of urgent injection prescription data, the process undertaken at a busy dispensary of preparing necessary injection medicines and transporting them to a hospital ward may be a factor impeding efficient medical care. If urgent injection prescriptions are provided frequently, it impedes standardization of operations in the dispensary, imposing heavy burden on medicine handling personnels.

The dispensary has an entire collection of medicines expected to be used in the hospital 200. The medicine management apparatus 100 accommodates medicines expected to be used in the hospital ward in which the apparatus is provided. Accordingly, injection medicines necessary in emergency administration may often be available in the medicine management apparatus 100. According to the first embodiment, injection medicines can be prepared at the site of medical care, and steps like preparation of admixture and administration can be performed immediately. Thus, the illustrated system will contribute to efficient and accurate medical care.

The same thing is also true of administration of a prepared injection medicine based on the urgent injection prescription data or the temporary injection prescription data. According to the illustrated system, the nurse can prepare necessary injection medicines at the hospital ward, using available time while on duty. Information regarding completion of the retrieval of injection medicines or change in the stock is transmitted from the medicine management apparatus 100 to the prescription analyzer 250 as appropriate. Information acquired by the prescription analyzer 250 from the medicine management apparatus 100 or the input terminal for a dispensary 214 is communicated to the medical information system 220. This enables real-time management by the medical information system 220 of stock status or status of fulfillment of injection prescription throughout the hospital 200. Consequently, reduction of the burden on medicine handling personnels such as nurses and pharmacists is facilitated, and proper allocation of medicines is achieved, thereby improving the quality of medical care and efficiency of hospital services. Specific aspects of the invention will now be described.

Figure 3:
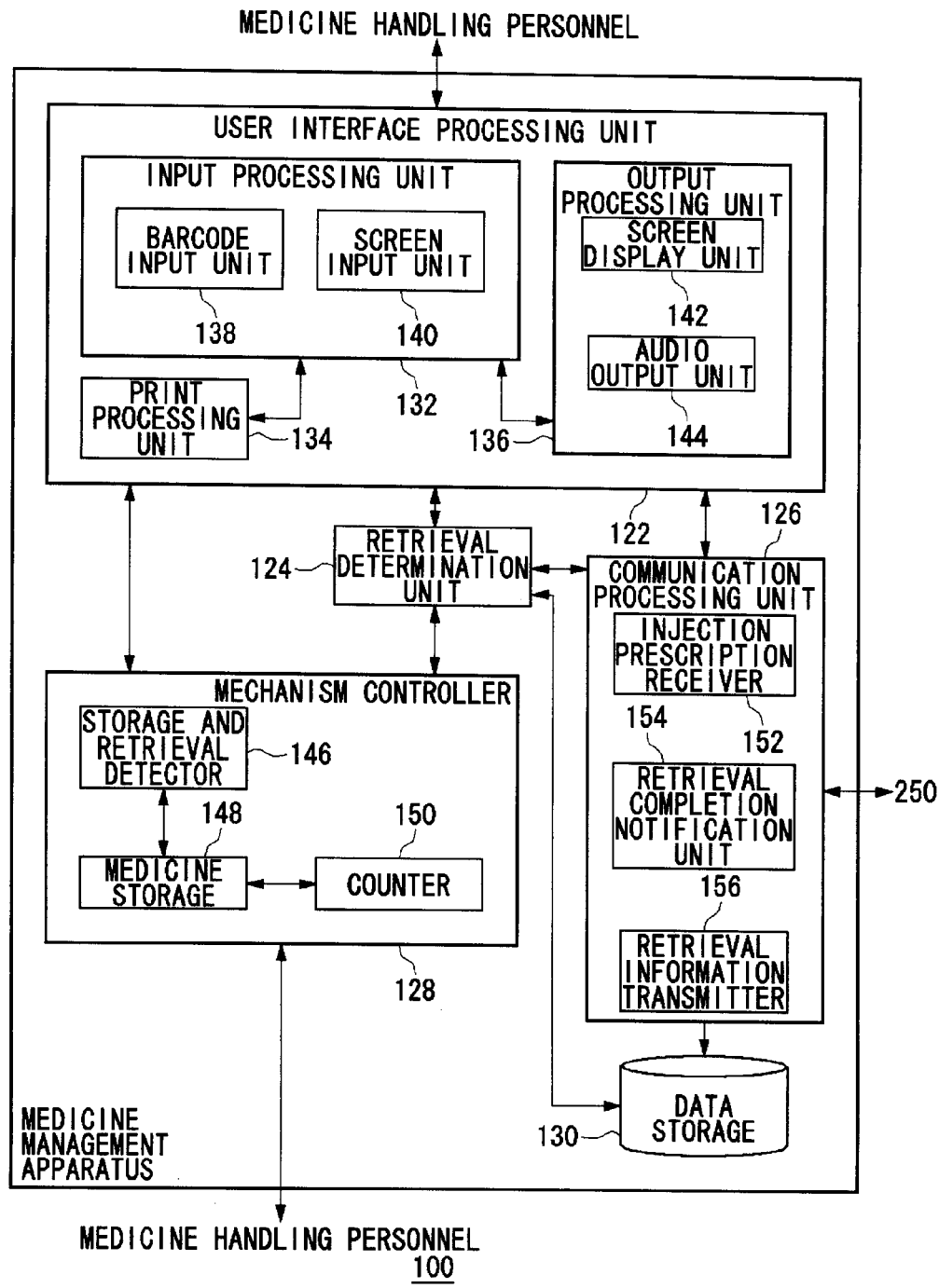
FIG. 3 is a functional block diagram of the medicine management apparatus according to the first embodiment.

FIG. 3 is a functional block diagram of the medicine management apparatus.

The blocks as shown may be implemented hardwarewise by components such as a computer CPU and mechanical devices, and softwarewise by a program such as that for data transmission and reception functions. FIG. 3 depicts functional blocks implemented by cooperation of hardware and software. Therefore, it will be obvious to those skilled in the art that the functional blocks may be implemented in a variety of manners by a combination of hardware and software.

The medicine management apparatus 100 includes a user interface processing unit 122, a retrieval determination unit 124, a communication processing unit 126, a mechanism controller 128 and a data storage 130.

The user interface processing unit 122 is responsible for processes related to the user interface. The user interface processing unit 122 includes an input processing unit 132, a print processing unit 134 and an output processing unit 136. The input processing unit 132 is responsible for processes related to an input from a medicine handling personnel such as a nurse. The input processing unit 132 authenticates the medicine handling personnel and prevents unauthorized access. The input processing unit 132 further includes a barcode input unit 138 and a screen input unit 140. The barcode input unit 138 accepts a barcode input from the barcode reader 104. A barcode may be attached to non-accommodated articles and nurses for identification. The screen input unit 140 accepts a touch-screen input provided by the nurse to the display device 102. The input processing unit 132 may be provided with other input units. For example, the input processing unit 132 may accept an audio input from the nurse.

The output processing unit 136 is responsible for processes related to output of information to the medicine handling personnel. The output processing unit 136 includes a screen display unit 142 and an audio output unit 144. The screen display unit 142 outputs information to the nurse via the display device 102, using the graphic user interface (GUI). The audio output unit 114 provides an audio guidance. The print processing unit 134 performs a printing process in accordance with an instruction from the input processing unit 132 or the prescription analyzer 250.

The mechanism controller 128 is a mechanism for stock control of accommodated medicines. The mechanism controller 128 is a primarily mechanically constituted block and includes a storage and retrieval detector 146, a medicine storing unit 148 and a counter 150. The medicine storing unit 148 is for storing accommodated medicines and is embodied primarily by the medicine storage 106 of FIG. 1. As the nurse manipulates the apparatus for storage or retrieval of accommodated medicines, the storage and retrieval detector 146 detects the storage or retrieval by a known method. The counter 150 counts the number of accommodated medicines of respective types by a known method.

The communication processing unit 126 is responsible for communication with an external device. The communication processing unit 126 further includes an injection prescription receiver 152, a retrieval completion notification unit 154 and a retrieval information transmitter 156. The injection prescription receiver 152 acquires the injection prescription data from the prescription analyzer 250. The retrieval completion notification unit 154 transmits a retrieval completion signal indicating that the retrieval of injection medicines based on the injection prescription data is completed to the prescription analyzer 250. The retrieval information transmitter 156 transmits retrieval information indicating the particulars of retrieved injection medicines to the prescription analyzer 250. The retrieval information includes medicines taken out of storage, the amount of medicines taken out of storage and the purpose of the medicines taken out of storage.

The data storage 130 stores data such as the injection prescription data received by the injection prescription receiver 152. The retrieval determination unit 124 determines whether the injection prescription data received by the injection prescription receiver 152 includes the medicines detected by the storage and retrieval detector 146. Upon detecting an injection medicine not included in the injection prescription data, the retrieval determination unit 124 alerts of unauthorized retrieval via the output processing unit 136.

Figure 4:
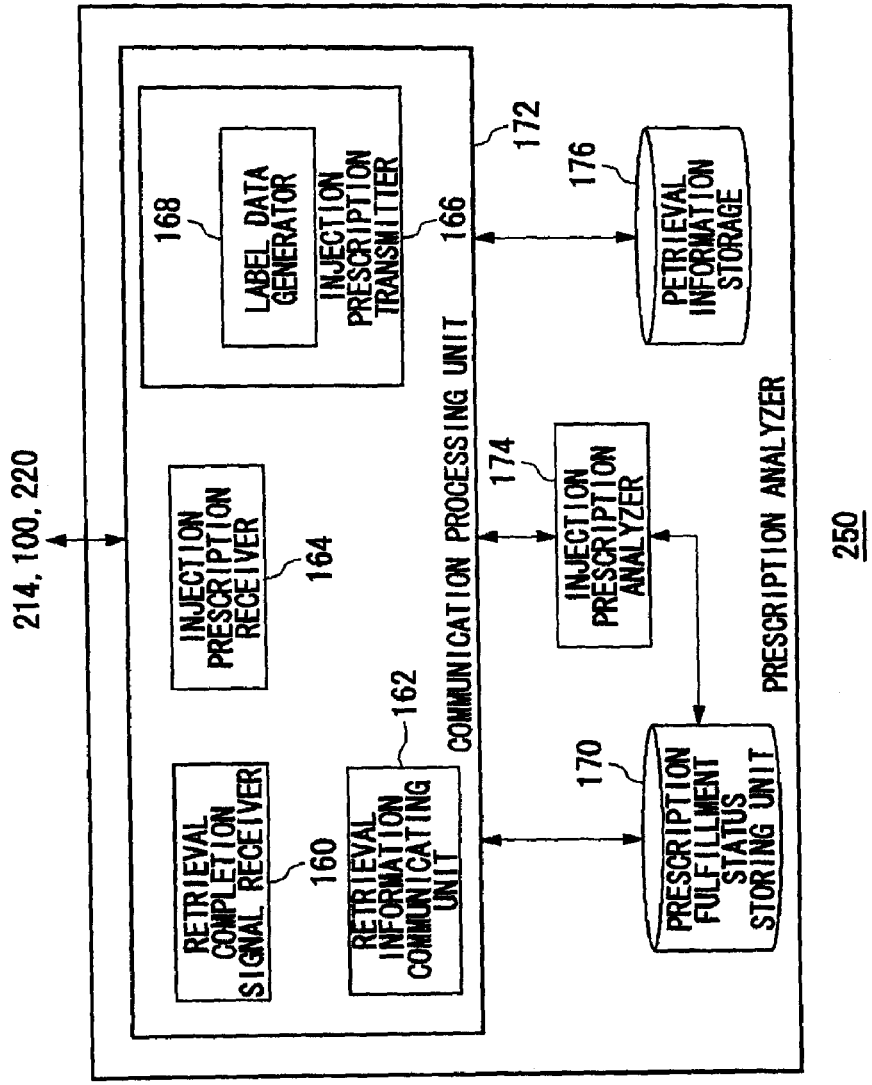
FIG. 4 is a functional block diagram of a prescription analyzer according to the first embodiment.

FIG. 4 is a functional block diagram of the prescription analyzer.

The blocks as shown may be implemented hardwarewise by components such as a computer CPU and mechanical devices, and softwarewise by a program such as that for data transmission and reception functions. FIG. 4 depicts functional blocks implemented by cooperation of hardware and software. Therefore, it will be obvious to those skilled in the art that the functional blocks may be implemented in a variety of manners by a combination of hardware and software.

The prescription analyzer 250 includes a communication processing unit 172, a prescription fulfillment status storage unit 170, an injection prescription analyzer 174 and a retrieval information storage 176.

The communication processing unit 172 is responsible for communication with the medicine management apparatus 100 and the medical information system 220. The communication processing unit 172 includes a retrieval completion signal receiver 160, a retrieval information communicating unit 162, an injection prescription receiver 164 and an injection prescription transmitter 166. The retrieval completion signal receiver 160 receives a retrieval completion signal from the medicine management apparatus 100. The retrieval information communicating unit 162 receives the retrieval information from the medicine management apparatus 100. The injection prescription receiver 164 receives the injection prescription data from the medical information system 220. The injection prescription transmitter 166 transmits the injection prescription data received by the injection prescription receiver 164 to the input terminal for a dispensary 214 or the medicine management apparatus 100. The injection prescription receiver 166 further includes a label data generator 168. The label data generator 168 generates data for printing an injection prescription label in accordance with the injection prescription data. The injection prescription transmitter 166 exercises control so as to cause the network printer connected to the input terminal for a dispensary 214 or the medicine management apparatus 100 to print the injection prescription label.

The injection prescription analyzer 174 analyzes the injection prescription data received from the injection prescription data receiver 164 to determine whether the data designates ordinary, temporary or urgent administration. The injection prescription analyzer 174 identifies a destination of transmission to which the injection prescription transmitter 166 should transmit the injection prescription label data, in accordance with the injection prescription data. The prescription fulfillment status storing unit 170 stores information indicating the status of retrieval of injection medicines based on the injection prescription data received by the injection prescription receiver 164. Upon receiving a retrieval completion signal from the input terminal for a dispensary 214 or the medicine management apparatus 100, the retrieval completion signal receiver 160 updates the prescription fulfillment information.

The retrieval information storage 176 stores retrieval information received by the retrieval information communicating unit 162 from the input terminal for a dispensary 214 or the medicine management apparatus 100. The retrieval information communicating unit 162 transmits the retrieval information stored in the retrieval information storage 176 periodically to the medical information system 220. The stock control system 210 of the medical information system 220 updates information on a stock of medicines maintained in the stock database 204, in accordance with the retrieval information received from the prescription analyzer 250. In accordance with the retrieval information, the medical accounting system 206 gives an instruction to order medicines from outside the hospital 200 in order to replenish medicines in the dispensary or the hospital ward. Information stored in the prescription database 202 is also updated as appropriate depending on the retrieval information.

Figure 5:
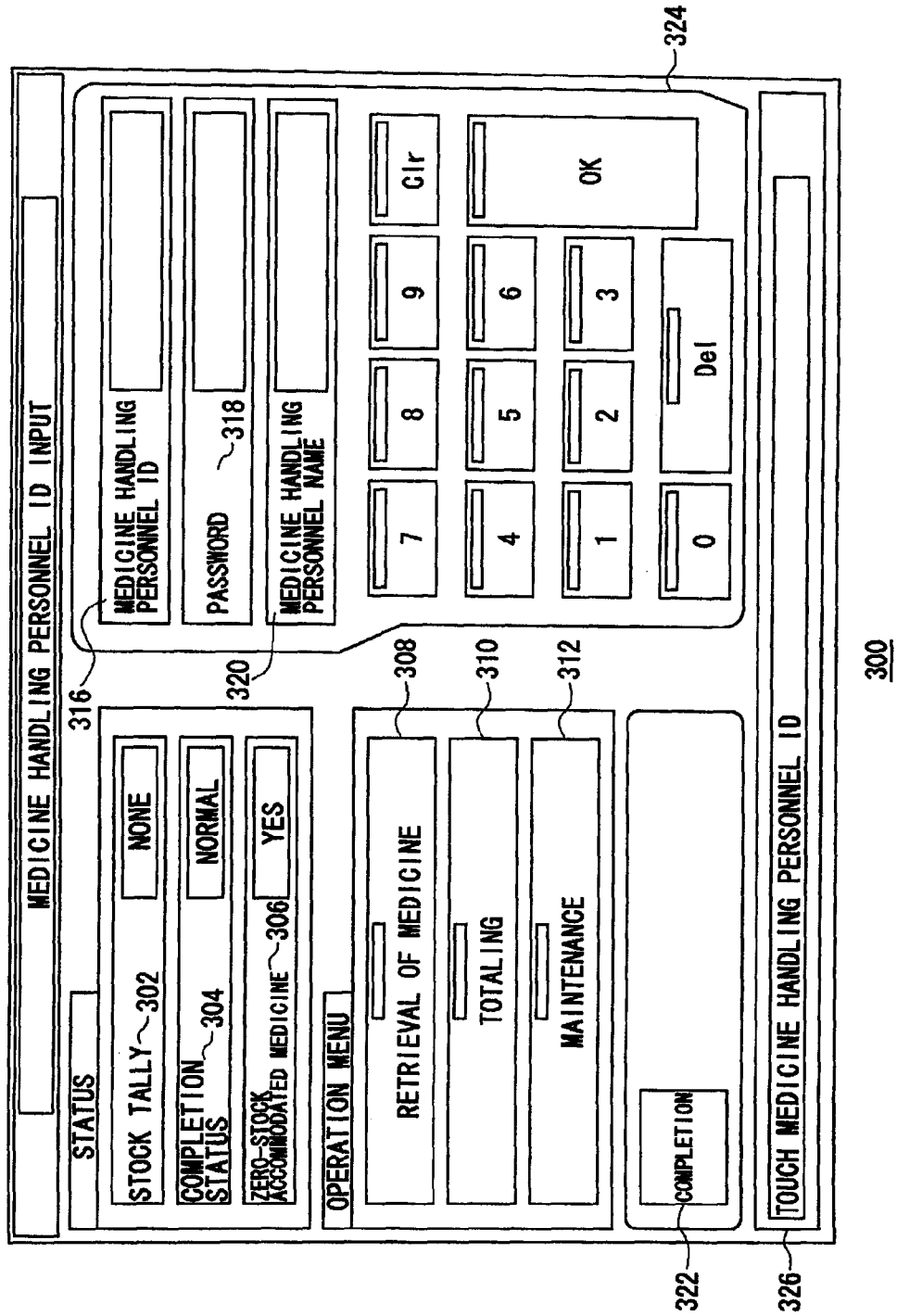
FIG. 5 shows a login screen of the medicine management apparatus according to the first embodiment.

FIG. 5 shows a login screen 300 which is an initial screen of the medicine management apparatus.

In a medicine handling personnel ID input field 316, the nurse enters an ID number which is assigned to each medicine handling personnel (in this, the nurse) and called a medicine handling personnel ID. The nurse also enters a password for authenticating the nurse in a password input field 318. These inputs are provided by touching a ten key 324. Alternatively, the inputs may be provided by using a pre-assigned barcode. If the medicine handling personnel ID and the password are authenticated by the input processing unit 132, a medicine handling personnel name display field 320 displays the name of the nurse, whereupon the nurse is authorized to manipulate the medicine management apparatus 100. Information including the medicine handling personnel ID, password and nurse name are stored in the data storage 130. Alternatively, a database included in the medical information system 220 or the prescription analyzer 250 may store the information.

A stock tally display field 302, a completion status display field 304 and a zero stock display field 306 display information on the status of the medicine management apparatus 100. The stock tally display field 302 displays whether the number of accommodated medicines physically counted by the counter 150 matches the stock of accommodated medicines maintained by the data storage 130 of the medicine management apparatus 100. The retrieval determination unit 124 keeps track of the amount of stock of accommodated medicines by exhaustively recording information on the storage and retrieval of accommodated medicines in the data storage 130. The amount of stock of accommodated medicines is physically counted by the counter 150. Normally, the count and the information match but may not match due to an error that occurs in the process or a mechanical failure. If the stock tally display field 302 displays "matching failure", a problem like these is occurring. In this way, an error related to the counting of accommodated medicines is immediately detected.

Since the accommodated medicines usually include expensive medicines, early detection of a mistake in management due to an error in the process performed by the medicine management apparatus 100 is important. The completion status display field 304 displays whether the medicine management apparatus 100 is turned off normally in the previous use. If the system was not terminated normally, it is indicated as such. The zero stock display field 306 displays whether any type of accommodated medicine has run out of storage.

A medicine retrieval operation button 308, a totaling operation button 310 and a maintenance operation button 312 are a group of buttons corresponding to operations that should be performed by the nurse. The medicine retrieval operation button 308 is a button for displaying a screen for operations of storage and retrieval of medicines. The screen will be explained with reference to FIG. 6. The totaling operation button 310 is a button for displaying a screen (not shown) for a totaling operation. The maintenance operation button 312 is a button for displaying a screen (not shown) for maintenance of the medicine management apparatus 100. When a completion button 322 is touched, the process of the medicine management apparatus 100 is terminated. An input information display field 326 displays guidance regarding the input operation.

Figure 6:
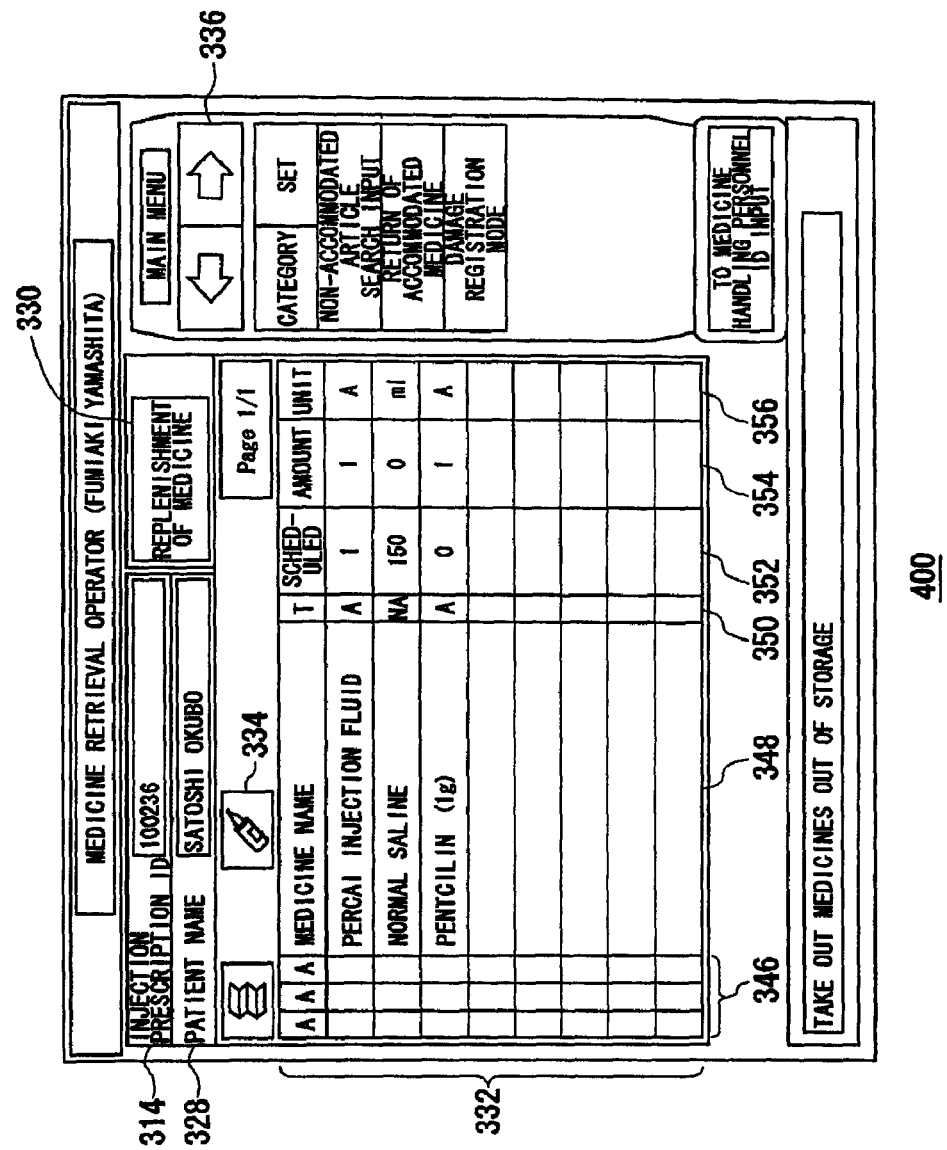
FIG. 6 shows a medicine retrieval operation screen of the medicine management apparatus according to the first embodiment.

When the login is successful and the medicine retrieval operation button 308 is touched, a screen is displayed, prompting the drug handling personnel to input an injection prescription code. When the medicine handling personnel causes the barcode reader 104 to scan the injection prescription code, the injection prescription receiver 152 acquires the injection prescription data via the injection prescription transmitter 166. The screen display unit 142 displays the injection prescription data thus acquired in the display device 102. FIG. 6 shows how the data is displayed.

FIG. 6 shows a medicine retrieval operation screen for medicine retrieval operations displayed after the injection prescription data is displayed.

When the medicine handling personnel causes the barcode reader 104 to scan the injection prescription code, the input processing unit 132 directs the injection prescription receiver 152 to request the injection prescription data from the prescription analyzer 250. Upon receiving the request, the communication processing unit 172 of the prescription analyzer 250 reads the associated injection prescription data from the prescription fulfillment status storing unit 170. The injection prescription transmitter 166 transmits the injection prescription data to the medicine management apparatus 100. An injection prescription ID field 314 in the medicine retrieval operation screen 400 displays the injection prescription ID corresponding to the injection prescription data. A patient name display field 328 displays the name of the patient.

If the injection prescription data has not been scanned, i.e., in the case of emergency administration, the injection prescription ID field 314 and the patient name display field 328 are empty. Even in the case of emergency administration, the medicine handling personnel may cause the barcode reader 104 to scan a barcode corresponding to the patient ID assigned to the patient for unique identification (hereinafter, referred to as a "patient code"). In this process, the communication processing unit 126 acquires the patient's name corresponding to the patient code from the patient database 218 via the prescription analyzer 250. The screen display unit 142 displays the name of the patient thus retrieved in the patient name display field 328. A medicine replenishing button 330 is a button for displaying a screen (not shown) to manage replenishment of accommodated medicines. A page switching button 336 is a button operated to switch between pages if the medicines viewed in a storage and retrieval display field 332 fail to be displayed in a single screen.

The storage and retrieval display area 332 displays information related to injection medicines to be stored or retrieved. An alert field 346 displays an alert assigned to each injection medicine. Some injection medicines require special care in handling for reasons of high prices or danger. The nurse is allowed to configure an alert for each of the injection medicines. An alert thus configured is displayed in the alert field 346. There are three columns for alerts in the alert field 346 which correspond to the levels of alert, i.e., the importance of alerts. More important alerts are displayed toward the right.

A medicine name field 348 displays the name of the injection medicine handled. Information such as the specification of the injection medicine may be displayed in addition to the name of the injection medicine. A type field 350 displays the type of the injection medicine, i.e., distinction between an accommodated medicine and a non-accommodated article. A retrieval schedule field 352 displays the volume scheduled to be taken out of storage as designated in the injection prescription data. The volume actually taken out of storage is displayed in a retrieved volume field 354. A unit of retrieval field 356 displays the unit of retrieval of the injection medicine.

The figure shows that the injection medicine designated in the injection prescription with the injection prescription ID "100236" should be administered to a patient named "Satoshi Okubo". The injection prescription data prescribes that one ampule (A) of Percami (provisional name), which is an accommodated medicine, and 150 mililiter (ml) of normal saline, which is a non-accommodated article, be taken out of storage. The figure shows that one ampule of Percami (provisional name) and one ampule of Pentcilin (1 g) (provisional name) are taken out of storage. For brevity, the medicines may be indicated by their provisional names.

Since normal saline prescribed in the injection prescription data has not been taken out of storage, the storage and retrieval display area 332 prompts for retrieval of normal saline. For example, the screen display unit 142 may alert the medicine handling personnel by displaying the row displaying normal saline with a color different from the other rows, in accordance with an instruction from the retrieval determination unit 124. The audio output unit 144 may alert the medicine handling personnel in accordance with the instruction from the retrieval determination unit 124, by giving a direct instruction such as audio guidance prompting the personnel to take out normal saline out of storage.

When taking out normal saline, which is a non-accommodated article, the nurse informs the medicine management apparatus 100 of the retrieval, by allowing the barcode reader 104 to scan a barcode (hereinafter, referred to as medicine code) assigned to normal saline. When the barcode input unit 138 accepts an input for storage or retrieval, or when the storage and retrieval detector 146 detects storage or retrieval, the screen display unit 142 updates screen information on a real-time basis. With this, the nurse can know the result of storage or retrieval operation in a timely manner.

Although the injection prescription data does not designate the retrieval of Pentcilin (1 g) (provisional name), which is an accommodated medicine, the medicine handling personnel has taken out Pentcilin (1 g) (provisional name). The retrieval determination unit 124 determines the retrieval of an injection medicine not based upon the injection prescription data such as this as being unauthorized retrieval. The retrieval determination unit 124 directs the screen display unit 142 to notify the medicine handling personnel that unauthorized retrieval has taken place. For example, the screen display unit 142 may display the row displaying Pentcilin (1 g) (provisional name) with a color different from the other rows. Alternatively, the audio output unit 144 may provide an audio notification to the medicine handling personnel that unauthorized retrieval has taken place, in accordance with an instruction from the retrieval determination unit 124.

Thus, the medicine management apparatus 100 graphically displays the status of retrieval and alerts of unauthorized retrieval or insufficient retrieval, based upon the injection prescription data. In this way, the nurse is significantly relieved of the burden of checkup when preparing medicines based on the injection prescription data.

FIG. 7 shows a retrieval review screen displayed after the injection medicines have been taken out of storage in accordance with the injection prescription data.

An invoice field 362 in a retrieval review screen 360 displays the particulars of the injection prescription data. As shown in the figure, the injection prescription ID, patient's name, name of the doctor who issued the injection prescription and the like are displayed in the invoice field 362. The print processing unit 134 prints the particulars shown in the invoice field 362 as a retrieval slip. A retrieval review field 364 displays a list of the injection medicines designated by the injection prescription data to be retrieved and the injection medicines actually taken out of storage (retrieved). The nurse examines what is displayed in the retrieval review field 364 for final checkup of the particulars of the retrieval. When the retrieval is completed, the retrieval completion notification unit 154 transmits a retrieval completion signal to the prescription analyzer 250. Upon receipt of the retrieval completion signal, the retrieval completion signal receiver 160 of the prescription analyzer 250 updates the prescription fulfillment status stored in the prescription fulfillment status storing unit 170.

In the case of urgent injection prescription data, the prescription analyzer 250 transmits the urgent injection prescription data to the medicine management apparatus 100 provided in an associated hospital ward. In the case of temporary injection prescription data, the prescription analyzer 250 transmits the temporary injection prescription data to the input terminal at a dispensary 214. In advance of this step, the nurse may retrieve injection medicines from the medicine management apparatus 100, based on the temporary injection prescription data.

FIG. 8 shows an injection prescription list display screen displaying prescription fulfillment status maintained in the prescription analyzer 250.

The prescription analyzer 250 makes accessible the prescription fulfillment status stored in the prescription fulfillment status storing unit 170 via the communication network 216. Aside from the medicine management apparatus 100, communication terminals connected to the communication network 216, such as the input terminal for a dispensary 214, are capable of displaying the prescription fulfillment status maintained in the prescription analyzer 250 on a browser in a manner as shown in an injection prescription list screen 402.

A start date and time input field 422 and an end date and time input field 404 display a time period selected for display. The injection prescription data designating administration during a period of time starting at the date and time entered in the start date and time input field 422 and ending at the date and time entered in the end date and time input field 404 is selected for display. A ward display field 406 displays the ward at which the administration should take place. The figure shows a list of injection prescription data designating administration in the ward "6A" on Dec. 15, 2003.

An injection prescription ID field 408 displays then injection prescription ID. An issuance date and time field 410 displays the date and time that the injection prescription is issued. In this field, the date and time that the injection prescription data is input at the injection prescription input terminal 212 may be entered. In the case of injection prescription data for a prepared injection medicine administered on a regular basis, the medical information system 220 may issue the data on a regular basis unless a change is designated. An administration date and time field 412 displays the date and time for administration. A retrieval completion field 414 displays whether the retrieval of the injection medicine based on the injection prescription data is completed. A category field 416 displays the category of the injection prescription data. In the figure, distinction between an urgent injection prescription and a temporary injection prescription is shown. Alternatively, indication of an ordinary injection prescription may be shown. "Urgent return" indicates modifying injection prescription data designating that some of injection medicines directed to be retrieved by the injection prescription data already issued be returned. Similarly, "urgent addition" indicates modifying injection prescription data designating that additional injection medicines be retrieved in addition to the injection medicines directed to be retrieved by the injection prescription data already issued. A patient ID field 418 displays the patient ID. A patient name field 420 displays the name of the patient. The medicine handling personnel can display further details of the injection prescription data by selecting the injection prescription data displayed, using an input means such as a mouse.

Of the injection prescription data displayed, the medicine handling personnel acquires the injection prescription data not identified to be fulfilled in the retrieval completion field 414. For example, the injection prescription data with the injection prescription ID "100263" is temporary injection prescription data. This injection prescription data designates administration on Dec. 15, 2003. Normally, as described in (B-1) above, the prescription analyzer 250 transmits this injection prescription data to the input terminal for a dispensary 214 during the preparation hours scheduled at the dispensary. At the dispensary, the medicine handling personnel prepares the injection medicines in accordance with the injection prescription data thus transmitted. The injection medicines thus prepared are transported to the hospital ward "6A" by 20:00 on Dec. 15, 2003, the scheduled administration time.

If the nurse in the hospital ward 6A has time to spare, the nurse may download the injection prescription data from the prescription analyzer 250 to the medicine management apparatus 100. When the nurse have taken the injection medicines out of storage on the basis of the injection prescription data, the medicine management apparatus 100 transmits a retrieval completion signal to the prescription analyzer 250. Upon receipt of the retrieval completion signal, the retrieval completion signal receiver 160 of the prescription analyzer 250 updates the prescription fulfillment status in the prescription fulfillment status storing unit 170. In this process, the entry in the retrieval completion field 414 for the injection prescription data with the injection prescription ID "100263" is changed to indicate that the retrieval has been completed. Further, the prescription analyzer 250 no longer transmits this injection prescription data to the input terminal for a dispensary 214. With this, a balance is established, in respect of the burden of handling temporary injection prescription data, between the operation in the dispensary and the operation in the hospital ward.

Figure 9:
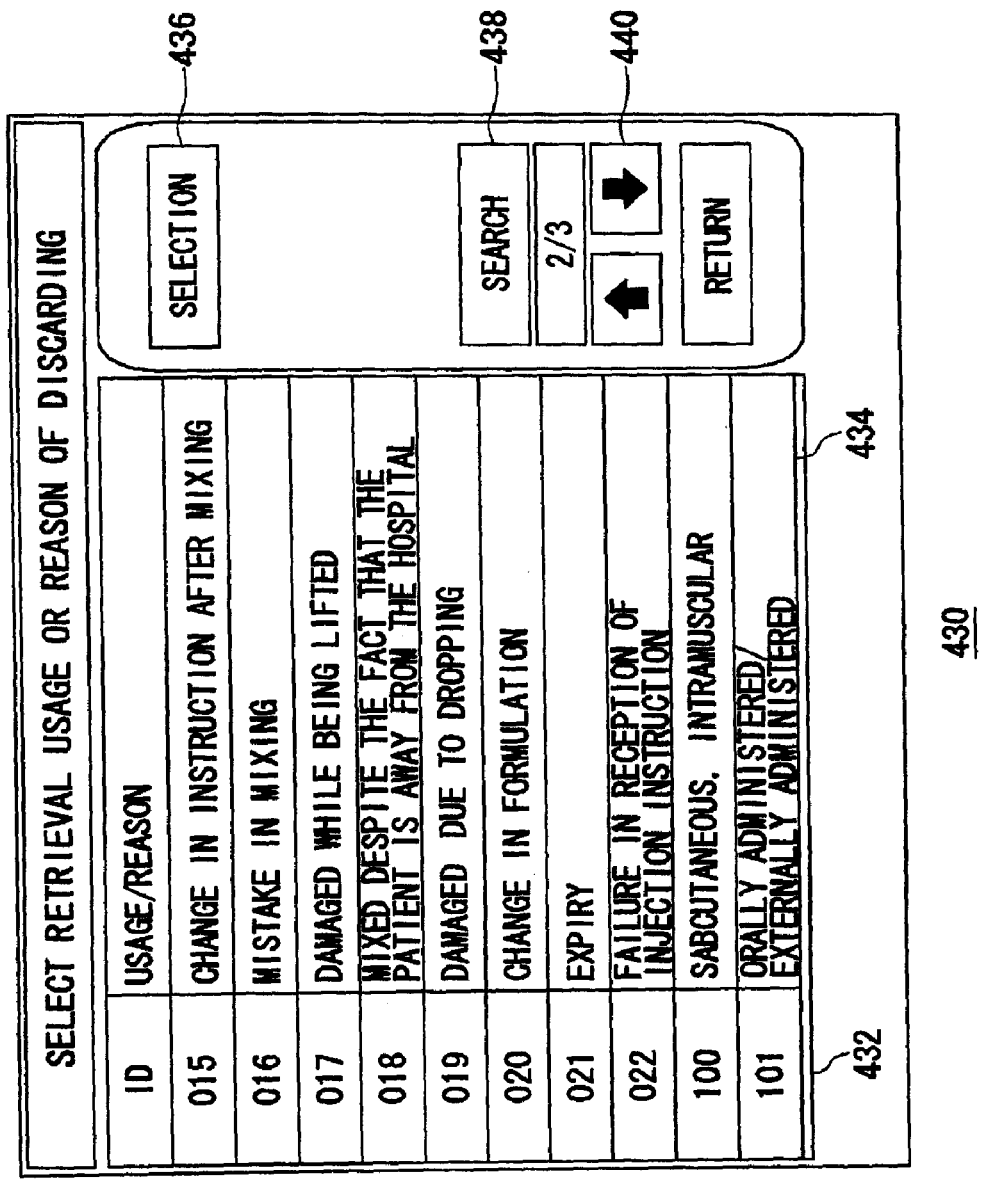
FIG. 9 shows a retrieval usage input screen displayed when a medicine handling personnel takes an injection medicine out of storage for emergency administration.

FIG. 9 shows a retrieval usage input screen displayed when the medicine handling personnel takes an injection medicine out of storage for emergency administration.

Usually, the medicine handling personnel uses the barcode reader 104 to scan the injection prescription code carried in the injection prescription label and transmitted from the prescription analyzer 250, and starts retrieving the injection medicine. Alternatively, the medicine handling personnel may retrieve an injection medicine without depending on injection prescription data. The retrieval usage input screen 430 is shown when the medicine handling personnel takes an injection medicine out of storage for emergency administration. A retrieval usage ID field 432 is for entering the usage or purpose of the medicine retrieved.

The retrieval usage ID field 432 displays a retrieval usage ID uniquely identifying the usage or purpose for retrieval registered in the data storage 130. A retrieval usage name field 434 displays itemized usages of retrieval. In emergency retrieval not based upon injection prescription data, the medicine handling personnel selects one of these usages of retrieval. When the medicine handling personnel touches a selection button 436, selection is confirmed. When a search button 438 is touched, a screen (not shown) is displayed to search for a retrieval usage, using a retrieval usage ID or a text as a key. Touching a page switching button 440 invokes switching between displayed pages.

For example, the retrieval usage data identified by the retrieval usage ID "100" indicates retrieval for subcutaneous injection or intramuscular injection to a patient. The retrieval usage input screen 430 may be displayed not only in the event of emergency retrieval but also in retrieval based upon injection prescription data. For example, modification to injection prescription data may be designated when the injection medicine prepared in accordance with the injection prescription data is damaged. The injection prescription data may also be modified after the prepared injection medicine is produced. In this case, too, the nurse may register the usage of the injection medicine which is once retrieved and can no longer be returned. This prevents failure of knowing the usage of injection medicines from occurring. Information input in the retrieval usage input screen 430 is reflected in the retrieval information transmitted from the retrieval information transmitter 156 to the prescription analyzer 250.

Figure 10:
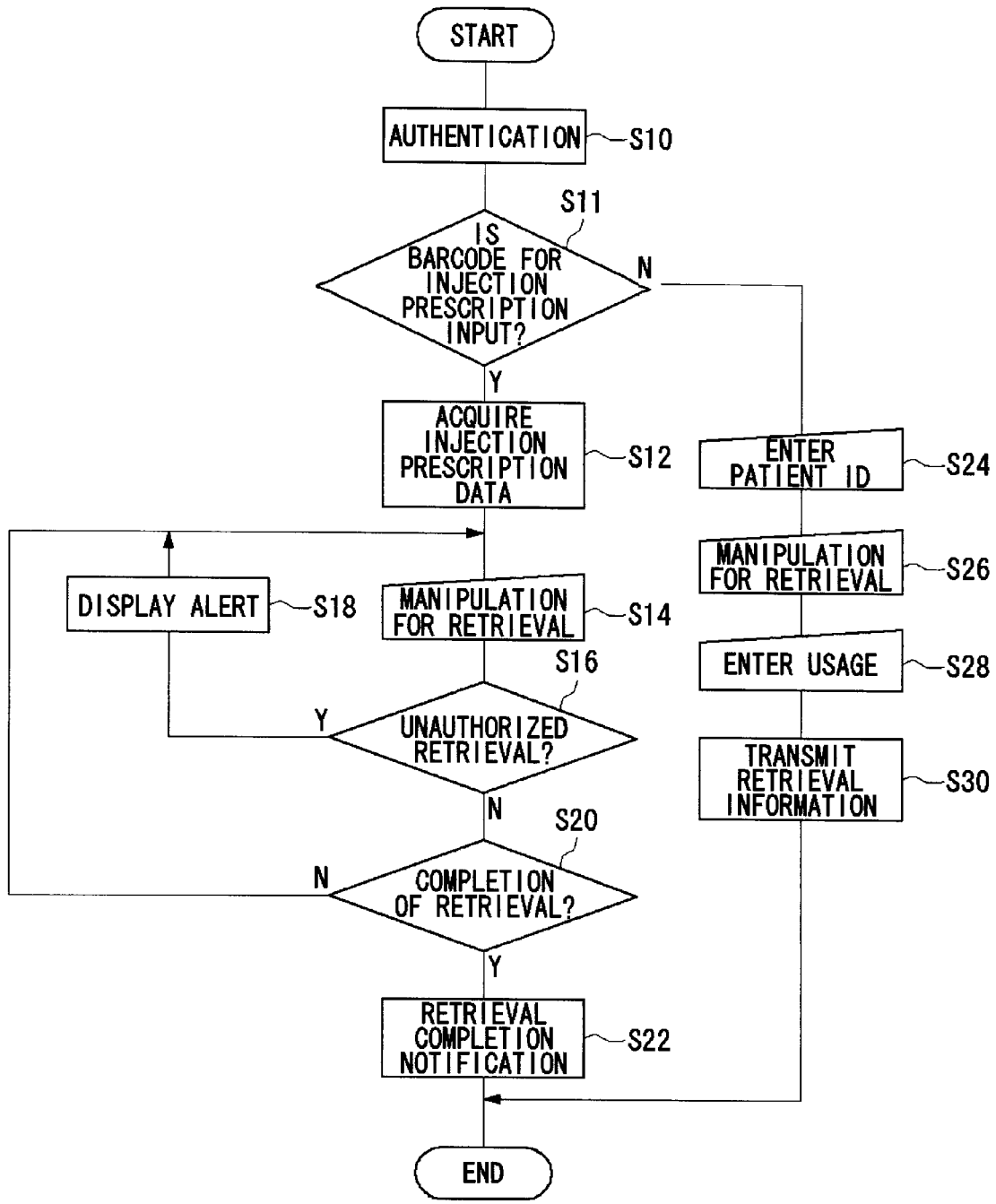
FIG. 10 is a flowchart showing the overall process of retrieving medicines from the medicine management apparatus according to the first embodiment.

FIG. 10 is a flowchart showing the overall process of retrieving medicines from the medicine management apparatus.

Initially, the nurse enters the medicine handling personnel ID and the password in a login screen 300. The input processing unit 132 performs authentication based upon the input information (S10). If authentication fails, the process is not started. When authentication is successful, the screen display unit 142 prompts for entry of an injection prescription code. The input processing unit 132 determines whether the injection prescription code is entered (S11). If the code is entered (Y in S11), the injection prescription receiver 152 acquires the corresponding injection prescription data from the prescription analyzer 250 (S12). The medicine handling personnel retrieves the injection medicine in accordance with an instruction for retrieval displayed on the display device 102 (S14). If the retrieval determination unit 124 detects unauthorized retrieval (Y in S16), the screen display unit 142 displays an alert on the screen (S18). Control is then returned to S14. If unauthorized retrieval is not detected (S16), the retrieval determination unit 124 determines whether the retrieval of the injection medicine based on the injection prescription data is completed (S20).

If the retrieval is not completed (N in S20), control is returned to S14. If the retrieval is completed (Y in S20), the medicine handling personnel examines the particulars of retrieval on the retrieval review screen 360 and confirms the retrieval. When the retrieval is confirmed, the retrieval completion notification unit 154 transmits a retrieval completion signal to the prescription analyzer 250 (S22). In addition, the retrieval information transmitter 156 transmits retrieval information to the prescription analyzer 250. Upon receipt of the retrieval completion signal and the retrieval information, the prescription analyzer 250 updates the prescription fulfillment status stored in the prescription fulfillment status storing unit 170 and the retrieval information stored in the retrieval information storage 176. Further, by receiving the information from the prescription analyzer 250, the medical information system 220 updates information on the status of prescription and stock of medicines.

In the event of emergency retrieval, i.e., when the injection prescription code is not entered in S11 (N in S11), the nurse enters the patient's ID (S24). The nurse retrieves injection medicines necessary for emergency administration (S26). After the retrieval, the nurse enters the usage of retrieved medicine in the retrieval usage input screen 430 (S28). The retrieval information transmitter 156 transmits to the prescription analyzer 250 the retrieval information, which relates the retrieved medicine to the retrieval usage and the patient's ID that are input (S30). By receiving the retrieval information, the prescription analyzer 250 updates the retrieval information stored in the retrieval information storage 176. By receiving the retrieval information from the prescription analyzer 250, the medical information system 220 updates information on the stock of medicines.

Figure 11:
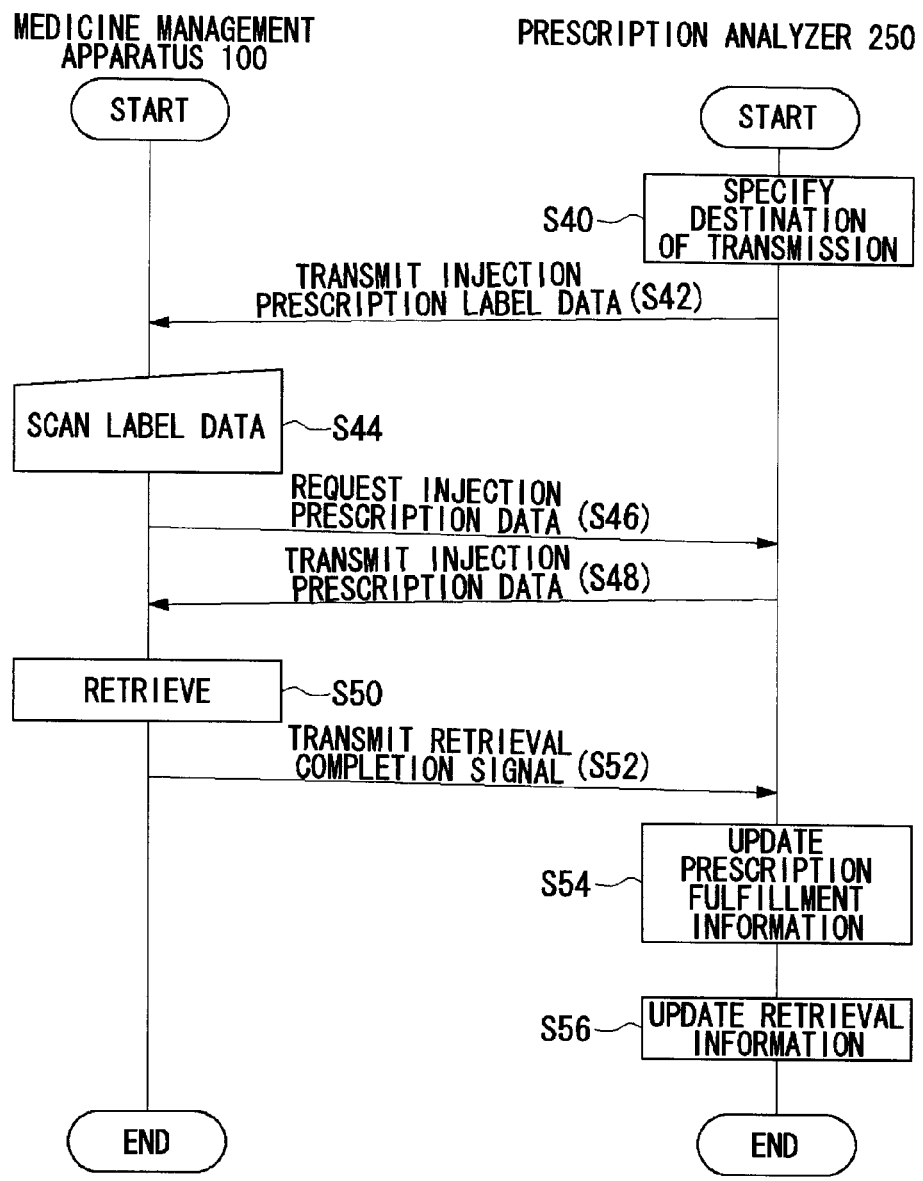
FIG. 11 is a sequence diagram showing the process of retrieving injection medicines in accordance with the injection prescription data.

FIG. 11 is a sequence diagram showing the process of retrieving injection medicines in accordance with urgent injection prescription data.

The prescription analyzer 250 acquires the injection prescription data from the medical information system 220. When the injection prescription analyzer 174 determines that the injection prescription data thus acquired is urgent injection prescription data, the illustrated sequence is started. The injection prescription analyzer 174 specifies the medicine management apparatus 100 provided in the hospital ward associated with the urgent injection prescription data as a destination of transmission (S40). The label data generator 168 generates label data corresponding to the urgent injection prescription data, and the injection prescription transmitter 166 directs the print processing unit 134 to print the label data (S42).

In the associated hospital ward, the nurse uses the barcode reader 104 to scan the injection prescription data carried in the injection prescription label (S44). The communication processing unit 126 requests the injection prescription data corresponding to the injection prescription code from the prescription analyzer 250 (S46). In response to the request, the injection prescription transmitter 166 transmits the injection prescription data to the medicine management apparatus 100 (S48). The injection prescription data is displayed on the display device 102. The nurse in the hospital ward retrieves the injection medicine in accordance with the direction displayed on the screen (S50). When the retrieval is complete, the retrieval completion notification unit 154 transmits a retrieval completion signal to the prescription analyzer 250 (S52). In this process, the retrieval information transmitter 156 also transmits the retrieval information on the retrieved injection medicine to the prescription analyzer 250.

Upon receipt of the retrieval completion signal, the retrieval completion signal receiver 160 of the prescription analyzer 250 updates the prescription fulfillment status in the prescription fulfillment storing unit 170 (S54). Further, the retrieval information communicating unit 162 receiving the retrieval information updates the retrieval information in the retrieval information storage 176 (S56). The prescription fulfillment information and the retrieval information maintained in the prescription analyzer 250 are transmitted to the medical information system 220 as necessary. The medical information system 220 performs stock control of medicines, prescription management, billing procedures and the like, on the basis of the information acquired from at least one prescription analyzer 250.

The medicine management system shown in FIG. 2 including the medicine management apparatus 100 according to the first embodiment is effective in preventing medical malpractice and improving efficiency of hospital operations, and eventually in making hospital management more efficient. This is because medicines are kept at distributed locations, while the medical information system 220 is not only fully capable of managing the storage and retrieval of medicines but also the usage thereof. As the system relieves the medicine handling personnel of the burden of preparation, checkup and administration of medicines and possibly eliminates the task of transporting medicines to a hospital ward, the process ranging from preparation of the injection prescription to the administration of the prepared injection medicine is considerably simplified. The medicine management apparatus 100 according to the embodiment is applicable to the process of administering a prepared injection medicine based on an ordinary injection prescription as well as to the process of administering a prepared injection medicine based on an urgent injection prescription or a temporary injection prescription. According to the embodiment, there is no need for central management of the stock of medicines at a dispensary, thereby enabling more efficient use of the space in a hospital. As described in connection with temporary injection prescription data, the nurse in the hospital ward can shoulder the burden of some of the tasks imposed on a pharmacist in the dispensary, the inventive system is also effective in leveling the burden of operations among the medical staff. Such optimization of the usage of human and physical resources is conductive to the reduction of burden on the medical staff and also helps improve not only the quality of medical services but also the efficiency of hospital management.

Described above is an explanation of the first embodiment based on the illustrative example. The embodiment is only illustrative in nature and it will be obvious to those skilled in the art that variations in constituting elements and processes are possible and that such variations are also within the scope of the present invention. While the first embodiment is described by taking the injection medicine as an example, it goes without saying that the present invention is equally applicable to medicines and medical resources in general used at a site of medical care. The ordinary injection prescription, temporary injection prescription and urgent injection prescription may be defined in accordance with the operation regarding the injection prescription undertaken at a site of medical care. For example, the ordinary injection prescription may be defined as being issued on a day before the date of administration and the temporary injection prescription may be defined as being re-issued on a previous day or issued on the date of administration. That the administration is urgent may be indicated by the doctor in the emergency injection prescription.

(Second Embodiment)

The second embodiment also relates to a technology for managing medicines used at a site of medical care and, more particularly, to a technology for stock control of medicines.

At a site of medical care such as an operation room, a medicine handling personnel like a nurse or a pharmacist prepares medicines such as injection medicines and infusion fluids before a medical treatment. Usually, extra supply of medicines are prepared to prevent shortage of medicines.

Medicines actually used are listed in a bill by referring to the container discarded after the operation or manually input to a computer. Billing for medicines used and stock control are undertaken in hospitals as described above. As a result, the burden of billing for medicines and stock control is so serious that hospitals have had to secure more medicines in stock than necessary in order to prevent shortage of stock of medicines.

In this background, there are a variety of proposals for stock control of medicines used at a site of medical care. An example of such proposal is an apparatus capable of accommodating medicines automatically detecting the storage and retrieval of medicines accommodated. The apparatus is designed to automatically detect the storage and retrieval by a medicine handling personnel of medicines accommodated in the apparatus. Since such an apparatus is configured to count the accommodated medicines for management, it is successful at least in saving much labor in management of medicines accommodated within the apparatus (see, for example, patent documents 7 and 8).

Meanwhile, some of the large hospitals are introducing a system for overall management of medical services in accordance with instructions from the doctors (hereinafter, referred to as a medical information system). The medical information system is for central handling of information on: management of patient information; reservation of operations; ordering of medicines; logistics; electronic patient charts; prescription management; medical accounting; and stock of medicines in a hospital. The functions that should be provided in the medical information system vary from hospital to hospital, but it remains a system for management of information on medical services. In order to operate the medical information system efficiently, it is important to recognize the status of use of medicines at a site of medical care accurately and immediately. Particularly, it is extremely important to control the stock of medicines on the basis of accurate on-site information.

While the aforementioned apparatus saves much labor in management, it may not necessarily be suitable for managing medicines in an entire hospital. Meanwhile, if the medicine stock control capabilities of the apparatus can be taken advantage in the medical information system, more efficient medical services can be expected. Another background fact is that human errors often directly lead to mishaps in medical practice. At a site of medical care, reducing human errors associated with medicine management is also a particularly important task.

A summary of the second embodiment will be given.

The medicine management apparatus according to the second embodiment comprises: a medicine storage which stores a plurality of medicines used at a site of medical care; a detecting mechanism which, when a medicine handling personnel manipulates the apparatus to store or retrieve an accommodated medicine to be accommodated in the apparatus, physically detects the target accommodated medicine for which the apparatus is manipulated, differentiating it from the other accommodated medicines; and an accommodated medicine counter which counts each type of the plurality of accommodated medicines, the medicine management apparatus further comprising: a stored or retrieved accommodated medicine information recorder which records, on a recording medium, stored or retrieved accommodated medicine information which relates to accommodated medicines that are stored or retrieved; a display unit which at least displays the stored or retrieved accommodated medicine information; a format converter which converts the format in order to allow an external database to store at least retrieved accommodated medicine information related to retrieval, which information constitutes the stored or retrieved accommodated medicine information; a communicating unit which transmits the retrieved accommodated medicine information thus converted to the database; and a controller which at least controls the stored or retrieved medicine information recorder, the display unit, the format converter and the communicating unit in an integrated manner.

In the second embodiment, the term "accommodated medicines" refers to drugs and medicines, including those dissolved before use, which are accommodated in a medicine storage. The term "non-accommodated articles", which will be mentioned later, pertains to a notion opposite to "accommodated medicines" and encompass medicines and drugs that are not accommodated in the medicine storage. Hereinafter, accommodated medicines and non-accommodated articles are collectively referred to as "medicines". The collective term "medicines" may also be applied to medical resources and infusion fluids. Normally, medical resources are consumable supplies. The term "recording medium" refers not only to a fixed recording medium such as a hard disk and a floppy disk but also to a temporary storage medium such as a dynamic random access memory (DRAM).

According to the second embodiment, an external database can easily collect retrieved accommodated medicine information from multiple medicine management apparatuses. This will help, for example, the aforementioned medical information system, to easily know the stock status of medicines in an entire hospital.

The medicine management apparatus may comprise: a stored or retrieved non-accommodated article input unit which, when a medicine handling personnel stores or retrieves a non-accommodated article not stored in the medicine storage, accepts an input regarding the non-accommodated article stored or retrieved; and a stored or retrieved non-accommodated article information recorder which records, on a recording medium, stored or retrieved non-accommodated article information which relates to non-accommodated articles that are stored or retrieved.

The communicating unit may transmit information related to the retrieval of non-accommodated article to the external database. By accepting an input regarding articles other than the accommodated medicines, the apparatus is capable of managing medicines of forms that cannot be stored in the medicine storage.

The medicine management apparatus may further comprise a movable seat on which the apparatus main body is installed.

The term "movable seat" refers to seat equipment such as a cart for moving the medicine management apparatus itself. By ensuring that the medicine management apparatus is movable, the apparatus can easily be installed at a place where medicine management is required.

When a detecting mechanism detects a manipulation for storing or retrieving an accommodated medicine, the controller may display the name of the accommodated medicine thus handled on a display unit on a real time basis.

As the medicine handling personnel manipulates the apparatus to store or retrieve an accommodated medicine, the medicine handling personnel can immediately know, by viewing the display unit, whether the accommodated medicine stored or retrieved is the desired accommodated medicine. This is useful in preventing a mistake in storage or retrieval of accommodated medicines by the medicine handling personnel. The medicine handling personnel may be notified of the name of the accommodated medicine retrieved by sound.

The medicine management apparatus may further comprise a non-accommodated article identification information detector which reads non-accommodated article identification information assigned to the non-accommodated articles, and the stored or retrieved non-accommodated article input unit may accept the input by allowing the non-accommodated article identification information detector to read the non-accommodated article identification information.

The term "non-accommodated article identification information" refers to information such as identification numbers and barcodes for uniquely identifying the non-accommodated articles. The information may be identification information that complies with a standard such as Japan Article Number (JAN). Alternatively, the information may be identification information locally configured in a hospital. The "non-accommodated article identification information detector" may be, for example, a barcode reader. The detector facilitates the input of storage and retrieval of non-accommodated articles.

The medicine management apparatus may further comprise: a medicine handling personnel ID recorder which records a medicine handling personnel ID, assigned to identify the medicine handling personnel, on a recording medium; and a medicine handling personnel ID input unit which accepts an input of the medicine handling personnel ID, wherein the communicating unit may be further provided with the function of receiving patient information from an external database which stores the patient information, and the stored or retrieved accommodated medicine information recorder may record the stored or retrieved accommodated medicine information based upon the medicine handling personnel ID associated with the medicine handling personnel who manipulated the apparatus to store or retrieve the medicine, and upon the patient information received.

By recording the stored or retrieved accommodated medicine information in association with the identity of the medicine handling personnel and with the patient for which the accommodated medicine is stored or retrieved, the status of storage and retrieval of medicines can be recognized more accurately. In the case of relatively high-priced accommodated medicines, the advantage of enhanced security will also be enjoyed because the manipulation performed by the medicine handling personnel for storage or retrieval is recorded. The record is also useful in follow-up tracking of the status of use of accommodated medicines stored or retrieved. By managing storage and retrieval on the basis of the medicine handling personnel ID and the patient information not only in the case of accommodated medicines but also in the case of non-accommodated articles, the aforementioned advantages are available in handling non-accommodated articles as well.

The stored or retrieved accommodated medicine information recorder may further be provided with at least one of the function of recording replenishment history information which relates to replenishment of accommodated medicines, and the function of recording use history information related to accommodated medicines used in a predetermined period.

The accommodated medicines replenished in the medicine storage are either used, returned, or lost due to damaged, discarded or missing medicines. The accommodated medicine retrieved may not necessarily be used. By maintaining information on the history of replenishment or the history of use as well recording the stored or retrieved accommodated medicine information, accurate stock control of the accommodated medicines is achieved. By maintaining the same record not only for accommodated medicines but also for non-accommodated articles, the aforementioned advantage will also be enjoyed with respect to the non-accommodated articles. The communicating unit may transmit the replenishment history information and the use history information to the external database.

The stored or retrieved non-accommodated article input unit may accept an input for each set of articles which comprises at least one non-accommodated article.

A "set of articles" is a module comprising at least one non-accommodated article. For example, a set of articles may comprise medical resources typically used for the purpose of a medical operation. Sets of articles may be categorized according to the medical department. Provision of sets of articles enables the medicine handling personnel to handle typical used non-accommodated articles together and facilitates management. Consequently, it will be useful in reducing human errors such as a retrieval error, input error and billing error. Provision of sets of articles will also facilitate standardization of medical practices (often referred to as "clinical path" or "critical path") since it will help eliminate situations where medicines selected differ from one medicine handling personnel to another.

The apparatus may also comprise a set of articles definition input unit which accepts an input by the medicine handling personnel to define a new set of articles.

If the medicine handling personnel is allowed to define a set of articles, sets of articles can be used that are adapted to the situations of respective hospitals and medical departments. Thereby, medicine management is further facilitated.

The apparatus may further comprise an amount change input unit which accepts an input from the medicine handling personnel regarding a change in the amount of non-accommodated articles included in the set of articles. The stored or retrieved non-accommodated article input unit may accept an input regarding the set of articles in which the amount is changed.

At actual sites of medical care, it may not necessarily be appropriate to use a set of articles as it is. For example, some medical operations may require more amount of a specific type of infusion fluid than normally required. By changing the amount of a non-accommodated article included in the set of articles, the medicine handling personnel is capable of selecting medicines adapted to the situation. Since the amount is changed in accordance with the situation, based on a standardized set of articles, input is easier than when medicines are selected from scratch at a site of medical care. Such a provision also helps reduce human errors.

When the amount change input unit accepts an input regarding a change in the amount, the controller may cause the display unit to display the associated non-accommodated article in a manner different from the way it is normally displayed.

By alerting of a deviation from the number defined in the standard set of articles when the medicine handling personnel changes the amount of the non-accommodated article included in the set of articles, visual confirmation by the medicine handling personnel is facilitated. Display different from the normal display may be achieved in any manner such as a change in color or a font used so long as the medicine handling personnel is alerted properly. Audio guidance may be provided in place of or in addition to the display.

The medicine management apparatus may further comprise a manipulation history generation unit which generates manipulation history information regarding the history of manipulation by the medicine handling personnel and stores the same in a recording medium.

The medicine management apparatus may further comprise a medical operation identification information detector which reads medical operation identification information assigned to medical operations to be performed for patients. The communicating unit may transmit the medical operation identification information thus read to an external database which stores detailed information on the medical operation corresponding to the medical operation identification information and may receive, from the database, the detailed information corresponding to the medical operation identification information thus read.

The term "medical operation identification information" refers to information such as an identification number or a barcode for uniquely identifying a medical operation to be performed. The term "medical operation identification information detector" refers to a detector such as a barcode reader. By acquiring medical operation identification information, the medicine management apparatus is capable of acquiring detailed information on associated medical information from a database.

The medicine management apparatus may further comprise a prompting information output unit which prompts the medicine handling personnel for review, when the same non-accommodated article as included in a set of articles is retrieved in addition to the set of articles.

If a non-accommodated article included in a set of articles is retrieved apart from the retrieval of the set of articles, there is a likelihood that the medicine handling personnel has taken out the same medicine twice by mistake. Communicating some information to prompt for review by the medicine handling personnel in such a case is effective in reducing mistakes in handling medicines. The notification may be provided in the form of display or audio output.

Another embodiment of the present invention relates to a medicine management system. The system includes the medicine management apparatus according to the above-described embodiment and a stock database which, connected to the medicine management apparatus via a network, stores data related to the stock status of the accommodated medicines. The medicine management apparatus transmits retrieved accommodated medicine information to the stock database.

Optional combinations of the aforementioned constituting elements, and implementations of the invention in the form of methods, apparatuses, systems, recording mediums and computer programs may also be practiced as additional modes of the present invention.

Figure 12:
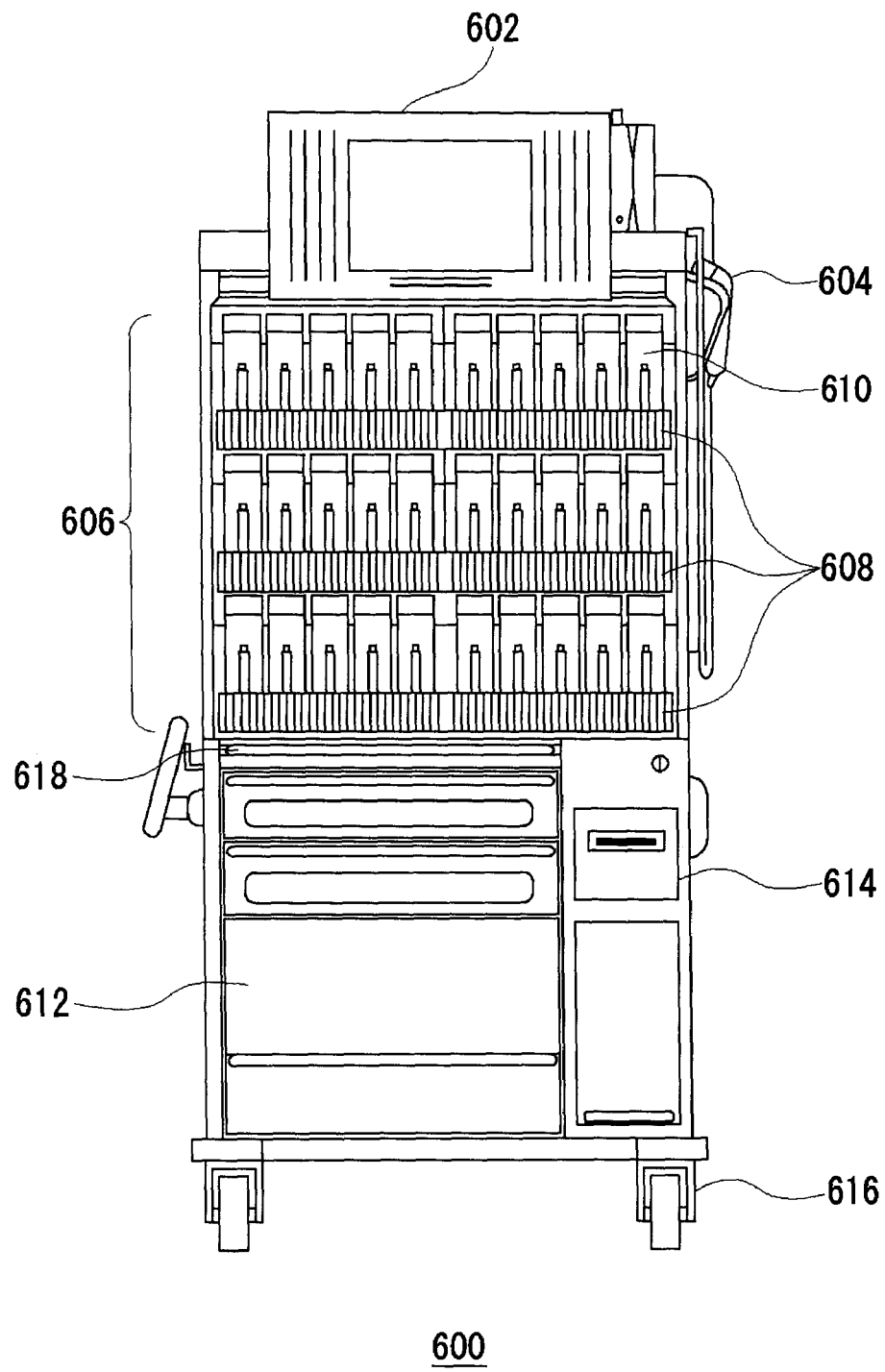
FIG. 12 shows the appearance of a medicine management apparatus according to a second embodiment.

FIG. 12 shows the appearance of the medicine management apparatus according to the embodiment.

The main part of a medicine management apparatus 600 is configured to be movable by a cart 616. A display apparatus 612 displays information to a medicine handling personnel such as a nurse. The following description assumes that a nurse uses the medicine management apparatus 600. The display device 602 operates as a touch panel to accept an input from a nurse via a graphics button or the like on the screen. A known input device such as a keyboard or a mouser may be used for input.

A barcode reader 604 is a device for scanning a barcode such as that assigned for identification of a non-accommodated article. A medicine storage 606 is a shelf to store accommodated medicines. The medicine storage 606 is divided into tiers by multiple catalogs 608. Each catalog 608 is further partitioned by multiple cassettes 610. Each of the cassettes 610 stores medicines of a single type. The cassette 610 is normally designed to store ampules or vials containing injection medicines. Alternatively, the cassette 610 may store medicines contained in a box, injection medicines packaged in a syringe or external medicines. An adaptor container conforming to a predetermined standard may be provided in order to store medicines of a form that can not themselves be stored in the cassette 610. Medicines of such a form may be stored in the cassette 610 by introducing them into the adaptor container Each of the cassettes 610 is provided with a mechanism for mechanically detecting the storage and retrieval of accommodated medicines stored in the cassette 610, by using a known method. Thereby, the medicine management apparatus 600 detects the storage and retrieval of the accommodated medicines. Each of the cassettes 610 is also provided with a mechanism for mechanically counting the number of accommodated medicines, by using a known method. Thereby, the medicine management apparatus 600 counts the number of accommodated medicines. The known methods referred herein are disclosed in, for example, JP 2001-199508. The catalog 608 and the cassette 610 will be described later in detail with reference to FIG. 25.

The medicine storage 606 is normally protected by a protective means such as a shutter so as to permit only authenticated nurses to take out medicines. The shutter is controlled by a method described later to be opened upon authentication of a nurse. The medicine storage 606 may not necessarily be provided inside the medicine management apparatus 600 but may be provided inside thereof.

A workbench 618 is a table normally accommodated in the medicine management apparatus 600. By drawing the workbench 618, the nurse can create a space for work. A multi-purpose drawer 612 is a drawer primarily to accommodate medicines that cannot be stored in the medicine storage 606 (i.e., non-accommodated articles). Non-accommodated medicines may not necessarily be stored in the multi-purpose drawer 612. A printer 614 is a device for printing information.

Figure 13:
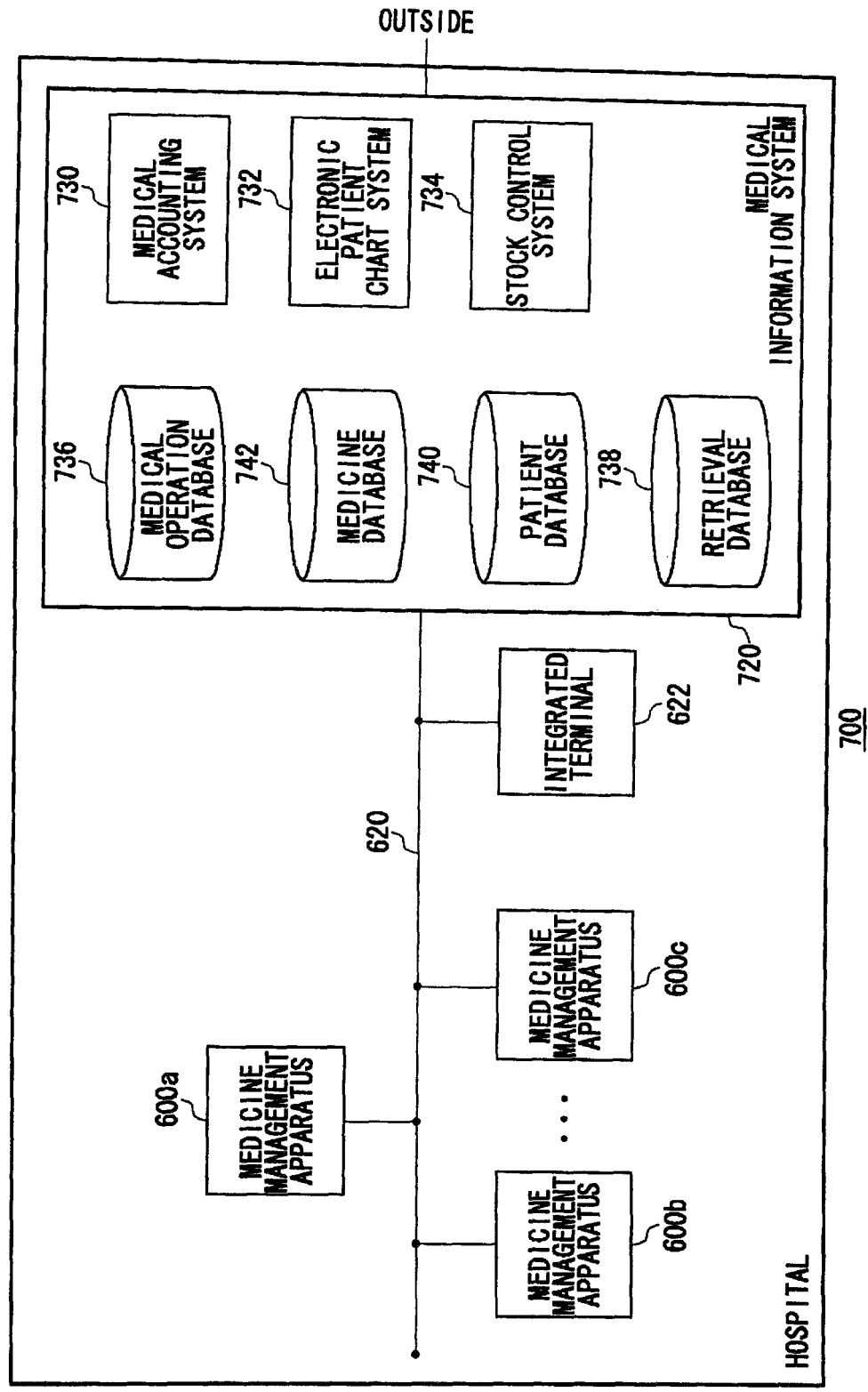
FIG. 13 shows a hardware structure in a hospital including the medicine management apparatus according to the second embodiment.

FIG. 13 shows a hardware structure in a hospital including the medicine management apparatus.

In a hospital 700, multiple medicine management apparatuses 600 including medicine management apparatuses 600a, 600b and 600c are connected to each other via a network 620. The network 620 may be a local area network (LAN) or a dedicated circuit. An integrated terminal 622 may be connected to the network 620 for integrated control of the multiple medicine management apparatuses 600. The integrated terminal 622 is a terminal for collecting data transmitted from the multiple medicine management apparatuses 600. The integrated terminal 622 may communicate the collected data to a medical information system 720. The medicine management apparatuses 600 may communicate with the medical information system 720 on an individual basis without the intervention of the integrated terminal 622. Data communication may be performed among the medicine management apparatuses 600, the integrated terminal 622 and a medicine handling personnel name display field 820 by using a predetermined, common communication protocol.

The medical information system 720 is a system built in each hospital 700. The internal configuration of the medical information system 720 varies depending on the situation of the hospital 700. The description of the second embodiment assumes that the medical information system 720 includes a medical accounting system 730, an electronic patient chart system 732, a stock control system 734, a medical operation database 736, a retrieval database 738, a patient database 740 and a medicine database 742.

The medical accounting system 730 is a system primarily for managing money charged for each patient. The electronic patient chart system 732 is a system primarily for managing chart information for each patient. The stock control system 734 is a system for stock control of medicines used in the entire hospital 700. The stock control system 734 of the second embodiment controls stock based upon information transmitted from the medicine management apparatuses 600.

The medical operation database 736 stores information related to medical operations. Information related to a medical operation scheduled to be performed by a doctor is stored in the medical operation database 736. The retrieval database 738 stores information related to medicines retrieved from the medicine management apparatus 600 during a predetermined period of time. The retrieval database 738 may store information on medicines used in each medical operation. The patient database 740 stores patient information. The medicine database 742 stores information related to medicines. The structure of these databases will be described in detail later with reference to FIG. 30 and subsequent figures.

Figure 14:
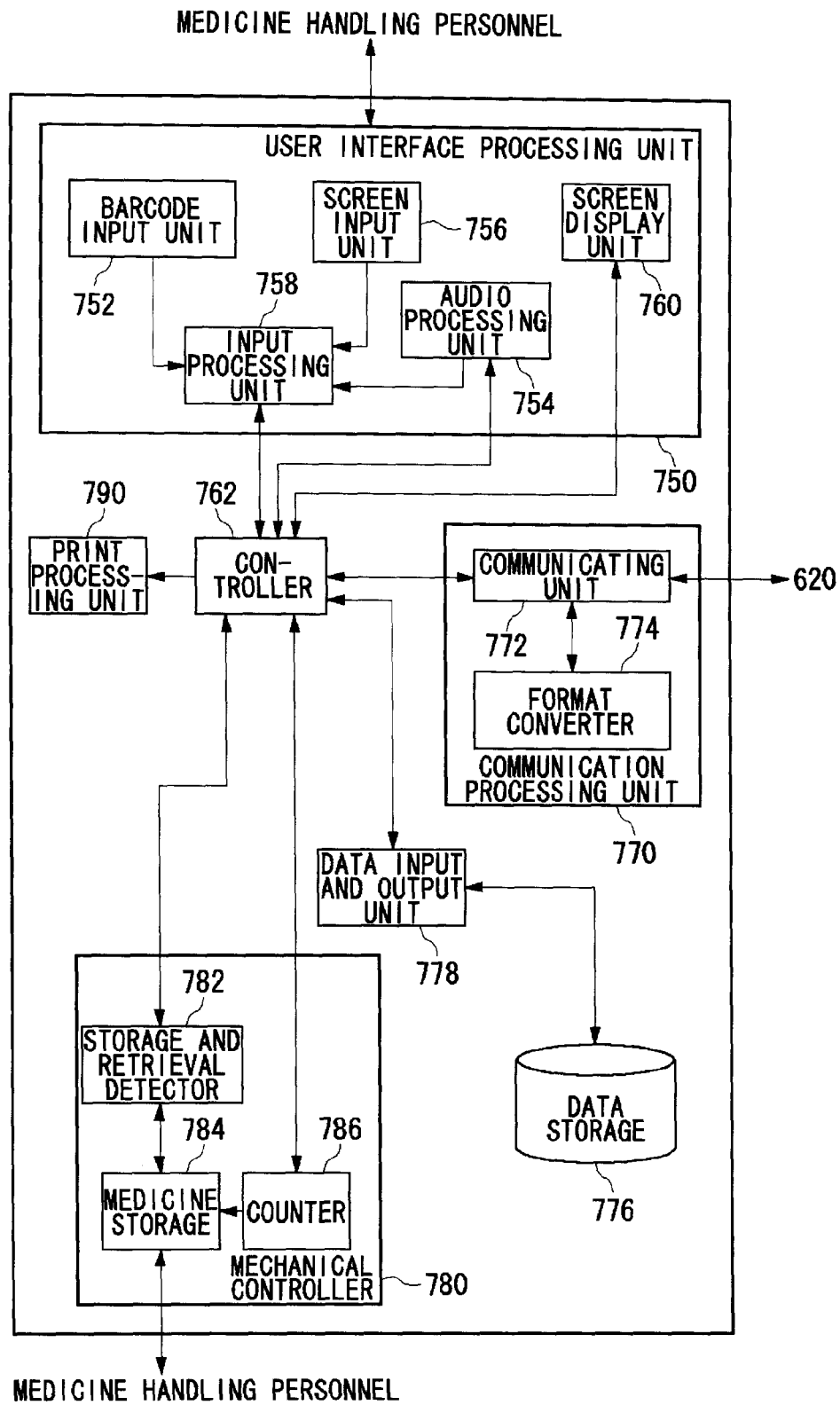
FIG. 14 is a functional block diagram of the medicine management apparatus according to the second embodiment.

FIG. 14 is a functional block diagram of the medicine management apparatus according to the second embodiment.

The blocks as shown may be implemented hardwarewise by components such as a computer CPU and mechanical devices, and softwarewise by a program such as that for data transmission and reception functions. FIG. 14 depicts functional blocks implemented by cooperation of hardware and software. Therefore, it will be obvious to those skilled in the art that the functional blocks may be implemented in a variety of manners by a combination of hardware and software.

The user interface processing unit 750 is responsible for processes related to the user interface. The user interface processing unit 750 includes a barcode input unit 752, a screen input unit 756, an input processing unit 758, an audio processing unit 754 and a screen display unit 760. The barcode input unit 752 accepts a barcode input from the barcode reader 604. A barcode may be attached to non-accommodated articles and nurses for identification. The screen input unit 756 accepts a touch-screen input provided by the nurse to the display device 602. The user interface processing unit 750 may be provided with other input units. The input information accepted via the input unit is transmitted to the input processing unit 758. The input processing unit 758 authenticates the nurse. The input processing unit 758 transmits only those inputs to the controller 762 that are provided normally. The screen display unit 760 displays various information to the nurse, using GUI. The audio processing unit 754 provides audio guidance stored in a data storage described later in accordance with an instruction from the controller 762. The audio processing unit 754 may accept an audio input from the nurse.

The mechanism controller 780 is a primarily mechanically constituted block and includes a storage and retrieval detector 782, a medicine storing unit 784 and a counter 786. The mechanism controller 780 is a mechanism for stock control of accommodated medicines. The medicine storing unit 784 is for storing accommodated medicines and is embodied primarily by the medicine storage 606 of FIG. 12. As the nurse manipulates the apparatus for storage or retrieval of accommodated medicines, the storage and retrieval detector 782 detects the storage or retrieval by a known method. The counter 786 counts the number of medicines of respective types by a known method.

The communication processing unit 770 is responsible for processing communication with external devices. The communication processing unit 770 includes a communicating unit 772 and a format converter 774. By connecting to the medical information system 720, the communicating unit 772 exchanges data with the integrated terminal 622 and the medical information system 720 of FIG. 13. For transmission of data from the communicating unit 772 to the various databases shown in FIG. 13 via the network 620, the format converter 774 converts the format of data in accordance with the communication protocol or the format of data storage in the external databases. The format converter 774 also converts the data received from external devices into the format used in the medicine management apparatus 600. A data input and output unit 778 provides an interface for data input and output between the controller 762 and the data storage 776. In accordance with an instruction from the controller 762, the data input and output unit 778 records storage and retrieval of medicines, replenishment history, use history, information related to nurses, definition of sets of articles and manipulation history, etc. in the data storage 776 in a predetermined format. The data input and output unit 778 also acquires information required by the controller 762 from the data storage 776 in a predetermined format.

The controller 762 is responsible for integrated control of the user interface processing unit 750, the mechanism controller 780, the communication processing unit 770, a print processing unit 790 (described later) and the data input and output unit 778. The controller 762 records information on storage and retrieval of medicines in the data storage 776 via the data input and output unit 778, on the basis of the nurse's input accepted by the input processing unit 758 or information on storage and retrieval of medicines as detected in the mechanism controller 780. The controller 762 also directs the communication processing unit 770 to transmit the information. The data storage 776 stores, for example, information on storage, retrieval, replenishment and use status of medicines for which the medicine management apparatus 600 is responsible, information on the nurses, information defining the sets of articles, history of jobs done by the nurses, etc. The data structure of the information will be described in detail later in explaining the user interface screen. In accordance with an instruction from the nurse, the controller 762 causes necessary information to be printed via the print processing unit 790.

The user interface screen of the medicine management apparatus 600 will now be described.

Figure 15:
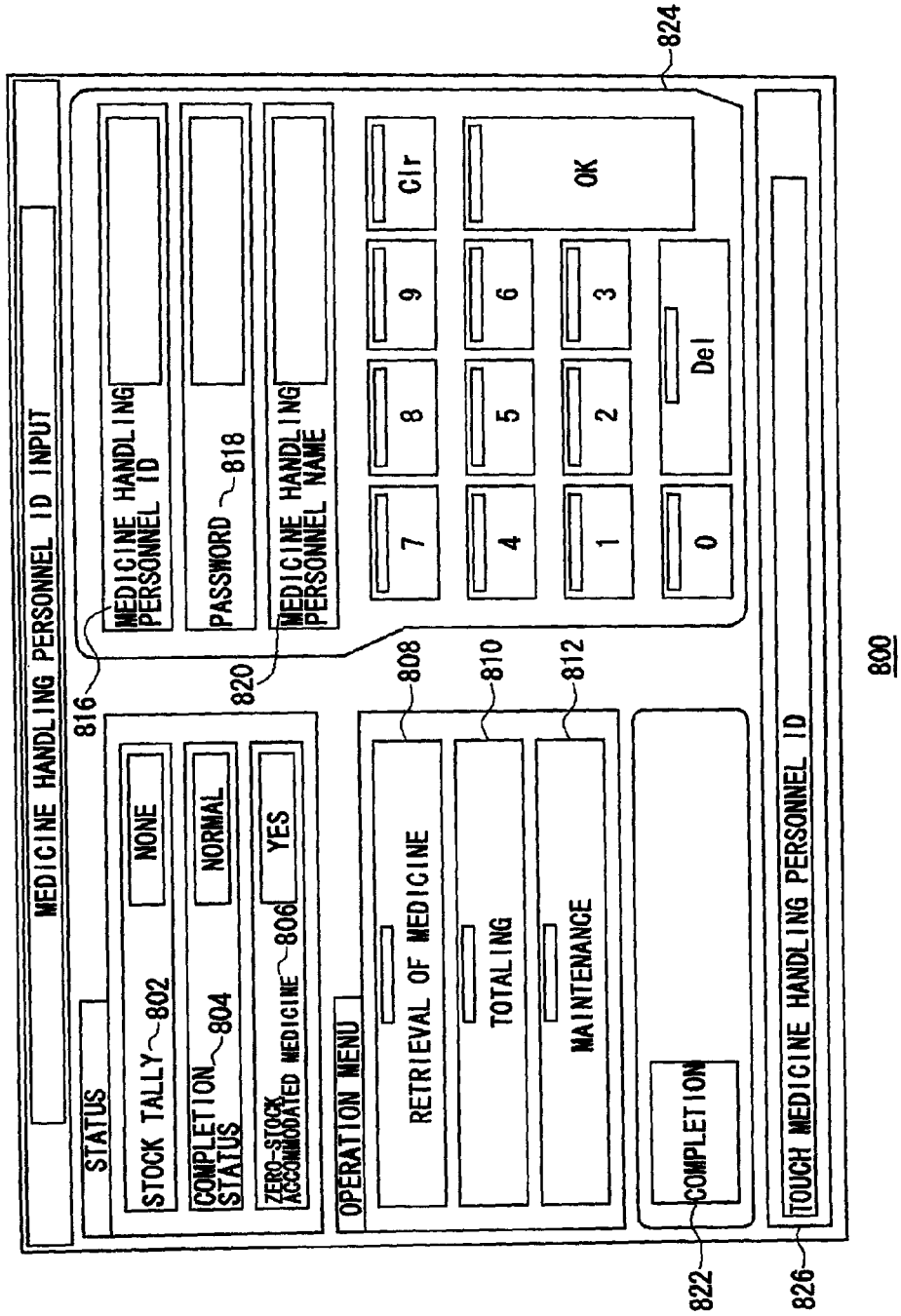
FIG. 15 shows a login screen of the medicine management apparatus according to the second embodiment.

FIG. 15 shows a login screen 300 which is an initial screen of the medicine management apparatus.

In a medicine handling personnel ID input field 816 on a login screen 800, the nurse enters an ID number which is assigned to each medicine handling personnel (in this, the nurse) and called a medicine handling personnel ID. The nurse also enters a password for authenticating the nurse in a password input field 818. These inputs are provided by touching a ten key 824. Alternatively, the inputs may be provided by using a pre-assigned barcode. If the medicine handling personnel ID and the password are authenticated by the input processing unit 758, a medicine handling personnel name display field 820 displays the name of the nurse, and the nurse is authorized to use the medicine management apparatus 600. Information including the medicine handling personnel ID, password and nurse name are stored in the data storage 776. Alternatively, a database included in the medical information system 720 may store the information.

A stock tally display field 802, a completion status display field 804 and a zero stock display field 806 display information on the status of the medicine management apparatus 600. The stock tally display field 802 displays whether the number of accommodated medicines physically counted by the counter 786 matches the stock of accommodated medicines maintained by the data storage 776 of the medicine management apparatus 600. The controller 762 keeps track of the amount of stock of accommodated medicines by exhaustively recording information related to the storage and retrieval of accommodated medicines in the data storage 776. The amount of stock of accommodated medicines is physically counted by the counter 786. Normally, the count and the information match but may not match due to an error that occurs in the process or a mechanical failure. If the stock tally display field 802 displays "matching failure", a problem like these is occurring. In this way, an error related to the counting of accommodated medicines is immediately detected. Since the accommodated medicines usually include expensive medicines, early detection of a mistake in management due to an error in the process performed by the medicine management apparatus 600 is important. The completion status display field 804 displays whether the apparatus is turned off normally by the nurse in the previous use. If the system was not terminated normally, it is indicated as such. The zero stock display field 806 displays whether any type of accommodated medicine has run out of storage.

A medicine retrieval operation button 808, a totaling operation button 810 and a maintenance operation button 812 are a group of buttons corresponding to operations that should be performed by the nurse. The medicine retrieval operation button 808 is a button for the operation of storing and retrieving medicines. When the medicine retrieval operation button 808 is touched, the screen of FIG. 16 described later is shown. The totaling operation button 810 is a button for a totaling operation. Touching the totaling operation button 810 will display the screen of FIG. 26 described later. The maintenance operation button 812 is a button for maintenance of the medicine management apparatus 600. Touching the maintenance operation button 812 will display the screen of FIG. 24 described later. When a completion button 822 is touched, the process in the medicine management apparatus 600 is terminated. An input information display field 826 displays guidance related to the input operation.

Figure 16:
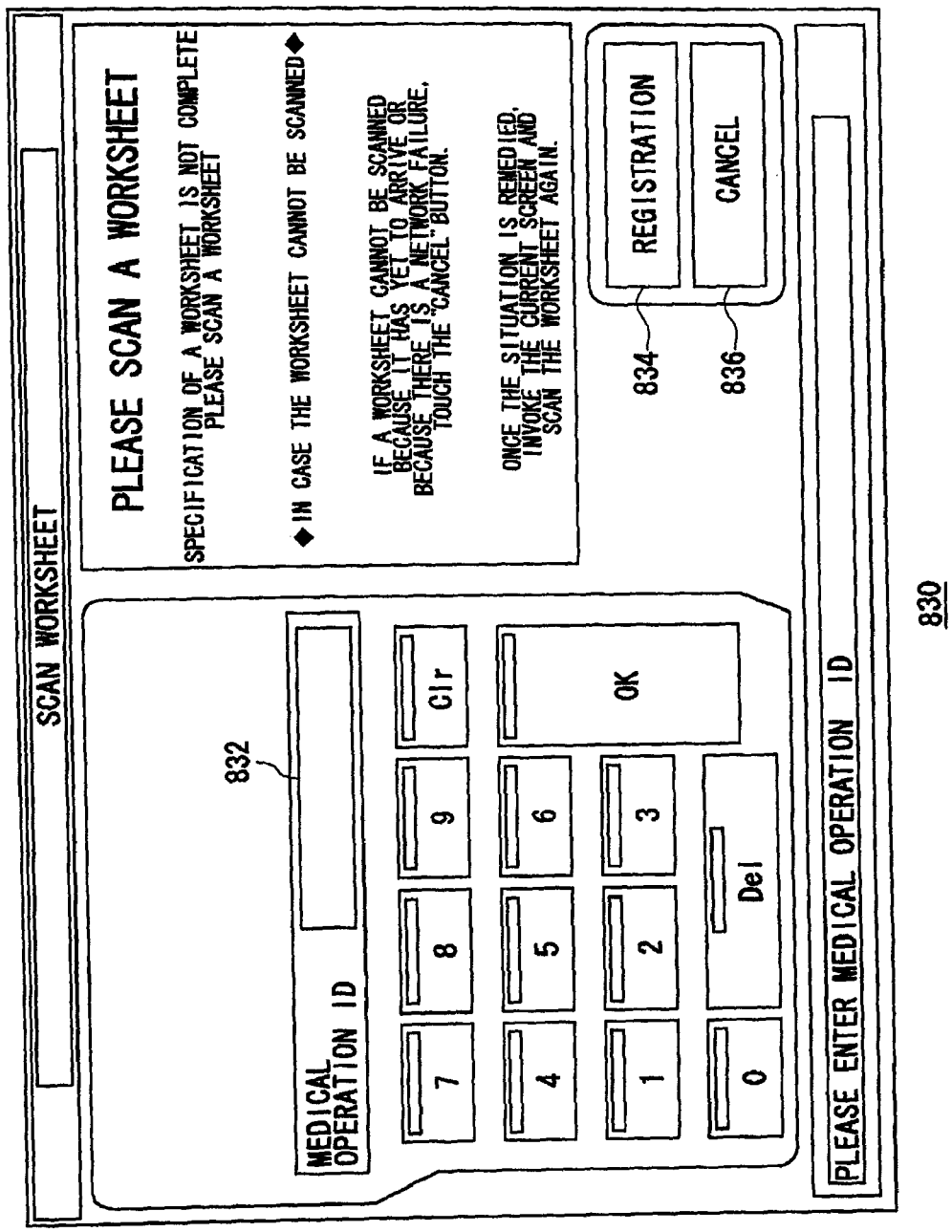
FIG. 16 shows a worksheet scanning screen shown when the medicine retrieval operation button is touched in the login screen according to the second embodiment.

FIG. 16 shows a worksheet scanning screen shown when the medicine retrieval operation button is touched in the login screen.

In retrieving a medicine, the type of medical operation for which the medicine is taken out of storage should be identified. In a medical operation ID input field 832 on the worksheet scanning screen 830, the nurse enters a medical operation ID which is a number for identifying the medical operation and assigned to each worksheet. The medical operation ID may be read by the barcode reader 604. A worksheet is a piece of paper carrying information related to the details of the medical operation. The medical operation ID is entered in each worksheet. The worksheet and the medical operation ID will be described in detail with reference to FIG. 17.

Figure 18:
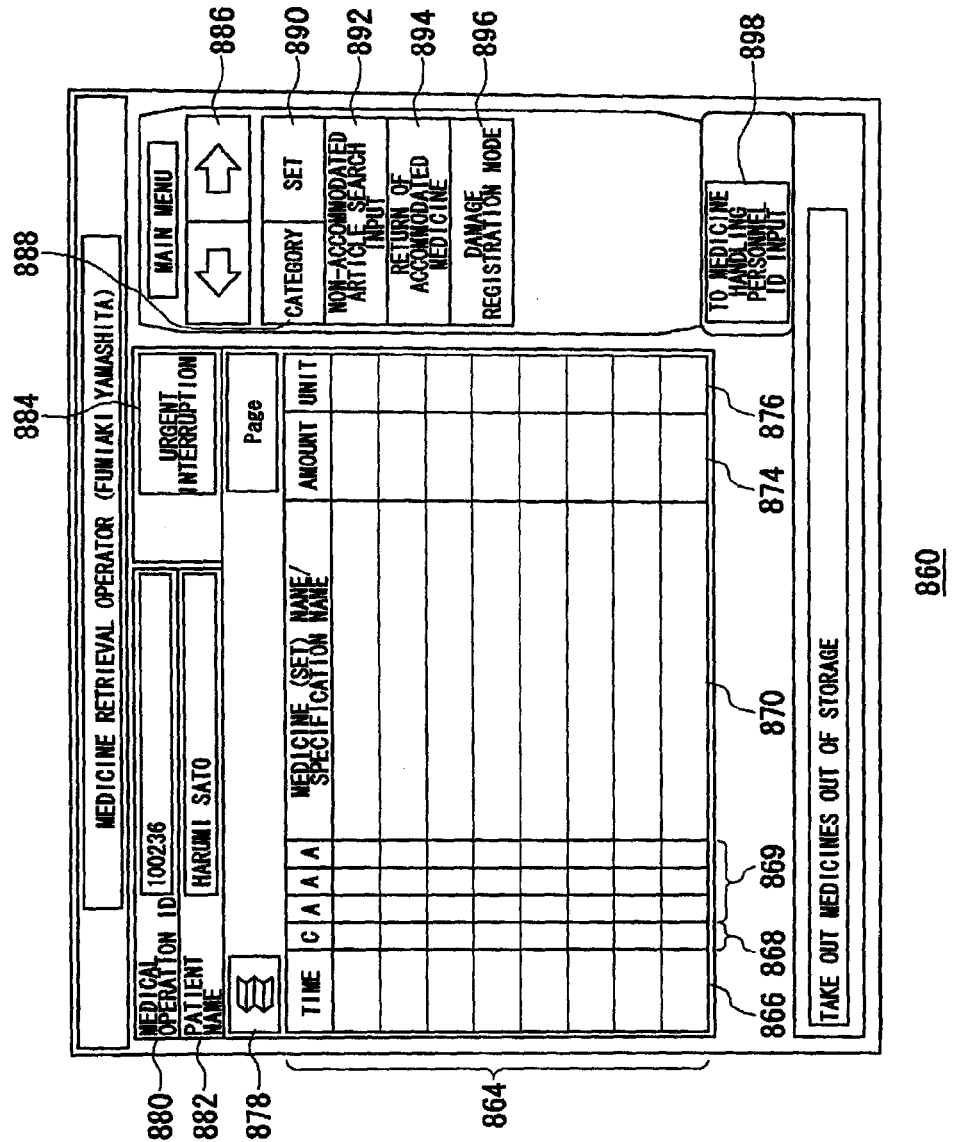
FIG. 18 shows an initial medicine retrieval screen displayed after the worksheet scanning screen of FIG. 16 according to the second embodiment.

After reading the medical operation ID entered in the worksheet, the medicine management apparatus 600 acquires information (hereinafter, referred to as "medical operation details") from the medical operation database 736 via the communicating unit 772, the medical operation details being information which is the same as the information entered in the worksheet. If a registration button 834 is touched after the medical operation details are properly read, the screen of FIG. 18 is shown. If the medical operation ID is not read and a cancel button 836 is touched, the screen of FIG. 18 is shown without reading the medical operation details. If the medical operation details cannot be properly acquired and the cancel button 836 is touched, the screen of FIG. 18 will also be shown.

Figure 17:
FIG. 17 shows a worksheet for the medicine management apparatus according to the second embodiment.

FIG. 17 shows a worksheet.

Normally, the details of each medical operation are determined by a doctor. The particulars of the medical operation entered in the worksheet are also stored in the medical operation database 736. A worksheet 840 is a piece of paper prepared in accordance with the medical operation details. The nurse reviews the details entered in the worksheet 840 before preparing for the medical operation. When the medical operation ID, which is entered in a medical operation ID field 850, is input while the worksheet scanning screen 830 is being shown, the medicine management apparatus 600 acquires the same medical operation details as entered in the worksheet 840 primarily from the medical operation database 736.

A patient ID field 842 displays an ID number (hereinafter, referred to as "patient ID") assigned to each patient for which the medical operation is performed. Similarly, the patients, medical operations and medicines are respectively assigned ID numbers for identification. The medicine management apparatus 600 acquires necessary information from the databases in the medical information system 720 by using the ID numbers as keys. Referring to FIG. 17, the nurse can know that the patient's name is "Harumi Sato" by looking at a patient name field 846, the patient ID is "9305277" by looking at a patient ID field 842, and the medical operation scheduled to be performed is "low anterior resection of the rectum" by looking at a scheduled medical operation field 848.

FIG. 18 shows an initial medicine retrieval screen displayed after the worksheet scanning screen.

A medical operation ID field 880 of the initial medicine retrieval screen 860 displays the medical operation ID entered in the medical operation input field 832. A patient name field 882 displays the name of the patient shown in the patient name field 846. The medicine management apparatus 600 acquires the name of the patient from the medical information system 720, by using the medical operation ID acquired from the medical operation ID field 850 as a key. If the worksheet was not read from the worksheet scanning screen 830, the name of the patient is not displayed in the patient name field 882.

A storage and retrieval information display area 864 displays information related to various manipulations such as storage and retrieval of medicines. The manipulation in this case means dispensation (retrieval), return and registration of damage (described later). Entries in the storage and retrieval information display area 864 will be explained with reference to FIG. 19 and subsequent figures. A brief summary of the entries will now be explained with reference to FIG. 18. A time field 866 displays time at which the manipulation displayed occurred. A category field 868 displays the type of manipulation. The types of manipulation include, for example, retrieval and return. An alert field 869 displays an alert assigned to each medicine. Some medicines require special care in handling for reasons of high prices or danger. As will be described later with reference to FIG. 24, the nurse can configure an alert for each medicine type. An alert thus configured is displayed in the alert field 869. There are three columns for alerts in the alert field 869 which correspond to the levels of alert, i.e., the importance of alerts. More important alerts are displayed toward the right.

A medicine name field 870 displays the name of the medicine handled. Information such as the specification of the medicine may be displayed in addition to the name of the medicine. A medicine name field 348 displays the name of the medicine handled. A unit field 876 displays the unit of medicines handled. A display switching button 878 switches between two ways of displaying the storage and retrieval information display area 864 Each time the display switching button 878 is touched, the history of storage and retrieval of the medicines handled and an increase or decrease in the amount of medicines stored or retrieved are alternately displayed. Alternatively, the storage and retrieval information display area 864 may switch between the four modes of display including: retrieved medicines; returned medicines; damaged and registered medicines; and all medicines that are targets of handling. Alternatively, the mode of switching may be user-definable.

When a nurse interrupts for a job while another nurse is working, the interrupting nurse touches an urgent interruption button 884. As mentioned before, a nurse should be authenticated before manipulating the medicine management apparatus 600. There are cases, however, where a nurse needs to take out medicines urgently due to, for example, an urgent medical operation, from the medicine management apparatus 600 with which another nurse is working. In this case, if the interrupting nurse is permitted to take out necessary medicines at will while the interrupted nurse is working, authentication of the nurses will be incomplete. If, on the other hand, the job of the interrupted nurse is terminated, an incomplete record of the interrupted nurse will remain, presenting an inconvenience in managing manipulation history data described later. In this case, the interrupting nurse is expected to use the urgent interruption button 884 to suspend the job done by the interrupted nurse and temporarily save the job status before doing his or her job. When the interrupting nurse finishes his or her job, the interrupted nurse can resume his or her job based upon the job status thus saved.

A page switching button 886 switches between pages when the medicines handled from the storage and retrieval information display area 864 cannot be displayed in a single screen. A category selection button 888 selects non-accommodated articles according to the category. Categories are those with which the non-accommodated articles are grouped in accordance with their use such as "medical operation", "anesthesia", "surgery" and "otolaryngology". Touching the category selection button 888 will display a category selection screen (not shown). The nurse searches for and selects a desired non-accommodated article according to the category, before providing an input indicating its retrieval or return. Retrieval of the accommodated medicines from the medicine storage 606 is automatically detected by the storage and retrieval detector 782. As for the non-accommodated articles, medicine IDs, which are ID numbers embodied on barcodes and identifying these medicines, are entered by using the barcode reader 604. Input of IDs for non-accommodated articles may be provided by a selection from the screen. Since a majority of medicines are grouped according to the category, selection of a desired medicine is easy.

A set input button 890 is a button for providing an input for a set of articles (hereinafter, such an input will be simply referred to as a "set input"). A set input indicates a manipulation for input designating a set of articles as one unit. A detailed description will be given later with reference to FIG. 21. A non-accommodated article search button 892 is a button for invoking a screen (not shown) from which to search for a non-accommodated article. The nurse uses this screen to search for a desired medicine, in a character search using a part of the name of the non-accommodated article or by using a part of the medicine ID as a key. Alternatively, various information described later associated with the medicines may be used as a key in the search. The location of the non-accommodated article may be identified in this search.

An accommodated medicine return button 894 invokes a return screen (not shown) from which to return an accommodated medicine. Upon invoking the screen, the nurse identifies the accommodated medicine that should be returned in the list of accommodated medicines taken out of storage, before returning the accommodated medicine to the medicine storage 606. When the return is recognized by the medicine management apparatus 600, the initial medicine retrieval screen 860 will be shown again.

A damage registration button 896 invokes a screen (not shown) from which to register damage of a medicine. When the nurse damages a medicine taken out, the nurse invokes this screen for registration of the damage. In this way, medicines lost due to damage are managed in addition to medicines actually used or returned. The term "damage" in this case encompasses discarding and loss. It means that the medicine is lost without being used. In this way, the identity of a person who damaged the medicine is recorded by the data input and output unit 778 in the data storage 776, since the nurse is identified by the medicine handling personnel ID. The screen from which to register damage also accepts an input for the situation and reason for the damage.

When a completion button 898 is selected, the login screen 800 is shown again. The worksheet scanning screen 830 may be shown. In other words, the nurse may scan the worksheet when the job is done.

Figure 19:
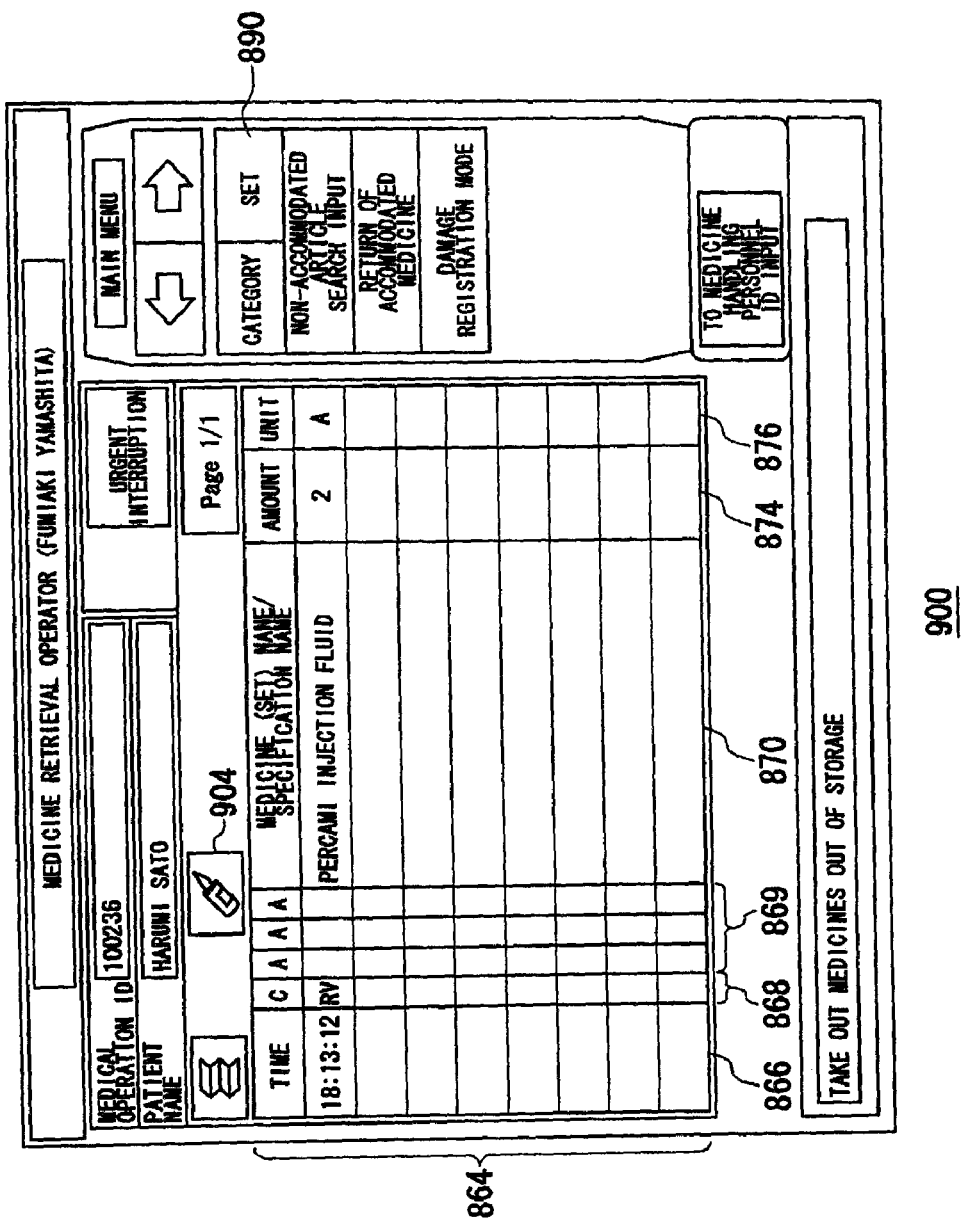
FIG. 19 shows a retrieved medicine screen displayed when a nurse has taken out an accommodated medicine from a medicine storage after the initial medicine retrieval screen of FIG. 18 is displayed, according to the second embodiment.

FIG. 19 shows a retrieved medicine screen displayed when the nurse has taken out the accommodated medicine from the medicine storage after the initial medicine retrieval screen is displayed.

The figure shows that the nurse took out two units of Percami (accommodated medicine) from storage. When the retrieval detector 782 detects the retrieval of Percami (provisional name) from the medicine storage 784, the controller 762 causes the screen display unit 760 to display the entries as shown in the storage and retrieval information display area 864. The controller 762 also directs the data input and output unit 778 to record the storage and retrieval of accommodated medicines in the data storage 776.

A time field 866 displays time when the manipulation for retrieval was done. A category field 868 shows that the manipulation was directed to retrieval. A medicine name field 870 displays "Percami injection medicine (provisional name)", which is the name of the accommodated medicine taken out of storage. An amount field 874 shows that two units were taken out of storage. A unit field 876 indicates that the injection medicine taken out is contained in an ampule. As the nurse takes out an accommodated medicine from storage, the nurse can review information related to the accommodated medicine taken out on a real time basis by referring to the storage and retrieval information display field 864.

When the nurse touches the part of the storage and retrieval information display field 864 related to the accommodated medicine taken out and then touches a detailed medicine information button 904, a screen showing detailed information on the accommodated medicine is displayed (not shown). From the screen, the nurse can obtain detailed information on the medicine such as that of FIG. 30. The medicine management apparatus 600 may acquire information related to the medicine from the medicine database 742 when the detailed medicine information button 904 is touched. Since this allows the nurse to obtain detailed information on a medicine for which an alert is displayed in the alert field 869, the nurse can learn how to handle the medicine while manipulating the medicine management apparatus 600.

Figure 20:
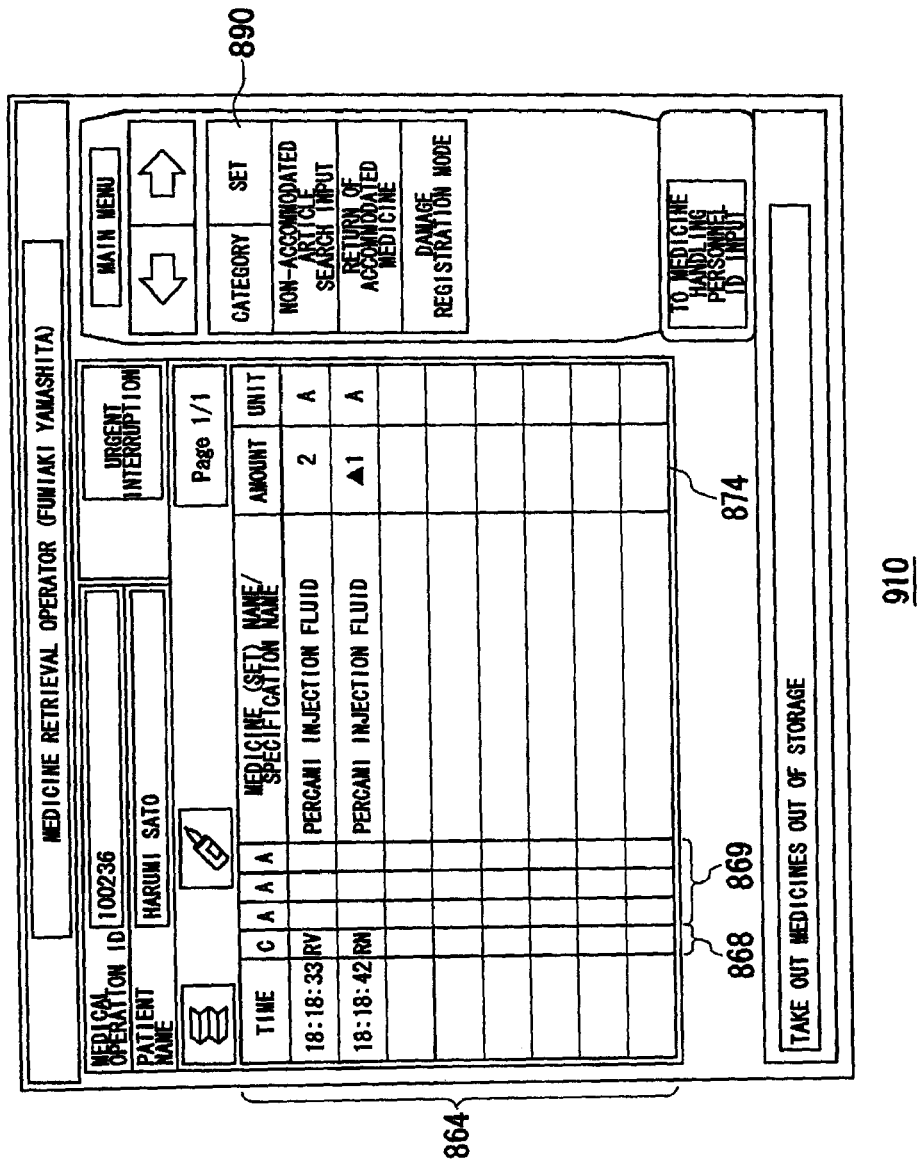
FIG. 20 shows a medicine retrieval screen displayed when an accommodated medicine taken out from the medicine retrieval screen of FIG. 19 is returned.

FIG. 20 shows a medicine retrieval screen displayed when one of the two ampules of "Percami (provisional name)" taken out from the medicine retrieval screen is returned.

In returning "Percami (provisional name)", the nurse first invokes a return screen (not shown), selects "Percami (provisional name)", which is to be returned, and sets the number of units returned. When the nurse returns "Percami (provisional name)" subsequently to the associated cassette 610, the storage and retrieval detector 782 detects the return. The controller 762 directs the screen display unit 760 to display information in the second row from top of the storage and retrieval information display field 864 in the medicine retrieval screen 910. The category field 868 indicates that the manipulation performed is for returning the medicine. The amount field 874 indicates that one ampule is returned. The figure shows that two ampules of "Percami (provisional name)" were taken out but one of them was returned. Thus, the history of manipulation by the nurse is displayed.

Figure 21:
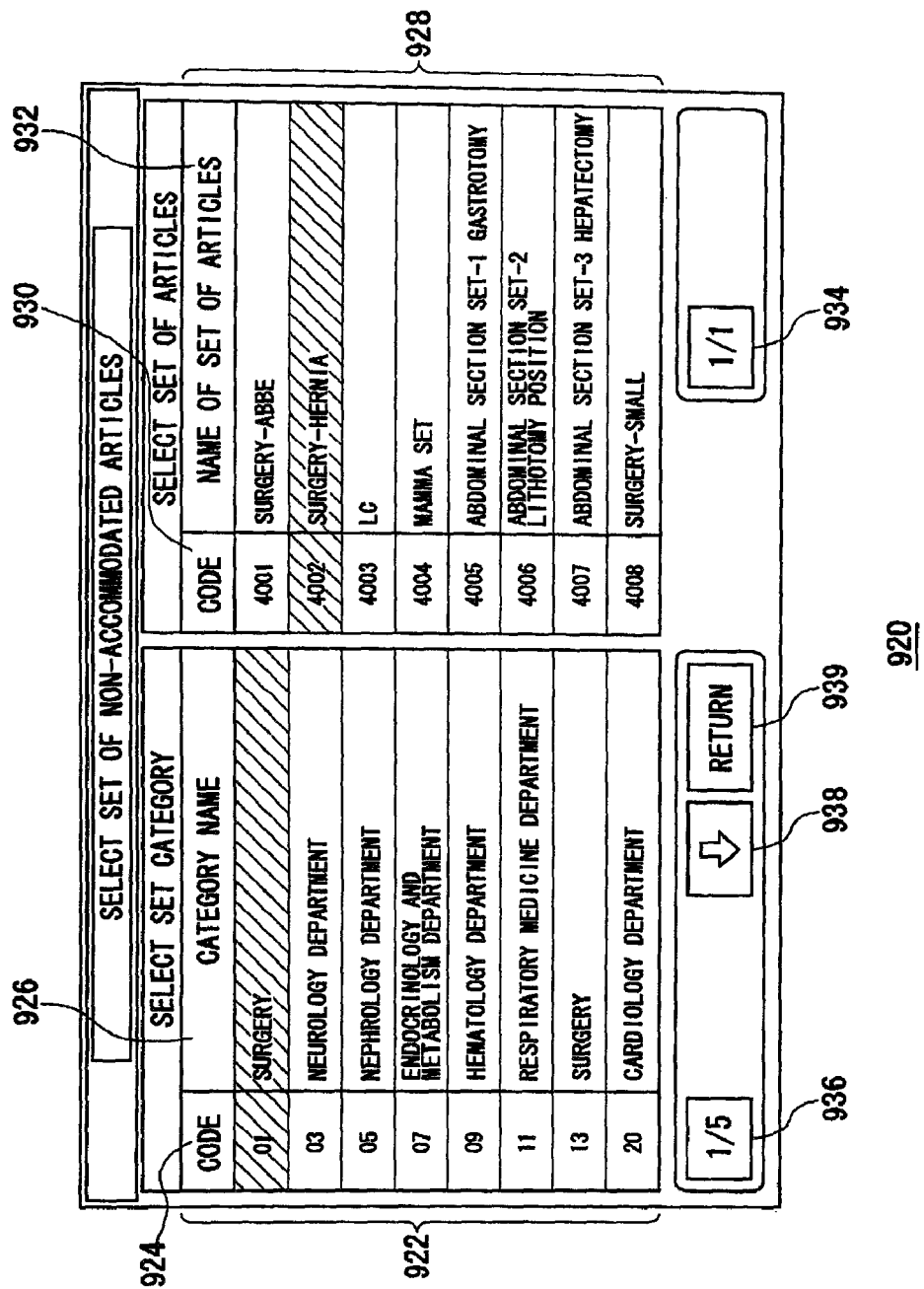
FIG. 21 shows a set of articles selection screen of the medicine management apparatus according to the second embodiment.

FIG. 21 shows a set of articles selection screen displayed when the set input button of the initial medicine retrieval screen is touched.

The nurse can provide an input for storage and retrieval of non-accommodated articles as well as accommodated medicines. In this case, too, the controller 762 directs the data input and output unit 778 to record such storage and retrieval in the data storage 776. Further, the nurse is capable of providing an input for storage and retrieval of a set of articles. The nurse refers to a set of articles selection screen 920 to select a desired set of articles from pre-registered sets of articles. Information on the sets of articles may be stored in the data storage 776 or acquired from an external database.

A set category field 922 shows the category of a set of articles (hereinafter, such a category will be simply referred to as a "set category"). While the figure shows that the sets of articles are grouped according to the medical department, they may be grouped from alternative perspectives. For example, the sets of articles may be grouped according to their use. A set category code field 924 displays an ID number for identifying the medical department. A set category name field 926 displays the name of the medical department. The nurse selects a medical department by touching the field for a desired medical department in the set category field 922. The figure shows that "surgery" is selected. A set category selection page 936 displays the page number of the set category field 922. The figure indicates that there are five pages for set categories, of which the first page is displayed. A page switching button 938 changes the page. Touching a return button 939 shows the medicine retrieval screen 910 again.

A set of articles selection field 928 displays sets of articles categorized under the medical department selected in the set category field 922. When a set category is selected in the set category field 922, the set of articles selection field 928 displays a list of sets of articles included in the set category. A set of articles code field 930 displays an ID number for identifying a set of articles. A set of articles name field 932 displays the name of a set of articles. The nurse selects a set of articles by touching a field for a desired set of articles in the set of articles selection field 928. A set of articles selection page 934 indicates the page number of the set of articles selection field 928. The figure shows that the set of articles named "surgery—hernia" categorized under "surgery" is selected.

FIG. 22 shows a set of articles input screen displayed when a set of articles is selected from the set of articles selection screen.

A set category display field 942 of the set of articles input screen 940 displays "surgery", which is a set category selected in the set category field 922. The set of articles display field 944 displays "surgery—hernia", which indicates a set of medicines selected in the set of articles selection field 928. A set of articles particulars field 946 displays medicines included in the selected set of articles "surgery—hernia". The set of articles "surgery—hernia" includes the medicines shown in the set of articles particulars field 946.

An item code field 948 displays a medicine ID. A medicine name field 950 displays the name of a medicine. A prescribed amount field 952 displays the prescribed amount of medicines included in a set of articles. An amount field 954 displays the amount of medicines actually taken out. As described later, the amount can be changed in retrieving. A unit field 956 displays the unit of medicines. FIG. 22 shows that normal saline, a non-accommodated article, with an item code "1669" is included in the set of articles "surgery—hernia". The prescribed amount of "normal saline" included in the set of articles "surgery—hernia" is "200 ml", of which "200 ml" is taken out of storage.

An amount change button 958 is a button for changing the amount of a medicine included in a set of articles. The prescribed amount of medicines included in a set of articles is defined as shown in the prescribed amount field 952. However, more than or less than the prescribed amount may be required at a site of medical care taking out a set of articles from storage. The nurse uses the prescribed amount change button 958 to change the actual retrieved amount of the medicine selected by touching in the set of articles particulars field 946 and actually taken out of storage. Once the amount of a medicine included in a set of articles is changed by activating the amount change button 958, the screen display unit 760 changes the color with which the changed medicine is displayed in the set of articles particulars field 946. For example, if more than the prescribed amount is designated by the change, the changed medicine is displayed with a yellow background. If less than the prescribed amount is designated by the change, the background color is changed to red. Alternatively, the audio processing unit 754 may alert of the change from the prescribed amount with audio guidance.

Touching a set amount button 962 invokes a screen (not shown) from which to change the number of sets of articles to be taken out of storage. The set amount button 962 also displays the number of sets of articles to be taken out of storage. The figure shows that two sets of articles "surgery—hernia" are to be taken out. Touching a retrieval button 964 completes the input regarding the retrieval of sets of articles. Touching a return button 966 shows the set of articles selection screen 920 again.

FIG. 23 shows a medicine retrieval screen displayed when the retrieval of a non-accommodated article "Netracatheter (provisional name)" is input after providing an input designating the retrieval of one set of articles "surgery—hernia".

As already mentioned, the set of articles "surgery—hernia" includes a non-accommodated article "Netracatheter (provisional name)", and the nurse is attempting to take out the same non-accommodated article. In this case, the nurse may be in error in manipulating the apparatus for retrieval. This is because it is deemed more appropriate and natural for the nurse to adjust the retrieved amount of the non-accommodated article "Netracatheter (provisional name)" included in the set of articles, instead of providing an input designating the retrieval of the non-accommodated article "Netracatheter (provisional name)". In such a situation, the screen display unit 760 alerts the nurse by displaying a duplicate dispensation alert display 972. Alternatively, the audio processing unit 754 may provide an audio alert.

Described above is the manipulation related to the retrieval and the like of medicines. The manipulation for storage and retrieval of accommodated medicines is immediately displayed in the storage and retrieval information display field 864 once the medicine is taken out of the medicine storage 606. As for the non-accommodated articles, an input for storage and retrieval is done via the non-accommodated article search button 892, which input searches for the article in the registered information. An input for storage and retrieval may be provided by scanning a barcode assigned to the non-accommodated article. An input for storage and retrieval may also be provided by searching for a set of articles, from the information on the sets of articles registered. Inputs for storage and retrieval of medicines managed by the medicine management apparatus 600 are provided as described above. When the completion button 898 is touched, the series of steps for manipulation is terminated. In the process of completion, the data input and output unit 778 stores information related to the storage and retrieval of medicines in association with the manipulation in the data storage 776. The master information may also be transmitted to the medical information system 720. The print processing unit 790 may be directed by the controller 762 to print the information related to the storage and retrieval.

Figure 24:
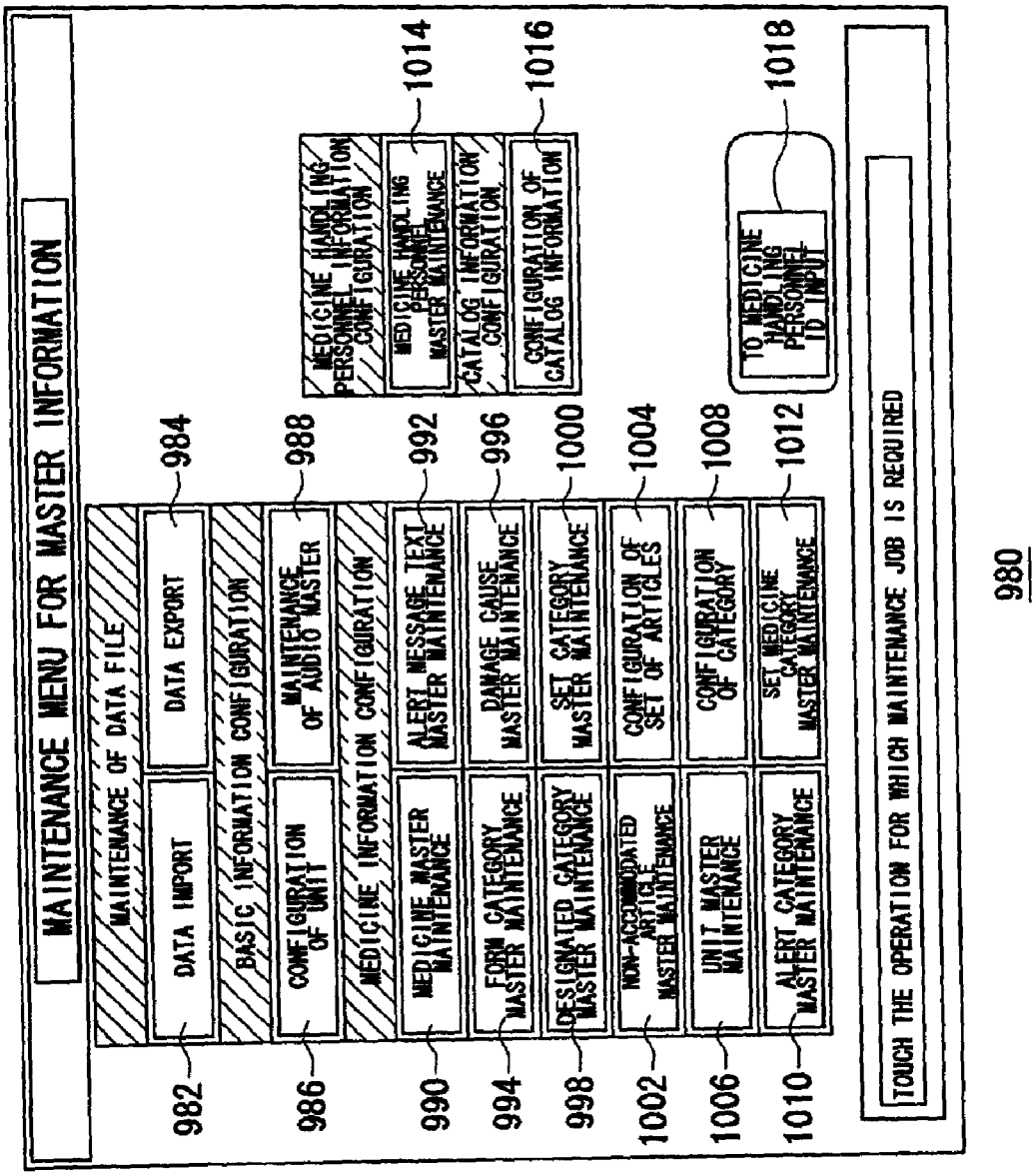
FIG. 24 is a maintenance screen of the medicine management apparatus according to the second embodiment.

FIG. 24 is a maintenance screen displayed when the maintenance operation button is touched in the login screen.

A maintenance screen 980 is a screen from which to provide various configurations in the medicine management apparatus 600. The following configurations are directed by the controller 762 to be stored in the data storage 776 via the data input and output unit 778. A data import button 982 is for acquiring configuration data for the medicine management apparatus 600. A data export button 984 is for recording the configuration data for the medicine management apparatus 600. The configuration data may be recorded in a portable recording medium such as a floppy disk or recorded in an external recording medium via the network. In this way, the basic configuration data can easily be copied even when multiple medicine management apparatuses 600 are provided in a hospital.

Activating a unit configuration button 986 shows a screen (not shown) from which to set the configuration of the medicine storage 606. An additional medicine storage 606 may be provided in addition to the medicine storage 606 already provided in the medicine management apparatus 600. In case the medicine management apparatus 600 controls multiple medicine storages 606, the unit configuration button 986 is used to establish their configuration, designating each medicine storage 606 as a "unit". More specifically, the configuration pertains to the placement of the units and the number of catalogs 608 and cassettes 610 included in each unit. Activating a audio master registration button 988 shows a screen (not shown) from which to register an audio message. Multiple audio messages, such as an alert or caution regarding the handling of medicines, can be registered. A medicine master registration button 990 described later may be used to configure such that a desired message selected from the registered audio messages is associated with each medicine. Audio messages for guidance on manipulation may also be provided in addition to those associated with medicines. The audio messages thus registered are output by the audio processing unit 754.

Activating the medicine master registration button 990 shows a screen (not shown) from which to set information related to a medicine. For example, the size of the accommodated medicine or an alert message may additionally be set up for the medicine. While Information related to the medicine is stored in the medicine database 742, information such as that of FIG. 30 inherent to the medicine can additionally be stored in the medicine management apparatus 600. This includes, for example, information such as the size of the medicine. Activating an alert text master registration button 992 shows a screen (not shown) from which to set the texts of alert messages. Multiple texts of alert messages, including the alerts and cautions regarding the handling of medicines, can be registered. By using the medicine master registration button 990, the texts of alert messages thus set can be associated with the medicines as additional information. Activating a form category master registration button 994 shows a screen (not shown) from which to register the forms of medicines. The forms are represented by categories such as tablets, capsules, injection medicines and instruments. The medicine master registration button 990 can be used to associate the information on dosage form thus registered with the medicine as additional information.

Activating a damage cause master registration button 996 shows a screen (not shown) from which to register master information related to the cause of damage of the medicine. As described above, the nurse can register a damage using the damage registration button 896 when the medicine is damaged. In this process, the nurse can register the cause of damage. Typical causes of damage are, "damage due to fall", "spill", "discarded due to mixture with foreign object" and "loss". By registering typical causes of damage using the damage cause registration button 996, registration of damage by the nurse is facilitated.

Activating a designated category master registration button 998 shows a screen (not shown) from which to register a designated category of a medicine. A "designated category" refers to categorization according to the property of the medicine such as "dangerous drug", "poisonous drug" and "psychotropic drug". The medicine master registration button 990 can be used to associate the designated category thus registered with the medicine. Activating a set category master registration button 1000 shows a screen (not shown) from which to register a category of a set of articles. As shown in the set category field 922 of FIG. 21, a category of a set of articles normally corresponds to a medical department. The set of articles registration button 1004 can be used to associate the set category registered herein with the set of articles as additional information. Activating a non-accommodated article master registration button 1002 shows a screen (not shown) from which to register a category of a non-accommodated article (hereinafter, simply referred to as a "non-accommodated article category"). "Non-accommodated article categories" are those with which the non-accommodated article are grouped according to their use such as "anesthesia", "medical operation" and "drip fusion". The medicine master registration button 990 can be used to associate the non-accommodated article category registered herein with the non-accommodated article.

Activating a set of articles registration button 1004 shows a screen (not shown) from which to configure a set of articles. The configuration is for specifying the identification ID of a set of articles shown in the set of articles code field 930, the name of the set of articles, the set category and the type and prescribed number of medicines included in the set of articles.

Activating a unit master registration button 1006 shows a screen (not shown) from which to register the unit of medicines. A unit may be "A (ampule)", "B (bottle)", "V (vial)", "piece", "item" or "set". The nurse can define a unique unit for each of various medicines. A category registration button 1008 is for displaying a screen (not shown) from which to register a category of a medicine. Activating an alert category master registration button 1010 shows a screen (not shown) from which to register an alert category. An alert category is a level of alert. As shown in the category field 868, there are three levels of alert. The texts of alert messages registered by using the alert text master registration button 992 are categorized and registered in association with the levels of alert.

Activating a set medicine category master registration button 1012 shows a screen (not shown) from which to register a set medicine category. Set medicine categories are those with which the non-accommodated articles are grouped. The policy for set medicine categorization may be arbitrarily determined by the nurse. For example, the medicines may be categorized according to their price. The set medicine category master registration button 1012 is also used to register the order of display of the particulars of the set of articles according to the set medicine category. For example, if high priced medicines are given priority in the order of display, high priced medicines are displayed in the earlier pages in the set of articles input screen 940 displaying the particulars of the set of articles. The set medicine category to which each medicine should belong is configured by activating the medicine master registration button 990.

Activating a medicine handling personnel master registration button 1014 shows a screen (not shown) from which to register a nurse. The button 1014 is for configuring data for authenticating and identifying the nurse. As already mentioned with reference to FIG. 15, the medicine handling personnel ID and password are set. Registration of the nurse using the medicine handling personnel master registration button 1014 may be permitted only to an authorized manager. A catalog information registration button 1016 is for setting the content of the catalog 608. A detailed description will be given with reference to FIG. 25. Touching a completion button 1018 shows the login screen 800 again.

Figure 25:
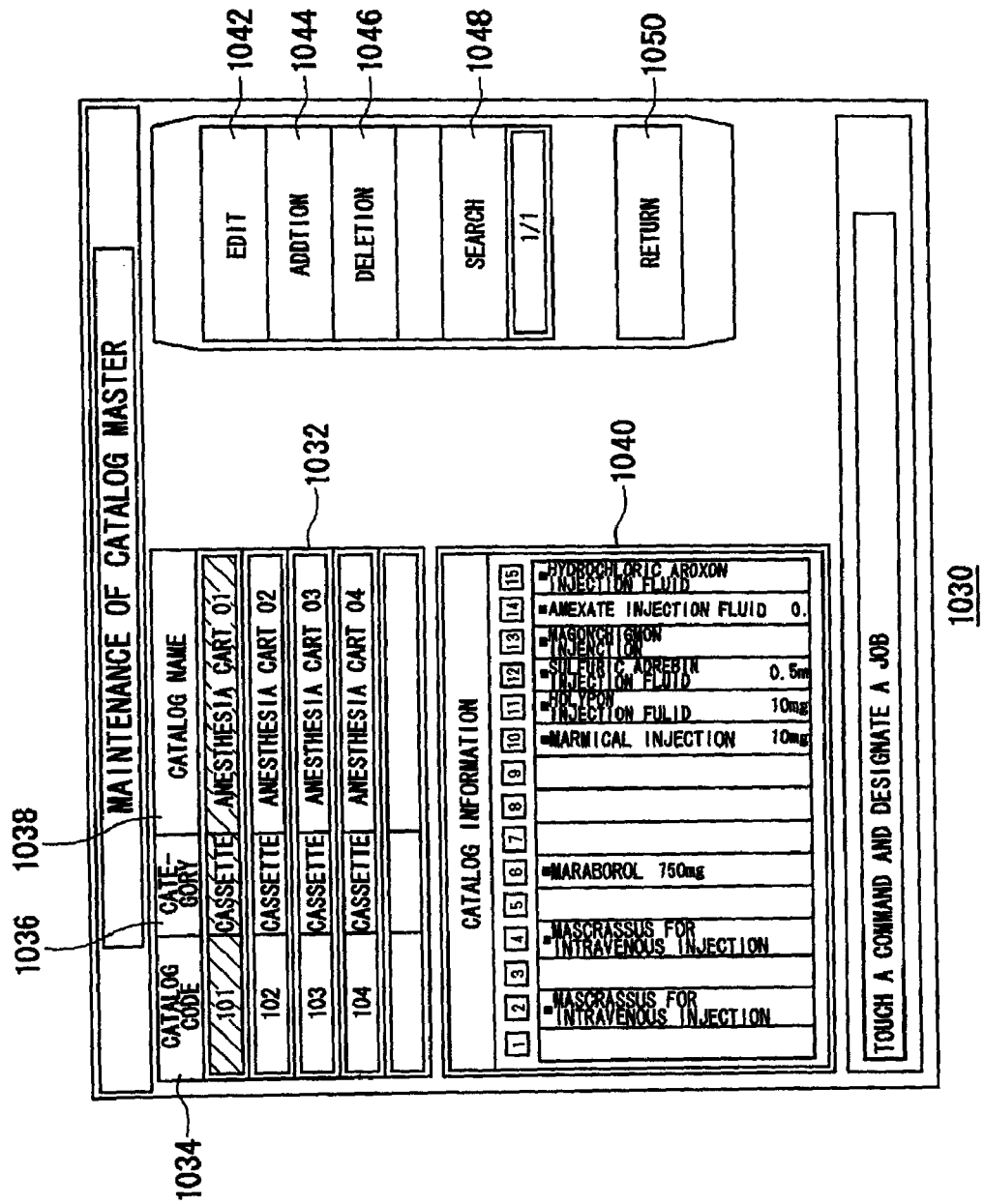
FIG. 25 shows a catalog master maintenance screen of the medicine management apparatus according to the second embodiment.

FIG. 25 shows a catalog master maintenance screen displayed when the catalog information registration button of the maintenance screen is touched.

A catalog list display field 1032 of the catalog master maintenance screen 1030 displays information on the catalogs 608 in the medicine storage 606. The figure shows that there are four catalogs. As described with reference to the unit configuration button 986 of FIG. 24, a larger number of medicine storages 606 may be handled by increasing the number of medicine storages 606.

A catalog code field 1034 displays an ID number for identifying the catalog 608. A category field 1036 displays the kind of container for the accommodated medicine stored in the catalog 608. The description "cassette" indicates an accommodated medicine with the shape of a cassette, such as an ampule or a vial of injection medicine, which is accommodated in the medicine storage 606. Medicines of other types such as medicines contained in a box, injection medicines in a syringe or external medicines. A catalog name field 1038 displays a catalog name valid in each medicine storage 606. Information displayed in the catalog list display field 1032 is configured by using the unit configuration button 986.

A catalog information field 1040 displays accommodated medicines stored in the catalog selected in the catalog list display field 1032. The figure shows that the catalog with the catalog code "101" and the name "anesthesia cart 01" contains a total of fifteen cassettes. Nine accommodated medicines shown in the catalog information field 1040 are accommodated.

An edit button 1042 is for editing the catalog information field 1040. The accommodated medicines which are shown in the catalog information field 1040 and which are to be accommodated in the catalog selected in the catalog list display field 1032 can be edited. An addition button 1044 is for adding an accommodated medicine to be newly listed in the catalog information field 1040. A deletion button 1046 is for deleting an accommodated medicine registered in the catalog information field 1040. A search button 1048 is for searching for an accommodated medicine to be added to the catalog information field 1040. Information related to accommodated medicines may be acquired from the medicine database 742 or acquired from the data storage 776. Touching a return button 1050 shows the maintenance screen 980 again.

Figure 26:
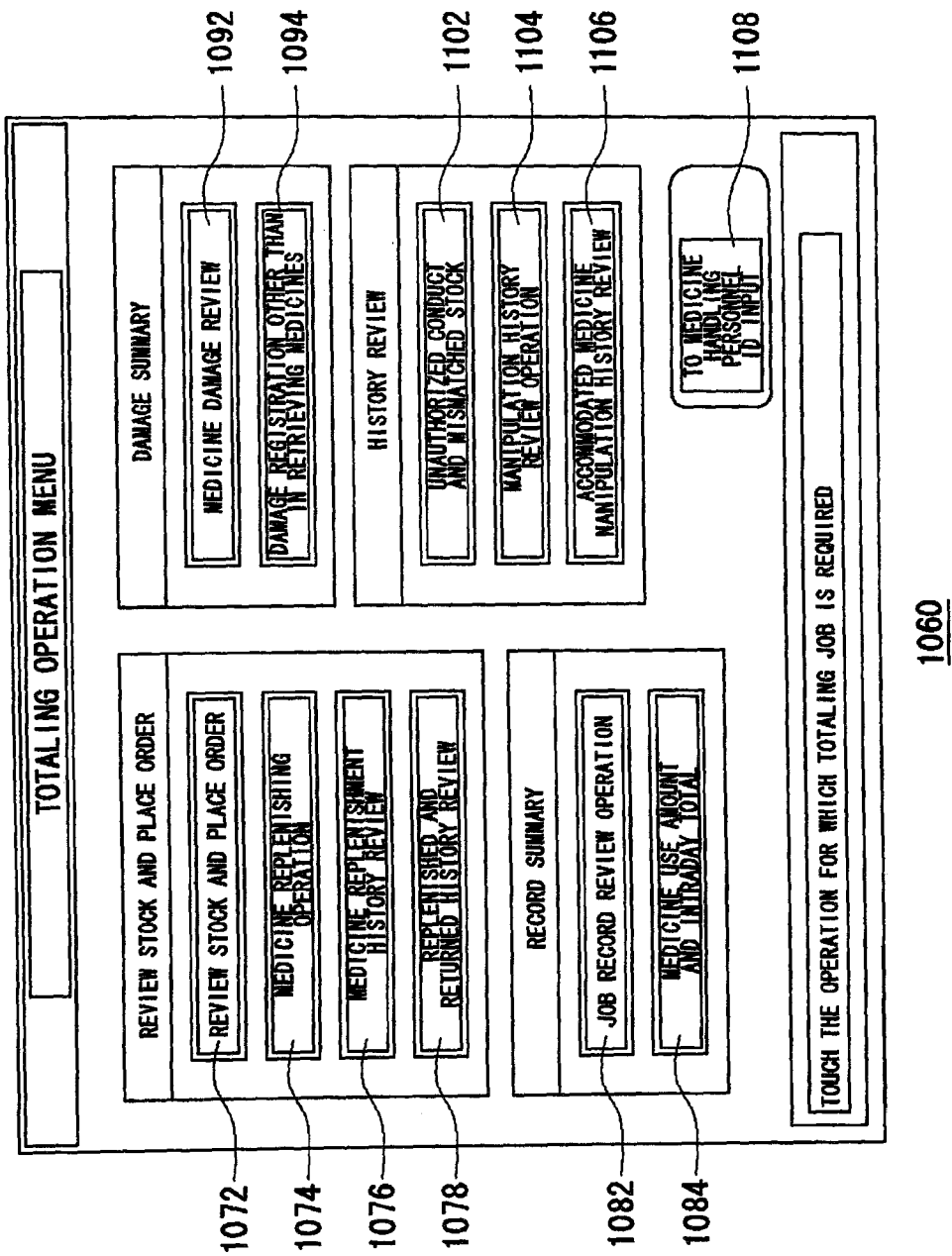
FIG. 26 shows a totaling operation screen of the medicine management apparatus according to the second embodiment.

FIG. 26 shows a totaling operation screen displayed when the totaling operation button of FIG. 15 is touched.

An order operation button 1072 in a totaling operation screen 1060 is used to review the stock and to place orders. Review of the stock in this case means reviewing the status of stock of medicines for which the medicine management apparatus 600 is responsible for management. In other words, not only accommodated medicines but also non-accommodated articles are covered. Normally, orders for medicines are collected by the medical information 720. Alternatively, the medicine management apparatus 600 may order medicines from an outside entity on its own.

A medicine replenishing button 1074 is a button for displaying a screen (not shown) from which to replenish medicines. The nurse performs an operation for replenishing medicines while the screen is being displayed. The method of replenishing is similar to that of storage and retrieval. That is, an input for replenishment of a medicine to be replenished is provided while a screen displayed by activating the medicine replenishing button 1074 is displayed. A medicine replenishment history review button 1076 displays the history of replenishing medicines. A detailed description on this will be given with reference to FIG. 27. A replenished and returned history review button 1078 displays a screen (not shown) showing the history of medicines replenished and then returned. That is, the history of medicines once replenished but returned without being used due to a mistaken order or the like is displayed.

A job record review operation button 1082 is for reviewing the job record of each nurse. A detailed description will be given with reference to FIG. 29. A medicine use amount and intraday total button 1084 is for reviewing the use status of medicines. A detailed description will be given with reference to FIG. 28. A medicine damage confirmation button 1092 is for displaying a screen (not shown) for reviewing damaged medicines. A damage registration button 1094 is for displaying a screen (not shown) from which to register damaged medicines. As mentioned before, a damage can be registered by using the damage registration button 896 when taking medicines out of storage. In the event that a medicine is damaged other than in retrieving the medicine, the damage registration button 1094 is used to register the damage similarly.

A mismatched stock review operation 1102 is for displaying a screen (not shown) for reviewing an unauthorized conduct and a mismatched stock. As mentioned before, retrieval of medicines starts with authentication of a nurse and ends with retrieval of a necessary amount of medicines. However, there may be cases where the system is abnormally terminated or a mismatch of stock occurs. The stock tally display review operation button 1102 enables reviewing such an error status. An manipulation history review operation button 1104 displays the history of manipulation by each nurse in a format shown, for example, in the storage and retrieval information display area 864 of FIG. 20. An accommodated medicine manipulation history review button 1106 is for displaying a screen (not shown) from which to review the record of manipulation regarding accommodated medicines. The screen displays the history of retrieval, replenishment, return, damage and the like for each type of accommodated medicine. Touching a completion button 1108 shows the login screen 800 again.

Figure 27:
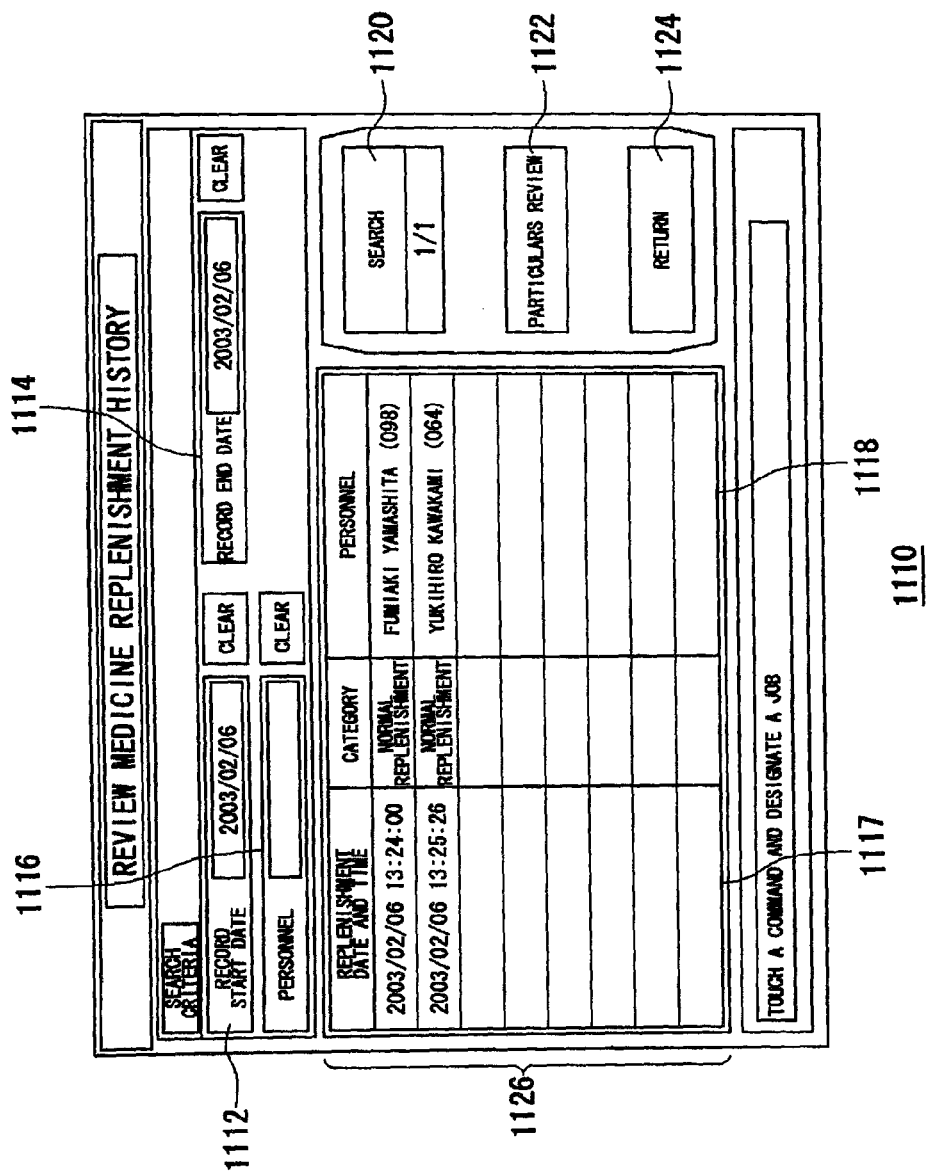
FIG. 27 shows a medicine replenishment history review screen of the medicine management apparatus according to the second embodiment.

FIG. 27 shows a medicine replenishment history review screen displayed when the medicine replenishment history review button is touched in the totaling operation screen.

A record start date field 1112 of the medicine replenishment history review screen 1110 displays a date on which a record of medicine replenishment history is started. A record end date field 1114 displays a date on which the record is ended. By touching the record start date field 1112 or the record end date field 1114, a screen (not shown) to enter the date is displayed, allowing the date to be entered. Entering the name of the nurse in a personnel field 1116 displays only the history of replenishment performed that nurse. A replenishment history field 1126 displays the replenishment history of medicines. A replenishment date and time field 1117 displays the date and time in which the replenishment took place. A personnel field 1118 displays the name and the medicine handling personnel ID of the nurse who performed the replenishment. The figure shows that two nurses "Yamashita Fumiaki" and "Kawakami Yukihiro" replenished medicines on two occasions on Feb. 6, 2003.

A search button 1120 is for searching for the name of the nurse. A replenishment particulars review button 1122 displays the medicines and the amount of medicines replenished in the occasion of replenishment selected by touching in the replenishment history field 1126. Touching a return button 1124 shows the totaling operation screen 1060 again.

Figure 28:
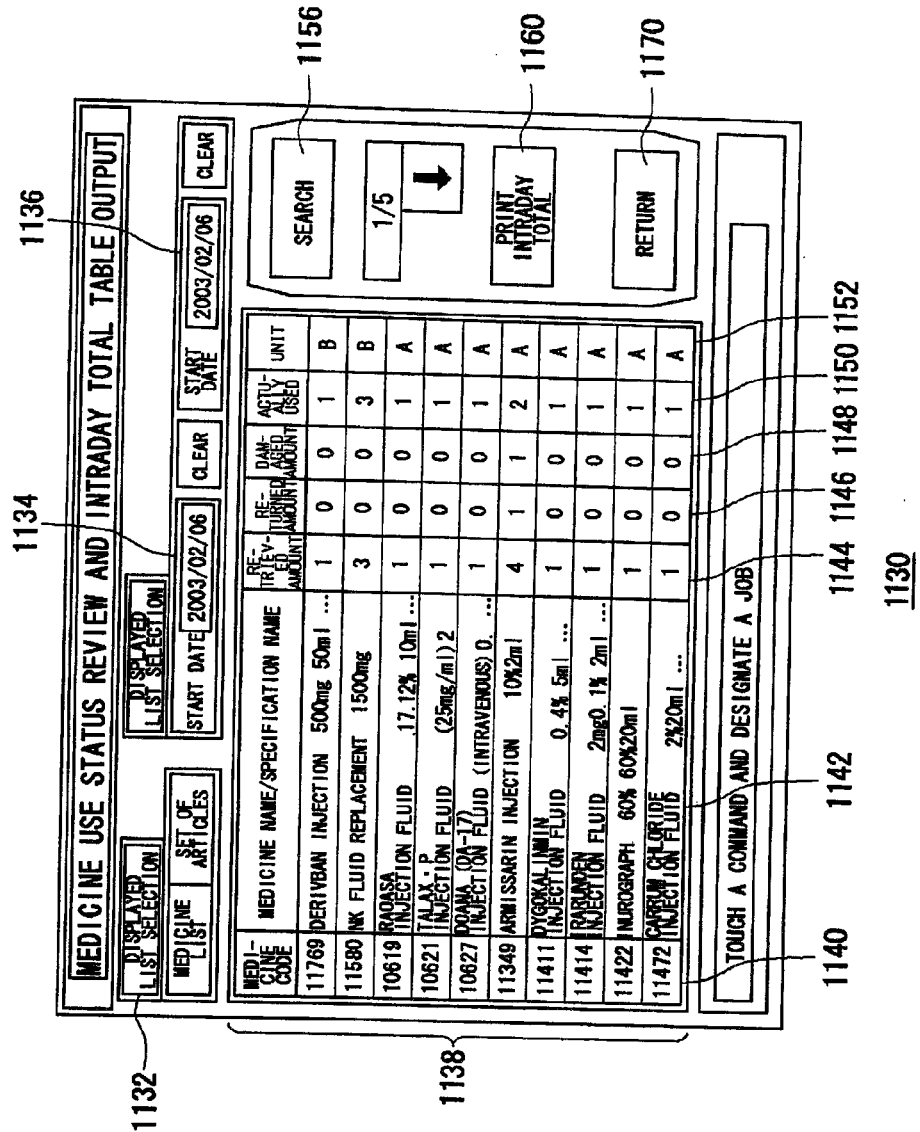
FIG. 28 shows a medicine use status review screen of the medicine management apparatus according to the second embodiment.

FIG. 28 shows a medicine use status review screen displayed when the medicine use amount and intraday total button 1084 is touched in the totaling operation screen.

A medicine use status review screen 1130 allows reviewing the use status of medicines during a predetermined period of time. Activating a displayed medicine list selection field 1132 switches between accommodated medicines and sets of articles as subjects of review. A totaling start date field 1134 displays the start date of a period in which the use status of medicines is reviewed and a totaling end date field 1136 displays the end date of the period. Touching the totaling start date field 1134 or the totaling end date field 1136 displays a screen (not shown) for entering the date, allowing the date to be entered. The figure shows the use status of medicines on Feb. 6, 2003. The medicine use status display field 1138 displays medicines used in this period.

A medicine code field 1140 displays a medicine ID. A medicine name field 1142 displays the name or specification of the medicine. A retrieved amount field 1144 displays the amount of medicines actually taken out of storage. A returned amount field 1146 displays the amount returned. A damaged amount field 1148 displays the amount of medicines retrieved and then registered as being damaged. A use amount field 1150 displays the amount of medicines retrieved and actually used. A unit field 1152 displays the unit of medicines. Referring to FIG. 28, four ampules of the medicine called "Armisusarin Injection 10% 2 ml (provisional name)" with the medicine ID 11349 entered in the medicine code field 1140 are taken out of storage, of which one is returned. Of the remaining three ampules, one is damaged and lost. This means that the remaining two ampules were actually used. A search button 1156 is for searching for a medicine. Touching the search button 1156 displays a screen (not shown) from which to search a medicine, by using a character string or a category as a key. A print button 1160 is for printing the use status of the medicines displayed in the medicine use status display field 1138. Touching a return button 1170 shows the totaling operation screen 1060 again.

Figure 29:
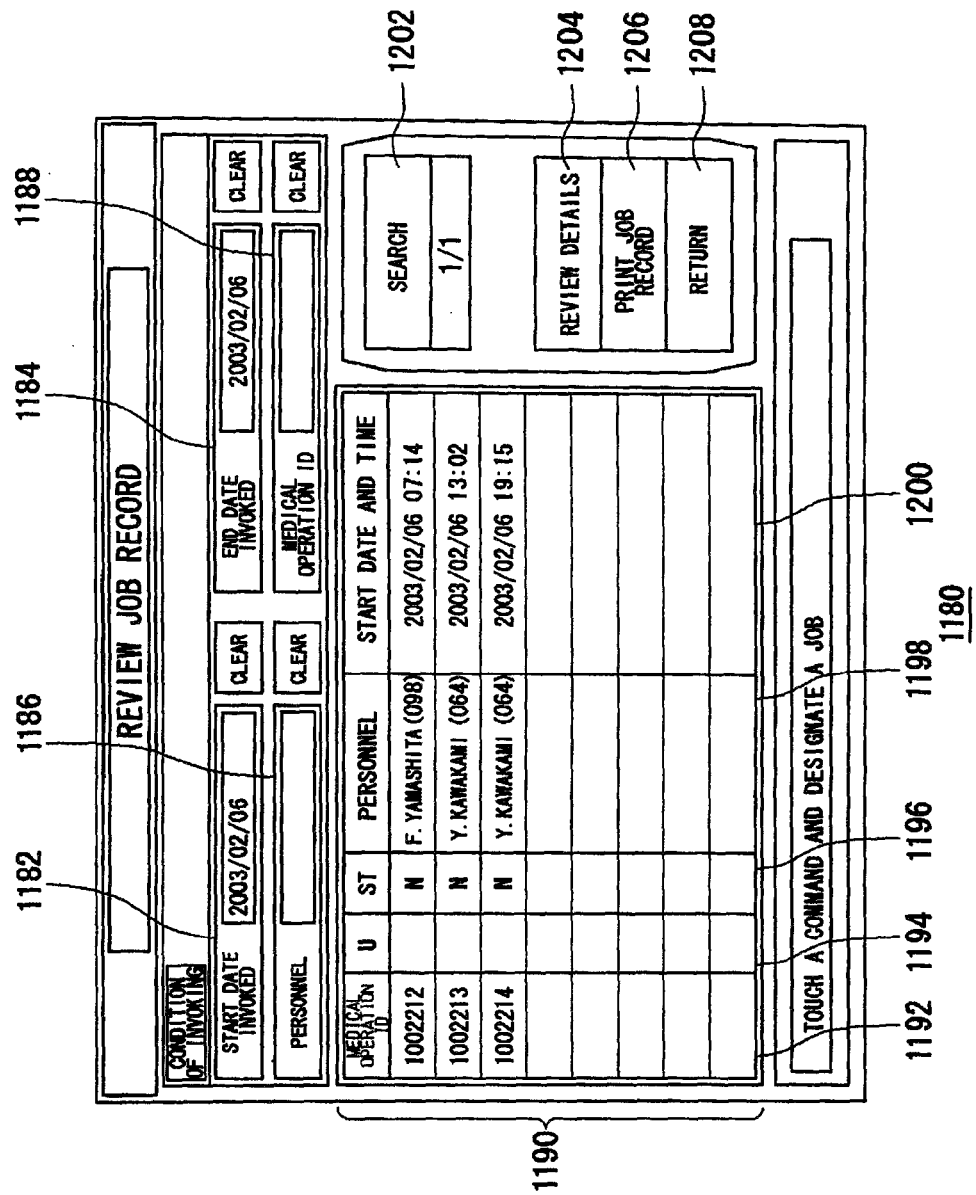
FIG. 29 is a job record review screen of the medicine management apparatus according to the second embodiment.

FIG. 29 is a job record review screen displayed when the job record review operation button in the totaling operation screen is touched.

A job record review screen 1180 is for reviewing the job status of each operation. A job start date field 1182 displays the start date of a period reviewed, and a job end date field 1184 displays the end date of the period. Touching the job start date field 1182 or the job end date field 1184 displays a screen (not shown) for entering the date, allowing the date to be entered. The figure shows that the job record on Feb. 6, 2003 is reviewed. Entering the name of a nurse in the personnel field 1186 displays only the job record performed by that nurse. Entering a medical operation ID in a medical operation ID field 1188 displays only the job record related to that medical operation.

A job record field 1190 displays a job record of each medical operation. A medical operation ID field 1192 displays a medical operation ID. An urgent job field 1194 shows that the job is associated with an urgent interruption using the urgent interruption button 884 of FIG. 18. A job status field 1196 displays the status of the job. "Done" in the figure indicates the job was completed normally. When application software is terminated abnormally, it is indicated as such in this field. A personnel field 1198 displays the name and the medicine handling personnel ID of the nurse who has done the job associated with the medical operation. A job start date and time field 1200 displays the date and time in which the job is started.

A search button 1202 is for doing a search. Touching the search button 1202 shows a screen (not shown) from which to search for a medical operation or a nurse. Search for a medical operation may be done by using the particulars of the medical operation, the name of the patient or the name of the responsible doctor as a key, instead of using the medical operation ID as a key. Search for a nurse is done by using the medicine handling personnel ID or the nurse name as a key. A job detail review button 1204 is for reviewing the details of the job selected in the job record field 1190. The details are displayed on a screen in a manner similar to the medicine use status review screen 1130 already described. Activating a job record print button 1206 prints the history of manipulation for each job selected in the job record field 1190. More specifically, a history as shown in the storage and retrieval information display area 864 of FIG. 20 is printed. Touching a return button 1208 shows the totaling operation screen 1060 again.

As described above, the medicine management apparatus 600 acquires necessary information from databases included in the medical information system 720. Alternatively, the data storage 776 of the medicine management apparatus 600 may store all necessary information for operation. A point of consideration is that, in case multiple medicine management apparatuses 600 are operated, a majority of data can be shared between the apparatuses. Further, the medical information system 720 usually holds much of the data required by the medicine management apparatus 600. Therefore, by allowing the medicine management apparatus 600 to exchange data with the medical information system 720, the medicine management apparatus 600 and the medical information system 720 can be operated in a complementary manner.

The medicine management apparatus 600 processes data acquired from the medical information system 720 before using the same. Data created in the medicine management apparatus 600 is also transmitted to the medical information system 720. Hereinafter, the data structure of the databases included in the medical information system 720 will be described.

FIG. 30 shows the data structure of the medicine database.

The medicine database 742 stores information related to the medicines used in the hospital 700. The figure shows the data structure related to accommodated medicines in cassettes. The medicine database 742 may store data for the entirety of the medicines. Alternatively, the medicine database 742 may store data for medicines that need management such as those medicines at a specified price or higher.

A JAN code field 1210 displays the JAN code of a medicine. A JAN code normally comprises four codes for identifying products, including a country code, a manufacturer code, a product item code and a check digit. A medicine code field 1212 also displays a code for identifying the medicine. However, the medicine code may be unique to the hospital 700. A medicine name field 1214 displays the name of the medicine. A specification name field 1216 displays the specification of the medicine. A beneficial effect field 1216 displays the beneficial effect of the medicine. A designated category field 1220 displays the designated category of the medicine. A diameter field 1222, a height field 1224 and a cassette size field 1226 display information related to the size of the accommodated medicine, showing the diameter, height and cassette size, respectively. The data shown here need not be stored solely by the medicine database 742. The data storage 776 of the medicine management apparatus 600 may store part of the data.

FIG. 31 shows the data structure of the medical operation database.

The medical operation database 736 stores data related to medical operations. A medical operation ID field 1230 displays a medical operation ID. A patient ID field 1232 displays a patient ID. A scheduled operation technique field 1234 displays the particulars of a scheduled medical operation. A doctor field 1236 displays the name of the responsible doctor, and a surgeon field 1236 displays the name of the surgeon. The responsible doctor or the surgeon may be identified by an ID number identifying the doctor. A scheduled date field 1240 displays the date on which the medical operation is scheduled. The data in the top row in the figure corresponds to the data entered in the worksheet 840 shown in FIG. 17. That is, the medical operation ID is "1002352", the patient ID is "9305277", and the medical operation scheduled to be performed is "low anterior resection of the rectum". The responsible doctor and surgeon is "Kitamura Keisuke" and the scheduled date is Jul. 31, 2003.

FIG. 32 shows the data structure of the patient database.

The patient database 740 stores information related to the patients. A patient ID field 1250 displays a patient ID. The patient ID field 1250 corresponds to the patient ID field 1232 of the medical operation database 736. A patient name field 1252 displays the name of the patient. An age field 1254 displays the age of the patient, a sex field 1256 displays the sex of the patient and a blood type field 1258 displays the blood type of the patient. A height field 1260 field displays the height of the patient, and a weight field 1262 displays the weight of the patient. A hospital admission field 1264 displays whether the patient is an inpatient or an outpatient. The data in the top row in the figure corresponds to the data entered in the worksheet 840 shown in FIG. 17. That is, the patient ID is "9305277", the patient's name is "Harumi Sato", the age is "eight", the sex is "female" and the blood type is "B". The height is 127 cm and the weight is 26.3 kg. The patient is now hospitalized.

As the medicine management apparatus 600 scans the medical operation ID field 850 of the worksheet 840, the apparatus acquires the data corresponding to the medical operation ID "100236" from the medical operation database 736. The apparatus also acquires from the patient database 740 the data corresponding to the patient ID "9305277", which is acquired from the patient ID field 842. Thus, the medicine management apparatus 600 acquires data necessary for its process from the medical information system 720 by using ID numbers as keys.

FIG. 33 shows the data structure of the retrieval database.

The retrieval database 738 stores the status of the medicines taken out of the medicine management apparatus 600. The medicine management apparatus 600 transmits information regarding retrieval to the retrieval database 738 at regular time intervals. For example, the information regarding retrieval is in the format as shown in FIG. 28. As the stock of medicines under its control undergoes a change, the medicine management information 600 may transmit associated information to the retrieval database 738.

A machine ID field 1270 displays a machine ID, which is an ID number for specifying the medicine management apparatus 600. A medicine name field 1272 displays the name of a medicine. The medicine displayed here is managed by the medicine management apparatus 600. A medicine identification ID field 1274 displays a medicine identification ID. A category field 1276 displays the category of the medicine, namely, "accommodated medicine", "non-accommodated medicine" or "non-accommodated medical resource". A retrieved amount field 1278 displays the amount of medicines retrieved in a predetermined period of time. A unit field 1280 displays the unit of the medicine. A stocked amount field 1282 displays the amount of stock in the medicine management apparatus 600.

The retrieval database 738 allows the stock control system 734 to know the status of the medicines in the hospital 700 in an integrated manner. The electronic patient chart system 732 manages electronic chart information for the patients. The medical accounting system 730 performs a medical accounting process based upon the information stored in the medical operation database 736 and the patient database 740.

Figure 34:
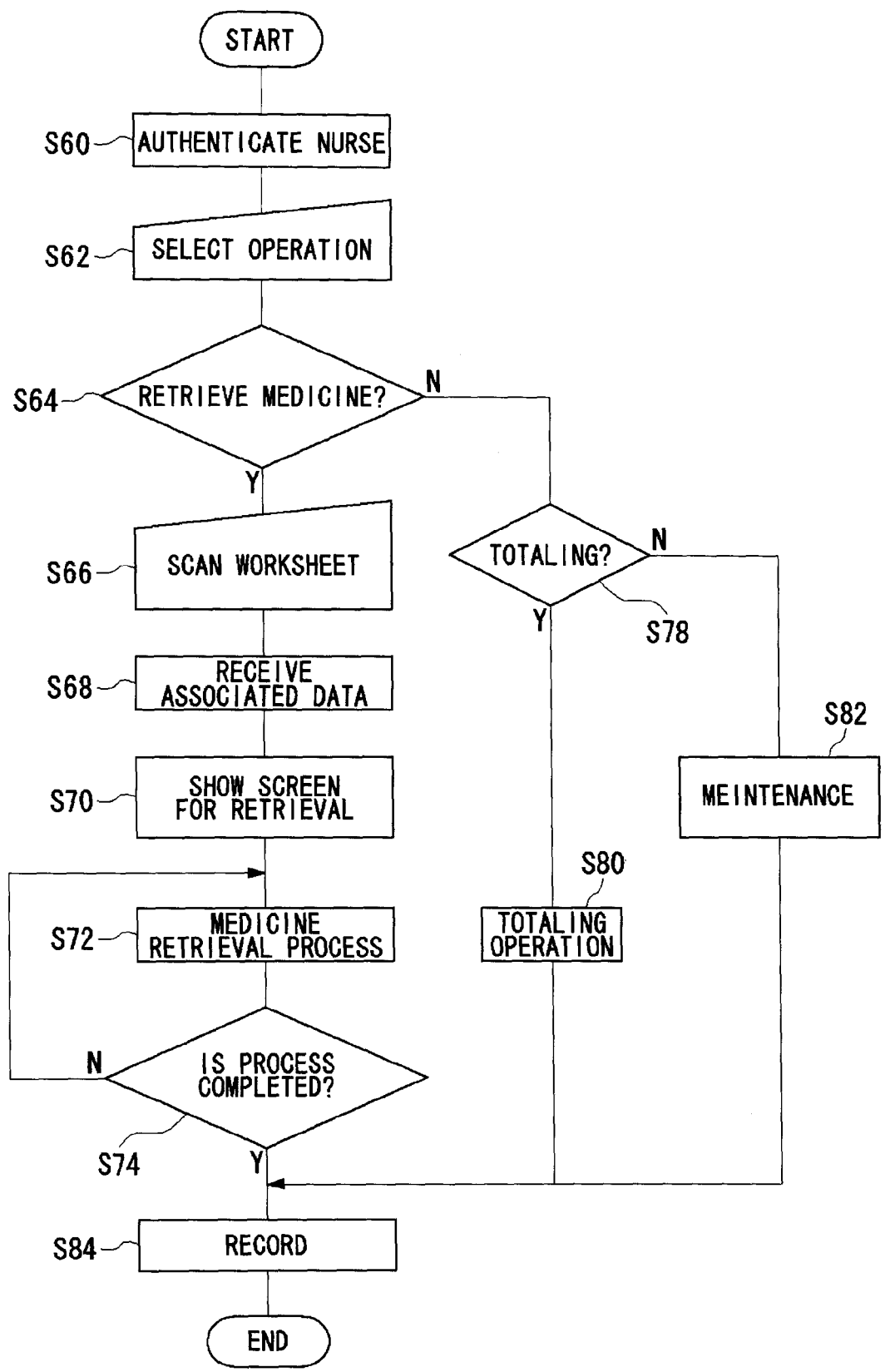
FIG. 34 is a flowchart regarding a process in the medicine management apparatus according to the second embodiment.

FIG. 34 is a flowchart regarding the process in the medicine management apparatus.

The medicine management apparatus 600 first authenticates a nurse in the login screen (S60). The authenticated nurse selects "retrieval of medicine", "totaling" or "maintenance" in the login screen 800 (S62). If the medicine retrieval operation button 808 is touched to select the medicine retrieval operation (Y in S64), the work sheet scanning screen 830 is displayed. The nurse enters the medical operation ID entered in the worksheet (S66).

The controller 762 refers to the medical operation ID thus read so as to receive from the medical information system 720 the corresponding particulars of the medical operation (S68). If the reception of data fails due to, for example, a failure in the medical information system 720, an error alert is output and the initial medicine retrieval screen 860 is shown.

If the particulars of the corresponding medical operation are received, the initial medicine retrieval screen 860 is shown (S70). As described above, the nurse takes out medicines from this screen (S72). When all steps are completed (Y in S74), the details of the job are recorded in the data storage 776 (S84), before terminating the process. The recorded information may be transmitted to the database of the medical information system 720 immediately. Alternatively, the recorded information may be transmitted to the integrated terminal 622. The integrated terminal 622 may then collect the information acquired from the medicine management apparatuses 600 for transmission to the hospital 700.

If the totaling operation button 810 is selected in the login screen 800 (N in S64, Y in S78), the totaling operation screen 1060 of FIG. 26 is shown where totaling operations are undertaken (S80). If the maintenance operation button 812 is selected in the login screen 800 (N in S78), the maintenance screen 980 of FIG. 24 is shown where operations for configuration are undertaken.

As described, information on the storage and retrieval of medicines used at a site of medical care is efficiently stocked in the medical information system 720. This makes it easy to collectively manage the storage and retrieval of medicines in the entire hospital. It will be noted that information to be referred to in controlling the stock of medicines in the medical information system 720 is generated at a site of medical care. The medicine management apparatus 600 can effectively manage the storage and retrieval of medicines occurring at a site of medical care and as such helps the medical information system 720 to be operated accurately. Further, as described above, the medicine management apparatus 600 is provided with an intuitive interface for storage and retrieval of medicines. Additionally, provisions for detecting human errors and system errors are effective in reducing mistakes in management of medicines.

Described above is an explanation of the present invention based on the second embodiment. The second embodiment is only illustrative in nature and it will be obvious to those skilled in the art that variations in constituting elements and processes are possible and that such variations are also within the scope of the present invention.

The following technical ideas are encompassed by the embodiments described above and variations thereof.

(1) A medicine management apparatus comprising: a medicine storage which stores a plurality of medicines used at a site of medical care; a detecting mechanism which, when a medicine handling personnel manipulates the apparatus to store or retrieve an accommodated medicine to be accommodated in the apparatus, physically detects the target accommodated medicine for which the apparatus is manipulated, differentiating it from the other accommodated medicines; an accommodated medicine counter which counts each type of the plurality of accommodated medicines; a stored or retrieved accommodated medicine information recorder which records, on a recording medium, stored or retrieved accommodated medicine information which relates to accommodated medicines that are stored or retrieved; a display unit which at least displays the stored or retrieved accommodated medicine information; a format converter which converts the format in order to allow an external database to store at least retrieved accommodated medicine information related to retrieval, which information constitutes the stored or retrieved accommodated medicine information; a communicating unit which transmits the retrieved accommodated medicine information thus converted to the database; and a controller which at least controls the stored or retrieved medicine information recorder, the display unit, the format converter and the communicating unit in an integrated manner.

(2) The medicine management apparatus of (1) further comprising: a stored or retrieved non-accommodated article input unit which, when a medicine handling personnel stores or retrieves a non-accommodated article not stored in the medicine storage, accepts an input regarding the non-accommodated article stored or retrieved; and a stored or retrieved non-accommodated article information recorder which records, on a recording medium, stored or retrieved non-accommodated article information which relates to non-accommodated articles that are stored or retrieved.

(3) The medicine management apparatus of (1) further comprising a movable seat on which the apparatus main body is installed.

(4) The medicine management apparatus of (1), wherein, when the detecting mechanism detects the storage or retrieval of the accommodated medicine, the controller causes the display unit to display the name of the target accommodated medicine on a real time basis.

(5) The medicine management apparatus of (2) further comprising: a non-accommodated article identification information detector which reads non-accommodated article identification information assigned to the non-accommodated articles, wherein the stored or retrieved non-accommodated article input unit may accept the input by allowing the non-accommodated article identification information detector to read the non-accommodated article identification information.

(6) The medicine management apparatus of (1) further comprising: a medicine handling personnel ID recorder which records a medicine handling personnel ID, assigned to identify the medicine handling personnel, on a recording medium; and a medicine handling personnel ID input unit which accepts an input of the medicine handling personnel ID, wherein the communicating unit may be further provided with the function of receiving patient information from an external database which stores the patient information, and the stored or retrieved accommodated medicine information recorder may record the stored or retrieved accommodated medicine information based upon the medicine handling personnel ID associated with the medicine handling personnel who manipulated the apparatus to store or retrieve the medicine, and upon the patient information received.

(7) The medicine management apparatus of (1), wherein the stored or retrieved accommodated medicine information recorder may further be provided with at least one of the function of recording replenishment history information which relates to replenishment of accommodated medicines, and the function of recording use history information related to accommodated medicines used in a predetermined period.

(8) The medicine management apparatus of (2), wherein the stored or retrieved non-accommodated article input unit may accept an input for each set of articles which comprises at least one non-accommodated article.

(9) The medicine management apparatus of (8), further comprising: a set of articles definition input unit which accepts an input by the medicine handling personnel to define a new set of articles.

(10) The medicine management apparatus of (8), further comprising: an amount change input unit which accepts an input from the medicine handling personnel regarding a change in the amount of non-accommodated articles included in the set of articles, wherein the stored or retrieved non-accommodated article input unit may accept an input regarding the set of articles in which the amount is changed.

(11) The medicine management apparatus of (10), wherein when the amount change input unit accepts an input regarding a change in the amount, the controller may cause the display unit to display the associated non-accommodated article in a manner different from the way it is normally displayed.

(12) The medicine management apparatus of (1), further comprising: a manipulation history generation unit which generates manipulation history information regarding the history of manipulation by the medicine handling personnel and stores the same in a recording medium.

(13) The medicine management apparatus of (1), further comprising: a medical operation identification information detector which reads medical operation identification information assigned to medical operations to be performed for patients, wherein the communicating unit transmits the medical operation identification information thus read to an external database which stores detailed information on the medical operation corresponding to the medical operation identification information and receives, from the database, the detailed information corresponding to the medical operation identification information thus read.

(14) The medicine management apparatus of (8), further comprising: a prompting information output unit which prompts the medicine handling personnel for review, when the same non-accommodated article as included in a set of articles is retrieved in addition to the set of articles.

(15) A medicine management system including the medicine management apparatus of (1) and a stock database which, connected to the medicine management apparatus via a network, stores data related to the stock status of the accommodated medicines, wherein the medicine management apparatus transmits retrieved accommodated medicine information to the stock database.

INDUSTRIAL USABILITY

As described above, the present invention is applicable to a system for managing medicines used at a site of medical care.

What is claimed is:

1. A medicine management apparatus comprising:
   a medicine storage which stores a plurality of medicines used at a site of medical care;
   a detecting mechanism that, when a medicine handling personnel manipulates the apparatus to store or retrieve a target accommodated medicine to be accommodated in the apparatus, physically detects the target accommodated medicine from the plurality of medicines for which the apparatus is manipulated, differentiating the target accommodated medicine from other accommodated medicines;
   an accommodated medicine counter which counts each type of the plurality of medicines;
   a stored or retrieved accommodated medicine information recorder which records, on a recording medium, stored or retrieved accommodated medicine information relating to accommodated medicines that are stored or retrieved;
   a display unit which at least displays the stored or retrieved accommodated medicine information;
   a format converter which converts a format of the stored or retrieved accommodated medicine information in order to allow an external database to store the stored or retrieved accommodated medicine information;
   a communicating unit which transmits at least retrieved accommodated medicine information thus converted to the database;
   a controller which at least controls the stored or retrieved medicine information recorder, the display unit, the format converter and the communicating unit in an integrated manner;
   a stored or retrieved non-accommodated article input unit which, when a medicine handling personnel stores or retrieves a non-accommodated article not stored in the medicine storage, accepts an input regarding the non-accommodated article stored or retrieved; and
   a stored or retrieved non-accommodated article information recorder which records, on a recording medium, stored or retrieved non-accommodated article information which relates to non-accommodated articles that are stored or retrieved, wherein the stored or retrieved non-accommodated article input unit accepts an input for each set of articles comprising at least one non-accommodated article.

2. The medicine management apparatus of claim 1, further comprising a movable seat on which a main body of the medicine management apparatus is installed.

3. The medicine management apparatus of claim 1, wherein, when the detecting mechanism detects the storage or retrieval of the accommodated medicine, the controller causes the display unit to display the name of the target accommodated medicine on a real time basis.

4. The medicine management apparatus of claim 1 further comprising: a non-accommodated article identification information detector which reads non-accommodated article identification information assigned to the non-accommodated articles, wherein the stored or retrieved non-accommodated article input unit may accept the input by allowing the non-accommodated article identification information detector to read the non-accommodated article identification information.

5. The medicine management apparatus of claim 1, further comprising:
   a medicine handling personnel ID recorder which records a medicine handling personnel ID, assigned to identify the medicine handling personnel, on a recording medium; and
   a medicine handling personnel ID input unit which accepts an input of the medicine handling personnel ID, wherein the communicating unit may be further provided with the function of receiving patient information from an external database which stores the patient information, and the stored or retrieved accommodated medicine information recorder may record the stored or retrieved accommodated medicine information based upon the medicine handling personnel ID associated with the medicine handling personnel who manipulated the apparatus to store or retrieve the medicine, and upon the patient information received.

6. The medicine management apparatus of claim 1, wherein the stored or retrieved accommodated medicine information recorder may further be provided with at least one of the function of recording replenishment history information which relates to replenishment of accommodated medicines, and the function of recording use history information related to accommodated medicines used in a predetermined period.

7. The medicine management apparatus according to claim 1, further comprising:
   a set of articles definition input unit which accepts an input by the medicine handling personnel to define a new set of articles.

8. The medicine management apparatus according to claim 1, further comprising:
   an amount change input unit which accepts an input from the medicine handling personnel regarding a change in an amount of non-accommodated articles included in the set of articles, wherein the stored or retrieved non-accommodated article input unit accepts an input regarding the set of articles in which the amount is changed.

9. The medicine management apparatus according to claim 8, wherein when the amount change input unit accepts an input regarding a change in the amount, the controller causes a corresponding change in a display of an associated non-accommodated article so that the display of the associated non-accommodating article after receiving the input from the medicine handling personnel is different from a display of the associated non-accommodating article prior to receiving the input from the medicine handling personnel.

10. The medicine management apparatus of claim 1, further comprising:
a manipulation history generation unit which generates manipulation history information regarding the history of manipulation by the medicine handling personnel and stores the same in a recording medium.

11. The medicine management apparatus of claim 1, further comprising:
a medical operation identification information detector which reads medical operation identification information assigned to medical operations to be performed for patients, wherein the communicating unit transmits the medical operation identification information thus read to an external database which stores detailed information on the medical operation corresponding to the medical operation identification information and receives, from the database, the detailed information corresponding to the medical operation identification information thus read.

12. The medicine management apparatus according to claim 1, further comprising:
a prompting information output unit which prompts the medicine handling personnel for review, when an additional non-accommodated article similar to articles included in the set of articles is retrieved in addition to the set of articles.

13. The medicine management system including the medicine management apparatus of claim 1 and a stock database which, when connected to the medicine management apparatus via a network, stores data related to the stock status of the accommodated medicines, wherein the medicine management apparatus transmits retrieved accommodated medicine information to the stock database.

* * * * *